(12) United States Patent
Barsoum et al.

(10) Patent No.: US 9,416,011 B2
(45) Date of Patent: *Aug. 16, 2016

(54) COMPOSITIONS COMPRISING FREE-STANDING TWO-DIMENSIONAL NANOCRYSTALS

(71) Applicant: DREXEL UNIVERSITY, Philadelphia, PA (US)

(72) Inventors: Michel W. Barsoum, Moorestown, NJ (US); Yury Gogotsi, Warminster, PA (US); Michael Naguib Abdelmalak, Philadelphia, PA (US); Olha Mashtalir, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/881,261

(22) Filed: Oct. 13, 2015

(65) Prior Publication Data

US 2016/0115035 A1  Apr. 28, 2016

Related U.S. Application Data

(63) Continuation of application No. 14/094,966, filed on Dec. 3, 2013, now Pat. No. 9,193,595, which is a continuation-in-part of application No. PCT/US2012/043273, filed on Jun. 20, 2012.

(60) Provisional application No. 61/499,318, filed on Jun. 21, 2011, provisional application No. 61/521,428, filed on Aug. 9, 2011, provisional application No. 61/587,172, filed on Jan. 17, 2012, provisional application No. 61/733,015, filed on Dec. 4, 2012.

(51) Int. Cl.
*C01B 31/30* (2006.01)
*C01C 3/08* (2006.01)
*C07C 233/03* (2006.01)
(Continued)

(52) U.S. Cl.
CPC ............ *C01B 31/305* (2013.01); *C01C 3/08* (2013.01); *C07C 233/03* (2013.01); *C07C 275/00* (2013.01); *C07C 317/04* (2013.01); *C08K 3/14* (2013.01); *C08K 3/28* (2013.01); *H01G 11/04* (2013.01); *H01G 11/32* (2013.01); *H01M 4/366* (2013.01); *H01M 4/58* (2013.01); *H01M 4/587* (2013.01); *H01M 10/0525* (2013.01); *C01P 2002/08* (2013.01); *C01P 2002/20* (2013.01); *C01P 2002/72* (2013.01);
(Continued)

(58) Field of Classification Search
None
See application file for complete search history.

(56) References Cited

U.S. PATENT DOCUMENTS 4,801,368 A  1/1989  Yamashita et al.
6,180,049 B1  1/2001  Jang et al.
(Continued)

FOREIGN PATENT DOCUMENTS

EP  1381099 A1  1/2004
EP  0948067 A1  10/2009
(Continued)

OTHER PUBLICATIONS

Barsoum et al, "Room-Temperature Deintercalation and Self-Extrusion of Ga from Cr2GaN", Science, May 7, 1999, 284(5416), 937-939.
(Continued)

*Primary Examiner* — Maria J Laios
*Assistant Examiner* — Robert S Carrico
(74) *Attorney, Agent, or Firm* — Baker & Hostetler LLP

(57) ABSTRACT

The present invention is directed to compositions comprising free standing and stacked assemblies of two dimensional crystalline solids, and methods of making the same.

34 Claims, 59 Drawing Sheets

(51) Int. Cl.

| | |
|---|---|
| C07C 275/00 | (2006.01) |
| C08K 3/14 | (2006.01) |
| C08K 3/28 | (2006.01) |
| H01G 11/04 | (2013.01) |
| H01M 4/36 | (2006.01) |
| H01M 4/58 | (2010.01) |
| H01M 4/587 | (2010.01) |
| H01M 10/0525 | (2010.01) |
| C07C 317/04 | (2006.01) |
| H01G 11/32 | (2013.01) |

(52) U.S. Cl.
CPC ........ C01P 2002/82 (2013.01); C01P 2002/85 (2013.01); C01P 2004/03 (2013.01)

(56) References Cited

U.S. PATENT DOCUMENTS

| | | | |
|---|---|---|---|
| 6,555,268 | B1 | 4/2003 | Inoue et al. |
| 7,446,190 | B2 | 11/2008 | Sadelain et al. |
| 2002/0068488 | A1 | 6/2002 | Tuller et al. |
| 2003/0148184 | A1 | 8/2003 | Omaru et al. |
| 2003/0224168 | A1 | 12/2003 | Mack et al. |
| 2004/0048157 | A1 | 3/2004 | Neudecket et al. |
| 2007/0065725 | A1 | 3/2007 | Inoue |
| 2007/0066503 | A1 | 3/2007 | Basaly |
| 2009/0017332 | A1 | 1/2009 | Kisi et al. |
| 2010/0236937 | A1 | 9/2010 | Rosvall et al. |
| 2010/0322909 | A1 | 12/2010 | Okada et al. |
| 2011/0017585 | A1 | 1/2011 | Zhamu et al. |
| 2011/0104464 | A1 | 5/2011 | Pyzik et al. |

FOREIGN PATENT DOCUMENTS

| | | |
|---|---|---|
| JP | H0878018 A | 3/1996 |
| JP | H10112316 A | 4/1998 |
| JP | 2005/158725 A | 6/2005 |
| JP | 2007/214137 A | 8/2007 |
| WO | WO 02/081372 A2 | 10/2002 |
| WO | WO 02/096799 A2 | 12/2002 |
| WO | WO 2005/007566 A2 | 1/2005 |
| WO | WO 2006/112869 A2 | 10/2006 |
| WO | WO 2007/093011 A1 | 8/2007 |
| WO | WO 2007/121931 A2 | 11/2007 |
| WO | WO 2009/063031 A2 | 5/2009 |
| WO | WO 2009/091826 A2 | 7/2009 |
| WO | WO 2010/128492 A1 | 11/2010 |

OTHER PUBLICATIONS

Barsoum et al, "The Topotactic Transformation of Ti3SiC2 into a Partially Ordered Cubic Ti(C0.67Si0.06) Phase by The Diffusion of Si into Molten Cryolite", Journal of the Electrochemical Society, 1999, 146(10), 3919-3923.
Barsoum, "The MN+1AXN phases: New Class of Solids", Progress in Solid State Chemistry, Jan. 1, 2000, 28(1-4), 201-281.
Barsoum, et al., "Synthesis and Characterization of a Remarkable Ceramic: Ti3SiC2," J Amer. Chem. Soc., 1996 79(7), 1953-1956.
Barsoum, et al., "The MAX Phases: Unique New Carbide and Nitride Materials", American Scientist, Jul.-Aug. 2001, 89:334-343.
Barsoum, "Physical Properties of the MAX phases", Encyclopedia of Materials: Science and Technology, 2006, 11 pgs.
Chang, et al., "Synthesis of a new graphene-like transition metal carbide by de-intercalating $Ti_3AlC_2$", Mater. Lett. 109 (2013) 295-298.
Chen, et al, "Microstructure and Phase Transformation of Ti 3 AC 2 (A=Al, Si) in Hydrofluoric Acid Solution", Crystal Research and Technology, Oct. 27, 2014, 49(10), 813-819.
Chen, et. al., "In-situ Synthesis of $Ti_3AlC_2/TiC$—$Al_2O_3$ Composite from $TiO_2$—Al—C System", J. Mater. Sci. Technol., 22(4), Nov. 2006, 455-458.

Coleman et al, "Two-Dimensional Nanosheets Produced by Liquid Exfoliation of Layered Materials", Science, Feb. 4, 2011, 331, 568-571.
Eis, PS et al, Accumulation of miR-155 and BIC RNA in Human B Cell Lymphomas. Proceedings of the National Academy of Sciences of the United States of America, Mar. 8, 2005, 102(10), 3627-3632.
Eklund, et al, "The Mn+1AXn Phases: Materials Science and Thin-Film Processing", Thin Solid Films, 2010, 518, 1851-1878.
European Patent Application No. 12803351.1: Supplementary European Search Report dated Jan. 30, 2015, 14 pages.
Ghidiu, et al., "Conductive Two Dimensional Titanium Carbide 'Clay' with High Volumetric Capacitance", Nature, 516 (2014) 78-81.
Hendaoui, et al., Ti—Al—C MAX Phases by Aluminothermic Reduction Process, International Journal of Self-Propagating High-Temperature Synthesis, 17 (2008) 125-128.
Hu, "Low Temperature Thermal Expansion, High Temperature Electrical Conductivity, and Mechanical Properties of Nb4AlC3 Ceramic Synthesized by Spark Plasma Sintering", Journal of Alloys and Compounds, Nov. 13, 2009, 487(1-2), 675-681.
Hu, et al., "A New Family of Promising Hydrogen Storage Medium", J. Phys. Chem., A 117 (2013 14253-14260.
Hu, et al., "Two-Dimensional Sc2C: A Reversible and High-Capacity Hydrogen Storage Material Predicted by First-Principles Calculations", Int. J. Hydrogen Energy, Jul. 2014, vol. 39(20), 10606-10612.
International Patent Application No. PCT/US13/072733: The International Search Report and the Written Opinion dated Mar. 28, 2014, pp. 1-12.
International Patent Application No. PCT/US13/64503: The International Search Report and the Written Opinion dated Jan. 24, 2014, pp. 1-13.
Korzhavyi, et al, "Ab Initio Study of Phase Equilibria in $TiC_x$", Physical Review Letters, Dec. 18, 2001, 88(1), 1-4.
Kulkarni et al, Thermal Expansion and Stability of Ti2SC in Air and Inert Atmospheres, Journal of Alloys and Compounds, 2009, 469, 395-400.
Mogilevsky, et al, "The Structure of Multilayered Titania Nanotubes Based on Delaminated Anatase", Chemical Physics Letters, 2008, 460, 517-520.
Myhra, et al., "Crystal-Chemistry of the $Ti_3AlC_2$ and $Ti_4AlN$ Layered Carbide/Nitride Phases—Characterization by XPS", Journal of Physics and Chemistry of Solids, Apr. 2001, vol. 62(4), 811-817.
Nadeau, "Clay Particle Engineering: a Potential New Technology with Diverse Applications", Applied Clay Science, 1987, 2, 83-93.
Naguib et al, "New Two-dimensional Niobium and Vanadium Carbides as Promising Materials for Li-Ion Batteries", American Chemical Society, Oct. 2013, 135(43), 15966-15969.
Naguib et al, "Two-Dimensional Nanocrystals Produced by Exfoliation of $Ti_3AlC_2$", Advanced Materials, 2011, 23(37), 4248-4253.
Naguib et al, "Two-Dimensional Transition Metal Carbides", American Chemical Society, Feb. 2012, 6(2), 1322-1331.
Naguib, et al., "Mxene: A Promising Transition Metal Carbide Anode for Lithium-ion Batteries", Electrochemistry Communications, 2012, 16, 61-64.
Naguib, et al, Synthesis of a New Nanocrystalline Titanium Aluminum Fluoride Phase by Reaction of Ti2aic With Hydrofluoric Acid, RSC Adv., 2011, 1, 1493-1499.
Naguib, et al., "Mxenes: A New Family of Two-Dimensional Materials", Adv. Mater., Feb. 2014, vol. 26(7), 992-1005.
Peng, et al., "Unique Lead Adsorption Behavior of Activated Hydroxyl Group in Two-Dimensional Titanium Carbide", J. Am. Chem. Soc., Mar. 2014, 136(11), 4113-4116.
Rao, et al, "A Study of the Synthetic Methods and Properties of Graphenes", Science and Technology of Advanced Materials, Oct. 27, 2010, vol. 11, 1-15.
Savoskin, et al, "Carbon Nanoscrolls Produced From Acceptor-Type Graphite Intercalation Compounds", 2007, Carbon, 45, 2797-2800.
Schmidt, et al., "XPS Studies of Amino Acids Absorbed on Titanium Dioxide Surfaces", Fresenius Journal of Analytical Chemistry, May 1991, 341, 412-415.

(56) References Cited

OTHER PUBLICATIONS

Spanier, et al, "Vibrational Behavior of the Mn+1AXn phases from First-Order Raman Scattering, M=Ti,V,Cr, A=Si, X=C,N)", Physical Review B, Jan. 2005, 71, 1-4.

Stankovich, et al, "Graphene-based Composite Materials", Nature, Jul. 2006, 442, 282-286.

Su, et al, "High-Quality Thin Graphene Films from Fast Electrochemical Exfoliation", ACS Nano, 2011, 5(3), 2332-2339.

Tang, et al., "Are MXenes Promising Anode Materials for Li Ion Batteries? Computational Studies on Electronic Properties and Li Storage Capability of ThC2 and ThC2X2 (X=F, OH) Monolayer", J. Am. Chem. Soc., Sep. 2012, 134(40), 16909-16916.

Tran et al, "Lithium Intercalation in Porous Carbon Electrodes", Material Research Society 1995 Spring Meeting, San Francisco, CA, Apr. 17-21, 1995, 12 Pages.

Travaglini et al, "The Corrosion Behavior of Ti3SiC2 in Common Acids and Dilute NaOH", Corrosion Science, Jun. 1, 2003, 45(6), 1313-1327.

Tzenov et al, "Synthesis and Characterization of Ti3AlC2", Journal of the American Ceramic Society, Jan. 1, 2000, 83(4), 825-832.

Viculis et al, "A Chemical Route to Carbon Nanoscrolls", Science, Feb. 28, 2003, 299, p. 1361.

Viculis, et al., "Intercalation and Exfoliation Routes to Graphite Nanoplatelets", Journal of Materials Chemistry, 2005, vol. 15, 974-978.

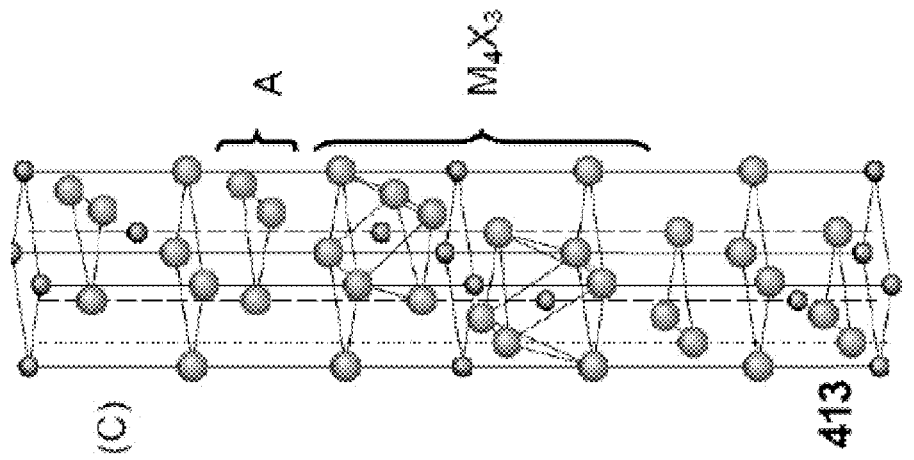
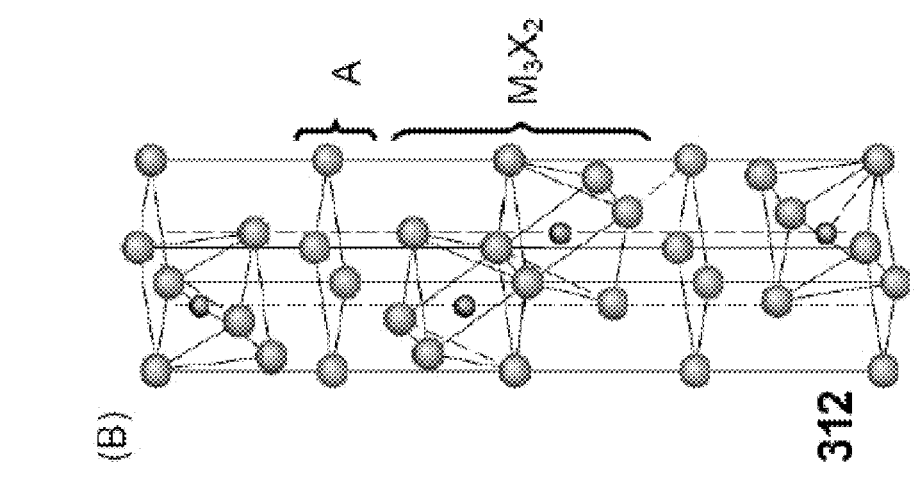
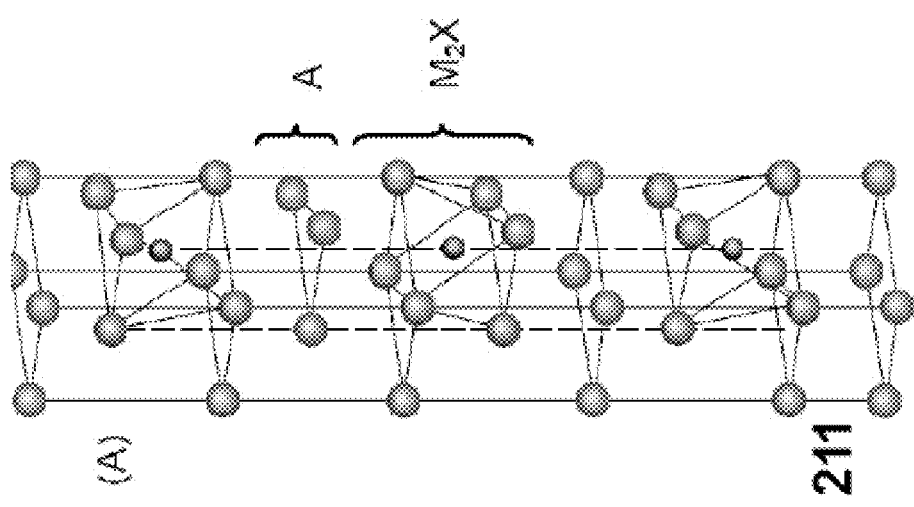

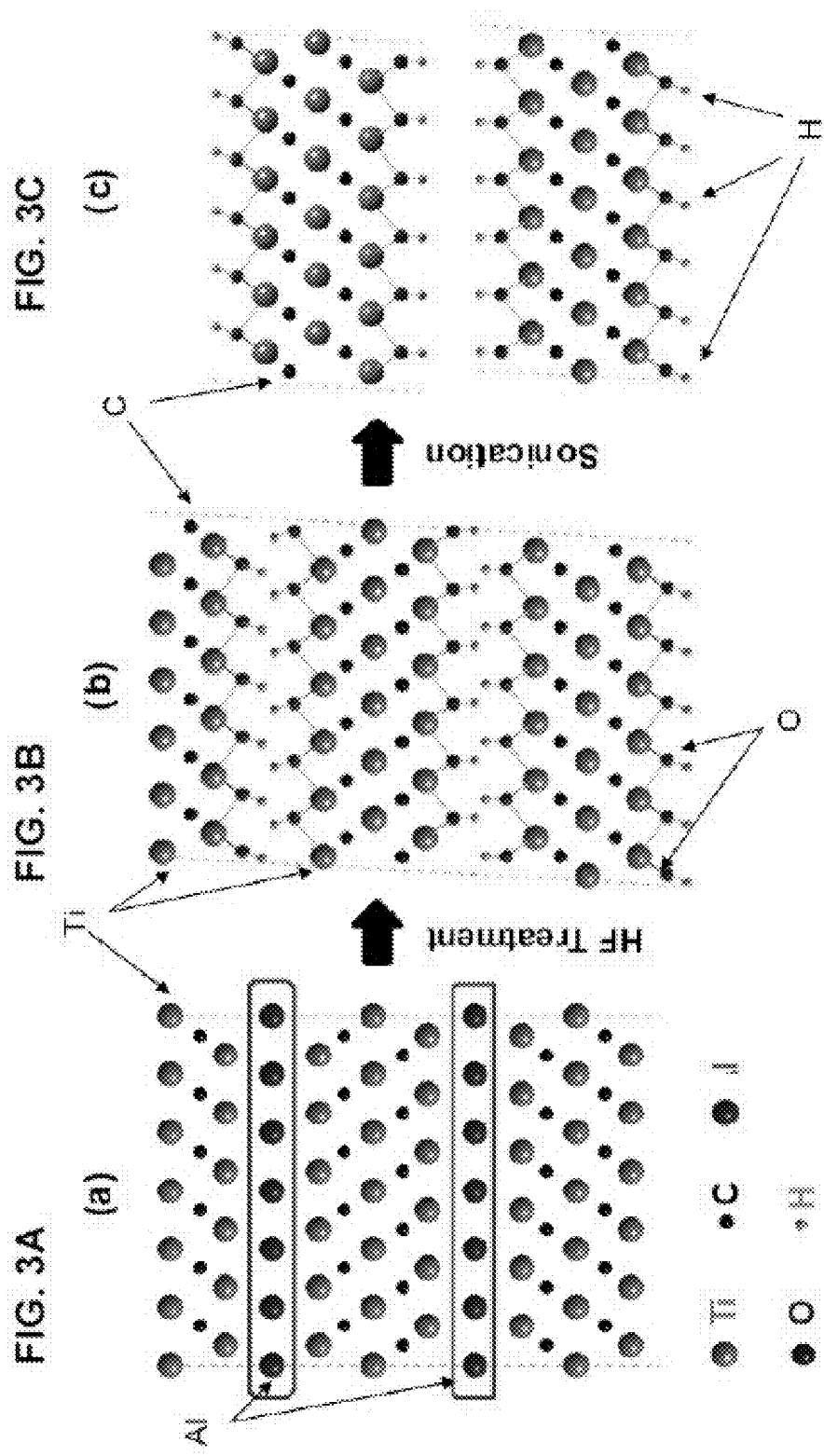

FIG. 14  $(V_{0.5}Cr_{0.5})_3AlC_2$ HF 50% 69 hrs at RT

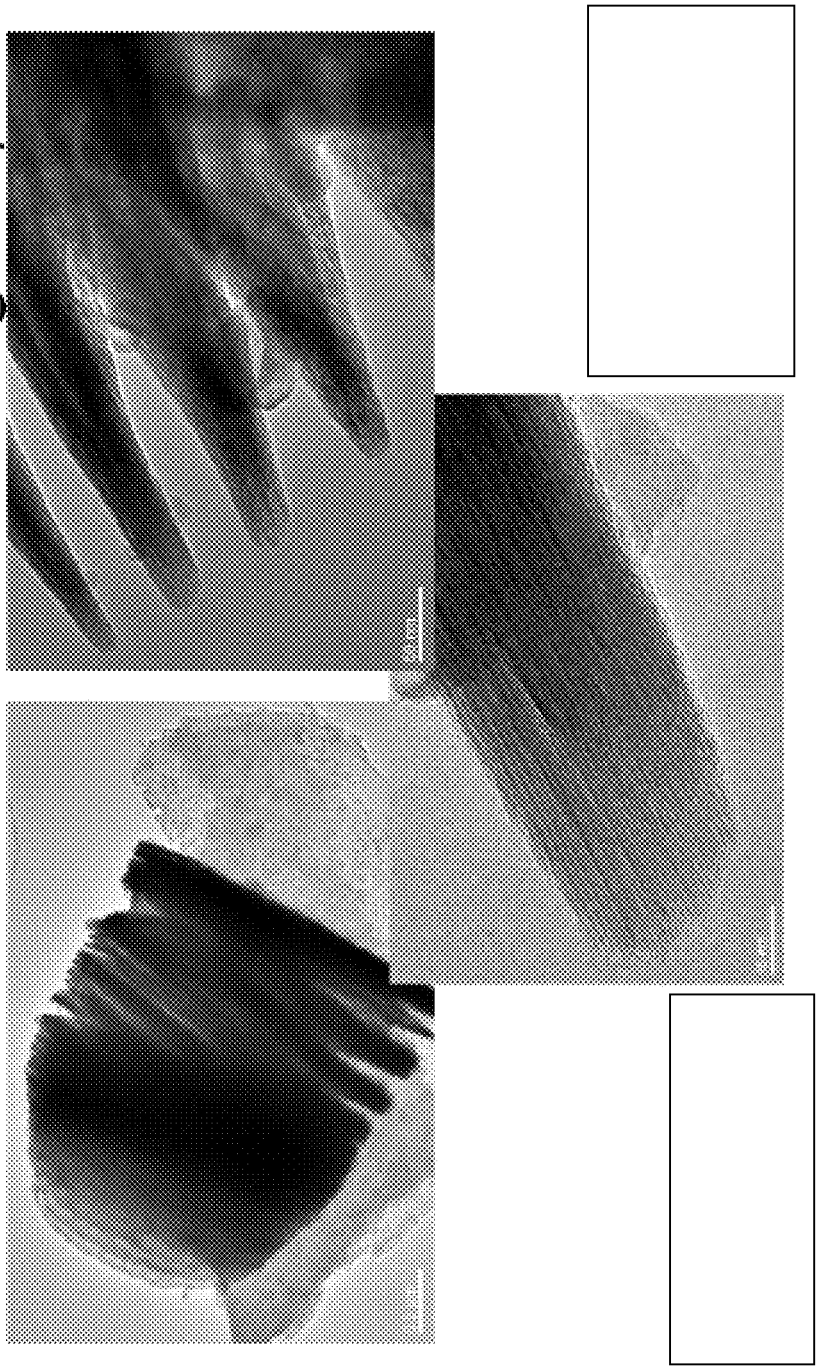
FIG. 18A TEM graph of $Ti_3C_2$ (exfoliation of $Ti_3AlC_2$ with 50% solution of HF during 22h)

FIG. 21

Resistivity

| Parameters | TLAK + 50% HF, at ambient temperature | | | | |
|---|---|---|---|---|---|
| | 2h | 6h | 10h | 15h | 19h |
| Resistance, Ω | 8.2 | 7.3 | 8.5 | 12.0 | 13.0 |
| | 7.2 | 7.5 | 8.9 | 11.7 | 14.9 |
| | 7.2 | 8.8 | 8.1 | 11.9 | 14.5 |
| | 6.1 | 8.7 | 7.3 | 13.7 | 12.5 |
| | 7.0 | 8.6 | 7.8 | 12.9 | 12.2 |
| | 7.1 | 9.4 | 7.5 | 13.5 | 17.4 |
| Resistance (average), Ω | 7.1 | 8.4 | 8.0 | 12.6 | 14.1 |
| Resistivity, Ω/☐ | 32.3 | 38.0 | 36.3 | 57.2 | 63.8 |

*Assumption*: we have infinite sheet

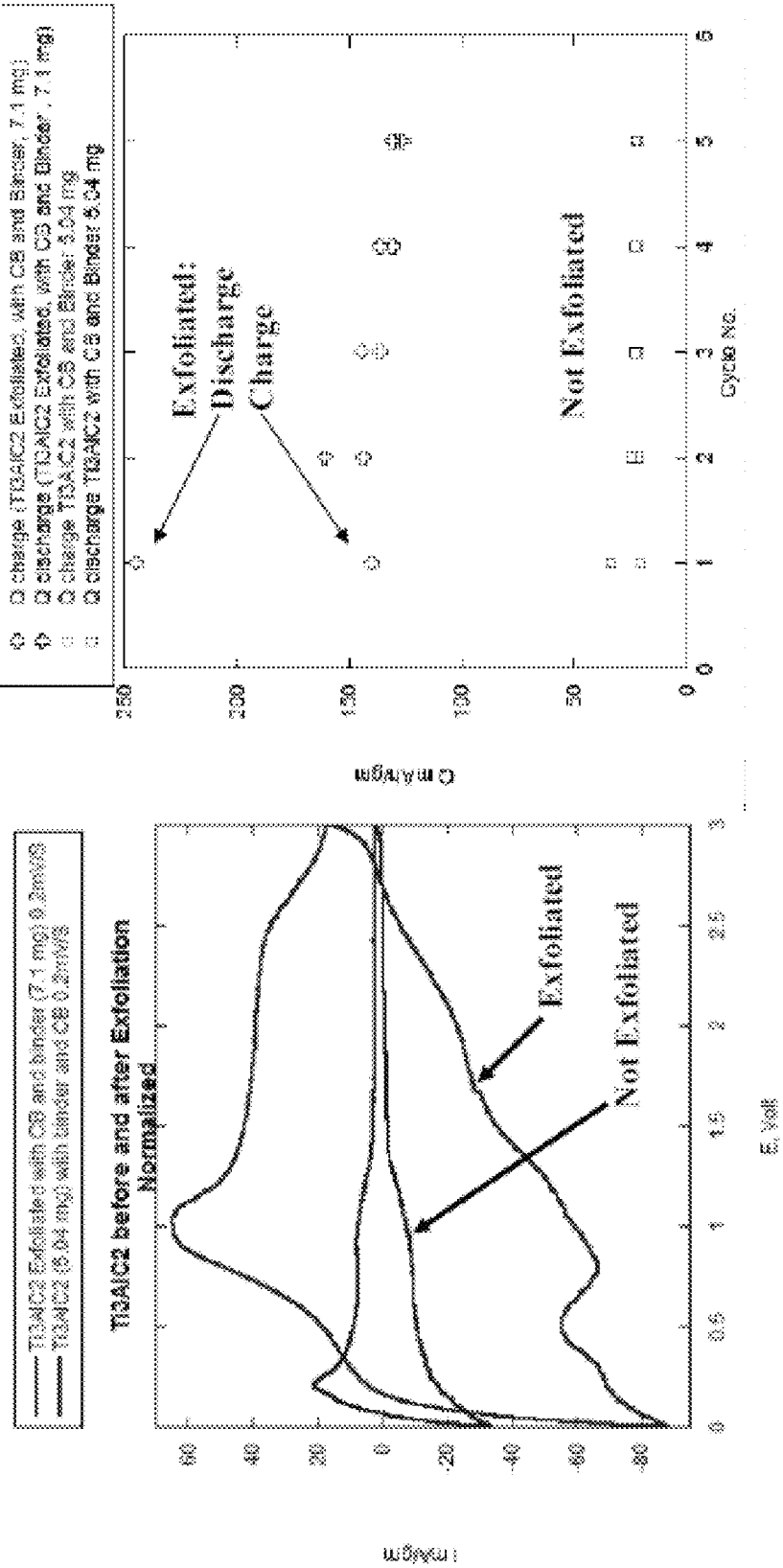
FIG. 29(A) MXene: with binder and CB Capacity compared to $Ti_3AlC_2$ with binder and CB

MXene : with binder and CB Capacity compared to $Ti_3AlC_2$ with binder and CB and compared to exfoliated without CB

- Difference between Exfoliated with and without CB:
  - 50 mAh/gm in 1st discharging cycle
  - 100 mAh/gm in the 2nd discharging cycle
- Can not be CB capacity, should be conductivity problem Upper curve of (b) refers to absorption; lower curve refers to desorption

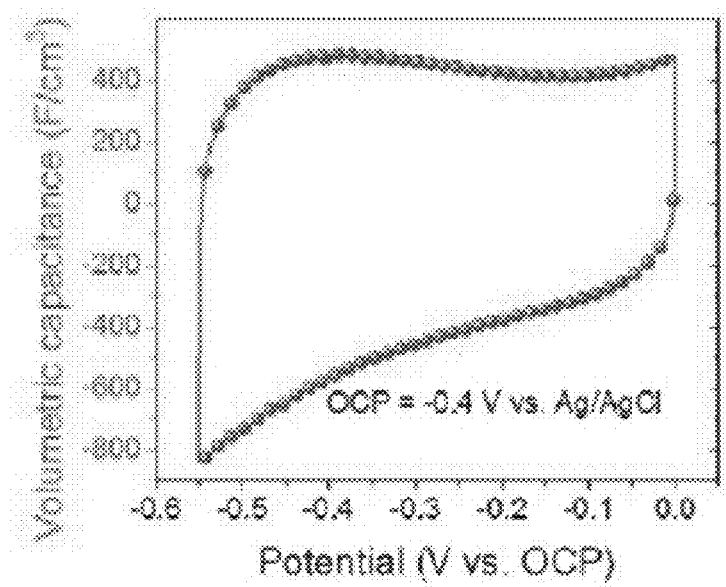
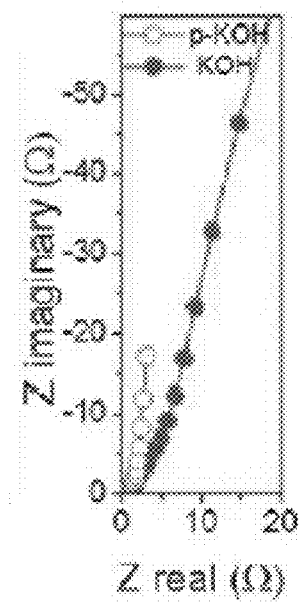
FIG. 42A
FIG. 42B
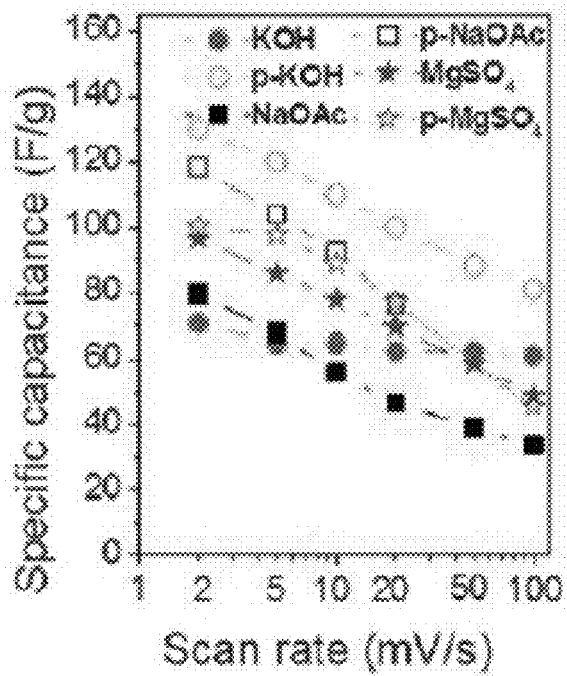
FIG. 42C

FIG. 53E
FIG. 53F
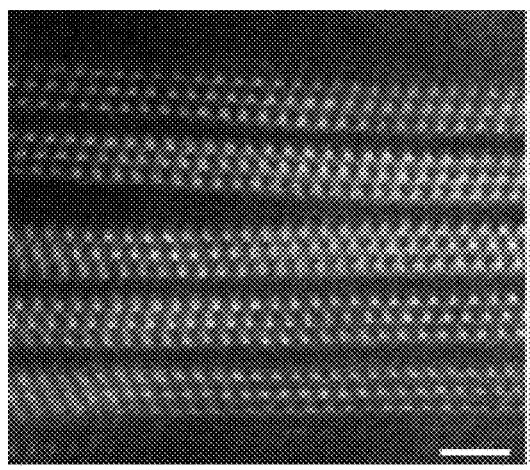
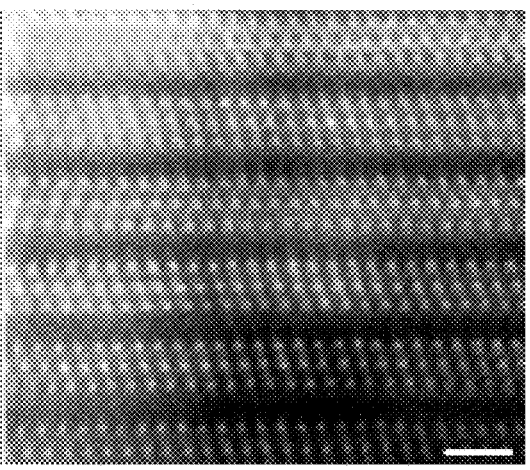
FIG. 54A
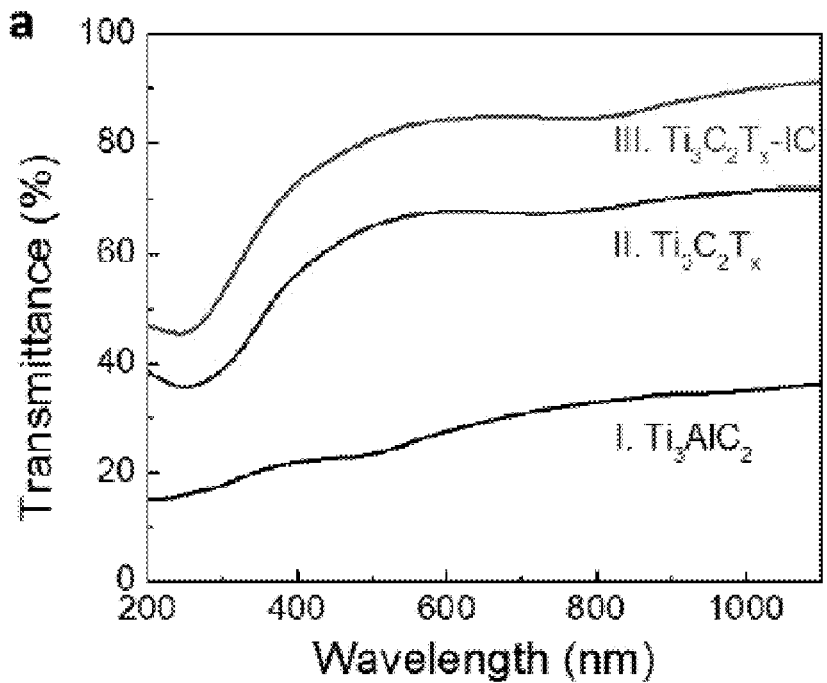

COMPOSITIONS COMPRISING FREE-STANDING TWO-DIMENSIONAL NANOCRYSTALS

CROSS REFERENCE TO RELATED APPLICATIONS

This application is a continuation of U.S. patent application Ser. No. 14/094,966, filed Dec. 3, 2013, which is a continuation-in-part of PCT/US2012/043273, filed Jun. 20, 2012, which claims priority to U.S. Provisional Application Ser. Nos. 61/499,318; 61/521,428; and 61/587,172, filed Jun. 21, 2011, Aug. 9, 2011, and Jan. 17, 2012, respectively. U.S. patent application Ser. No. 14/094,966 also claims the benefit of priority to U.S. Provisional Application Ser. No. 61/733,015, filed Dec. 4, 2012. The subject matter of each of these applications is incorporated by reference herein in its entirety for all purposes.

GOVERNMENT INTERESTS

This invention was made with government support under a grant from the U.S. Department of Energy under Contract No. DE-ACO2-05CH11231, Subcontract 6951370. The government has certain rights in the invention.

TECHNICAL FIELD

The present invention is directed to compositions comprising free standing two dimensional crystalline solids, and methods of making the same.

BACKGROUND

Typically, two-dimensional, 2-D, free-standing crystals exhibit properties that differ from those of their three-dimensional, 3-D, counterparts. Currently, however, there are relatively few materials which can be described as 2-D, atomically-scaled layered solids. Clearly the most studied freestanding 2-D material is graphene, but other materials include hexagonal BN, certain transition metal oxides, hydroxides, and silicates, including clays, $S_2N$, $MoS_2$ and $WS_2$ are also known. Currently, the number of non-oxide materials that have been exfoliated is limited to two fairly small groups, viz. hexagonal, van der Waals bonded structures (e.g. graphene and BN) and layered metal chalcogenides (e.g. $MoS_2$, $WS_2$, etc.).

Although graphene has attracted more attention than all other 2-D materials together, its simple chemistry and the weak van der Waals bonding between layers in multi-layer structures limit its use. Given the properties of graphene for applications ranging from composite reinforcement to electronics, there is interest in other new materials which may also be described as 2-D, atomically-scaled layered solids.

SUMMARY

This invention is directed to compositions comprising free standing and stacked assemblies of two dimensional crystalline solids, and methods of making the same.

Various embodiments of this invention provide compositions comprising at least one layer having first and second surfaces, each layer comprising:
a substantially two-dimensional array of crystal cells,
each crystal cell having an empirical formula of $M_{n+1}X_n$, such that each X is positioned within an octahedral array of M,
wherein M is at least one Group IIIB, IVB, VB, or VIB metal;
wherein each X is C and/or N (i.e., stoichiometrically $X = C_xN_y$, including where $x+y=1$); and
$n = 1, 2,$ or 3.

Various embodiments provide for compositions composed of individual or a plurality of such layers.

Other embodiments provide that at least one of the surfaces is coated with a coating comprising alkoxide, carboxylate, halide, hydroxide, oxide, sub-oxide, nitride, sub-nitride, sulfide, thiol, or a combination thereof.

Still further embodiments provide polymer composites comprising an organic polymer and at least one composition described in the preceding paragraphs.

Certain embodiments provide for at least one stacked assembly of at least two layers having first and second surfaces, each layer comprising:
a substantially two-dimensional array of crystal cells, each crystal cell having the empirical formula of $M_{n+1}X_n$, such that each X is positioned within an octahedral array of M;
wherein M is a Group IIIB, IVB, VB, or VIB metal;
each X is C and/or N (i.e., stoichiometrically $X = C_xN_y$, including where $x+y=1$); and $n = 1, 2,$ or 3;
wherein the layers are characterized as having an average surface area and interlayer distance.

In other embodiments, at least one of the surfaces of the layers within a stacked assembly has bound thereto alkoxide, carboxylate, halide, hydroxide, oxide, sub-oxide, nitride, sub-nitride, sulfide, thiol, or a combination thereof In some embodiments, the stacked assemblies described in the preceding paragraphs are capable of, or have atoms or ions, that are intercalated between at least some of the layers. In other embodiments, these atoms or ions are lithium. In still other embodiments, these structures are part of an energy storing device or a battery.

This invention also describes methods of preparing compositions comprising:
removing substantially all of the A atoms from a MAX-phase composition having an empirical formula of $M_{n+1}AX_n$.
wherein M is at least one Group IIIB, IVB, VB, or VIB metal,
wherein A is an A-group element;
each X is C and/or N (i.e., stoichiometrically $X = C_xN_y$, including where $x+y=1$); and
$n = 1, 2,$ or 3,
thereby providing a composition comprising at least one layer having a first and second surface, each layer comprising a substantially two-dimensional array of crystal cells.

BRIEF DESCRIPTION OF THE DRAWINGS

The following figures are presented as illustrative examples, and should not be considered to limit the scope of the invention in any way. Except where otherwise noted, the scales of the figures may be exaggerated for illustrative purposes.

FIGS. 1A-C illustrate indicative crystal structures of the MAX phases in which the transitional metal carbide or nitride ($M_{n+1}X_n$) layers are interleaved with layers of pure A-group element. FIG. 1A illustrates the configuration of the $M_2X$ framework within the 211 class of MAX phase compounds, wherein every third layer is A-group. FIG. 1B illustrates the configuration of the $M_3X_2$ framework within the 312 class of MAX phase compounds, wherein every fourth layer is A-group. FIG. 1C illustrates the configuration of the $M_4X_3$ framework within the 413 class of MAX phase compounds, wherein every fifth layer is A-group.

FIGS. 3A-C illustrate a schematic representation of the exfoliation process for $Ti_3AlC_2$. FIG. 3A provides the $Ti_3AlC_2$ structure. FIG. 3B diagrammatically illustrates a structure where the Al atoms have been replaced by OH after reaction with HF. FIG. 3C illustrates a structure resulting from the subsequent breakage of the hydrogen bonds and separation of nano-sheets after sonication in methanol.

FIG. 18(a/b) shows TEM micrographs of chemically exfoliated $Ti_3AlC_2$ (50% HF 22 hours at RT).

FIG. 21 shows resistivity for various chemically exfoliated $Ti_3AlC_2$, generated as a function of time, in 50% HF at ambient temperature.

FIG. 33A for compounds which form basic solutions when dissolved in water, FIG. 33B for sulfate salts which form nearly neutral solutions when dissolved in water and, FIG. 33C for Na-salts with different organic anions. In all figures the location of the $Ti_3C_2T_s$ peak before immersion in the salt solutions is depicted by dashed vertical line. In all cases, the c-lattice parameter increases by the values shown and ranged from a high of 5 Å to a low of 0.7 Å.

FIG. 35A shows profiles in NaOH-, KOH-, and LiOH-containing solutions at 20 mV/s. FIG. 35B shows the CV profiles in $K_2SO_4$, $Al_2(SO_4)_3$, and $Al(NO_3)_3$ solutions at 20 mV/s. FIG. 35C provides a summary of rate performances in different aqueous electrolytes.

FIG. 40A shows $Ti_3C_2T_s$ in 1 M KOH solution; FIG. 40B shows $Ti_3C_2T_s$ in 1 M $MgSO_4$ solution. Vertical dashed lines indicate the original position of the (0002) peak of the $Ti_3C_2T_s$ electrodes before mounting in a cell. Inclined arrows show the direction of the (0002) peak shift. Insets illustrate cycling direction and concomitant changes in the c lattice parameters during cycling. In both KOH and $MgSO_4$ electrolytes, shrinkage during cathodic polarization was observed.

FIG. 42A shows cyclic voltammetry data of $Ti_3C_2T_s$ paper in KOH electrolyte. FIG. 42B shows EIS data in KOH for $Ti_3C_2T_s$ electrode (KOH, solid symbols) and $Ti_3C_2T_s$ paper (p-KOH). FIG. 42C shows rate performance of the $Ti_3C_2T_s$ paper (open symbols) versus multilayer exfoliated $Ti_3C_2T_s$ electrode (solid symbols) in KOH-, $MgSO_4$-, and NaOAc-containing electrolytes.

FIG. 43A shows a cyclic voltammogram in 1M $MgSO_4$ electrolyte. Capacitance retention test of MXene paper in 1 M $MgSO_4$ are provided in FIG. 43B and 3 M NaOAc (FIG. 43C) Insets in FIG. 43B and FIG. 43C show resuts of galvanostatic cycling data of $Ti_3C_2T_s$ paper in $MgSO_4$ and NaOAc, respectively.

FIG. 44A shows cyclic voltammetry data at different scan rates; FIG. 44B shows capacitance retention test. Inset: gavlanostatic cycling data collected at 1 A/g.

FIG. 45A shows a schematic representation of the synthesis and intercalation of MXene. To produce MXene, the Al layer was removed from the corresponding MAX phase in aqueous HF solution resulting in OH terminated MXene layers. Then MXene was treated with an intercalant (urea is shown here as an example) yielding MXene intercalation compound. FIG. 45B, XRD patterns of MXene: (i) as-received, before any treatment, (ii) after HM treatment, and then washed with ethanol, and (iii) after HM in DMF treatment, washed with DMF, dried at different conditions: a whole range diffractograms. FIG. 45C is an expanded image of FIG. 45B but zoomed on the (002) peak in 5-12° 2θ range. Intercalation was performed at 80° C. for 24 h. The MXene powder used for intercalation was dried at 100° C. for 22 h. See Example 14.

FIG. 51A is a cartoon representation of magnetron sputtering of Ti, Al and C forming a few-nanometer TiC incubation layer on a 0001 sapphire substrate, followed by the deposition of $Ti_3AlC_2$.

FIG. 52A provides XRD patterns of as-deposited—60 nm nominal thickness—$Ti_3AlC_2$ thin films (I), $Ti_3C_2T_s$ after etching in 50% HF for 2 h 40 min (II), and $Ti_3C_2T_s$-IC after etching in 1M $NH_4HF_2$ for 11 h (III). XPS spectra of, Ti 2p (FIG. 52B), C is (FIG. 52C), and Al 2p (FIG. 52D), for $Ti_3AlC_2$, $Ti_3C_2T_s$ and $Ti_3C_2T_s$—IC thin films, respectively. The vertical lines in b and c indicates the positions of Ti (3/2p and 1/2p) and C (1s) binding energies in TiC, respectively. FIG. 52E provides deconvolution of high resolution XPS spectra for N is region for $Ti_3C_2T_s$-IC, best fitted by symmetric Gaussian-Lorentzian curves resting on a Shirley background. The two components correspond to ($NH_4^{+1}$) and ($NH_3$).

FIG. 53A-F shows cross-sectional STEM images of $Ti_3AlC_2$ films before and after etching. STEM images of $Ti_3AlC_2$ (FIG. 53A), $Ti_3C_2T_s$, (FIG. 53B) and $Ti_3C_2T_s$-IC films (FIG. 53C) (60 nm nominal thickness) grown on a sapphire substrate with a TiC incubation layer. Insets show SAED of the film and the substrate. The subscripts A and T correspond to $Al_2O_3$ and $Ti_3AlC_2$, respectively. High-resolution STEM images of $Ti_3AlC_2$ (FIG. 53D), $Ti_3C_2T_s$ (FIG. 53E), and $Ti_3C_2T_s$-IC films (FIG. 53F), along the [11$\bar{2}$0] zone axis. Scale bars for low resolution (FIGS. 55A-C), and high-resolution (FIGS. 53D-F) images correspond to 5 nm and 1 nm, respectively.

FIG. 54A-B illustrate the optical behavior of non-etched and etched $Ti_3AlC_2$ thin films; FIG. 54A provides transmittance spectra and visual image (on right) for, (I) $Ti_3AlC_2$, (II) $Ti_3C_2T_s$ and (III) $Ti_3C_2T_s$-IC films of 15 nm nominal thickness. The film are ca. 1×1 cm² in area; FIG. 54B provides light absorbance at wavelengths of 240 and 800 nm vs. thickness of $Ti_3C_2T_s$ and $Ti_3C_2T_s$-IC films.

FIG. 55A provides data for resistivity vs. temperature for $Ti_3AlC_2$, $Ti_3C_2T_s$ and $Ti_3C_2$—IC films of 20 nm nominal thickness. FIG. 55B provides data for resistivity vs. temperature for $Ti_3C_2T_s$ of 20 nm nominal thickness. Inset shows fitting of resistivity, over the temperature range of 2 to 74 K, to the weak localization model ($\rho \sim \ln T$) and, FIG. 55C compares normalized magnetoresistance curves for $Ti_3C_2T_s$ of 28 nm nominal thickness at various temperatures ranging from 2.5 to 200 K. RH=0 refers to the film resistance in the absence of applied magnetic field.

DETAILED DESCRIPTION OF ILLUSTRATIVE EMBODIMENTS

Figure 2B:
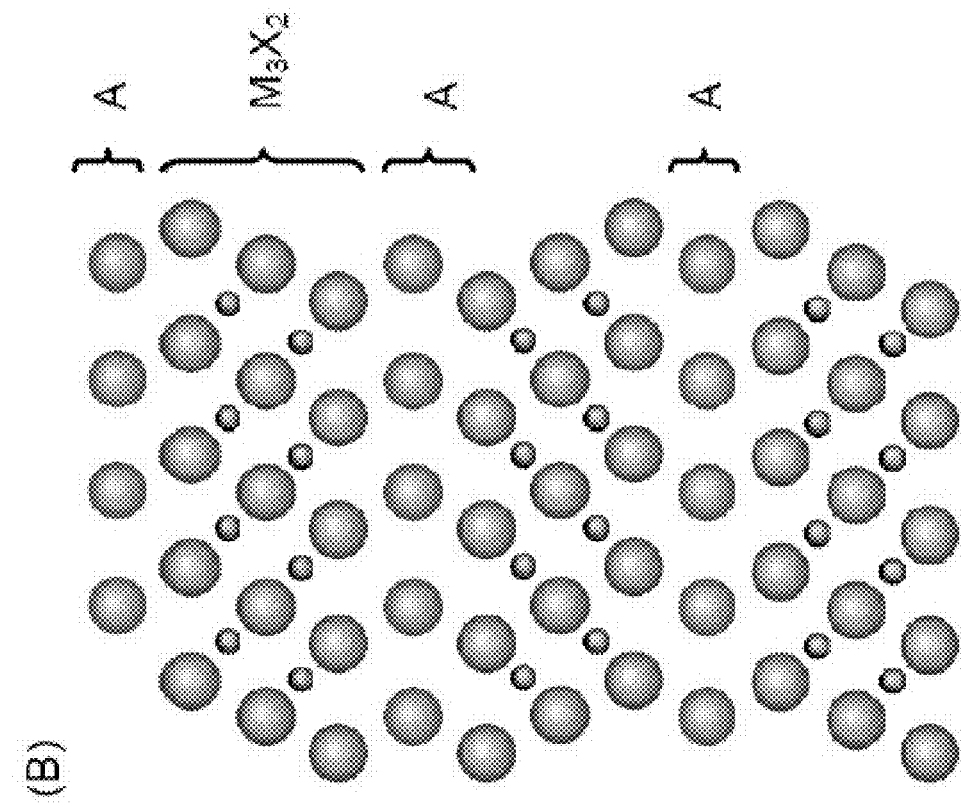
FIGS. 2A-B provide a 3-dimensional (FIG. 2A) and 2-dimensional (FIG. 2B) representation of the crystal structure of the 312 class of compounds

The present invention may be understood more readily by reference to the following detailed description taken in connection with the accompanying Figures and Examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to compositions and to the articles and devices derived therefrom, as well as the methods of manufacture and use.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When values are expressed as approximations by use of the antecedent "about," it will be understood that the particular value forms another embodiment. In general, use of the term "about" indicates approximations that can vary depending on the desired properties sought to be obtained by the disclosed subject matter and is to be interpreted in the specific context in which it is used, based on its function, and the person skilled in the art will be able to interpret it as such. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, reference to values stated in ranges includes each and every value within that range.

It is to be appreciated that certain features of the invention which, for clarity, described herein in the context of separate embodiments, may also be provided in combination in a single embodiment. Conversely, various features of the invention that are, for brevity, described in the context of a single embodiment, may also be provided separately or in any subcombination. Finally, while an embodiment may be described as part of a series of steps or part of a more general composition or structure, each said step may also be considered an independent embodiment in itself.

Various embodiments of this invention provide for crystalline compositions comprising at least one layer having first and second surfaces, each layer comprising a substantially two-dimensional array of crystal cells; each crystal cell is an ordered array of atoms having an empirical formula of $M_{n+1}X_n$, such that each X is positioned within an octahedral array of M; wherein M is at least one Group IIIB, IVB, VB, or VIB metal; wherein each X is C or N (i.e., stoichiometrically $X=C_xN_y$, including where x+y=1); and n=1, 2, or 3. In some embodiments, these compositions comprise a plurality of layers. Other embodiments provide for stacked assemblies of such layers. Collectively, such compositions are referred to herein as "MXene," "MXene compositions," or "MXene materials." Additionally, these terms "MXene," "MXene compositions," or "MXene materials" also refer to those compositions derived by the chemical exfoliation of MAX phase materials, whether these compositions are present as free-standing 2-dimensional or stacked assemblies (as described further below). FIG. 1 provides a representation of the crystal cells of various $M_{n+1}X_n$ (where n=1, 2, or 3) frameworks, presented however, in the context of corresponding MAX-phase materials (see also below). In various embodiments, each X is positioned within an octahedral array of M.

Figure 2A:
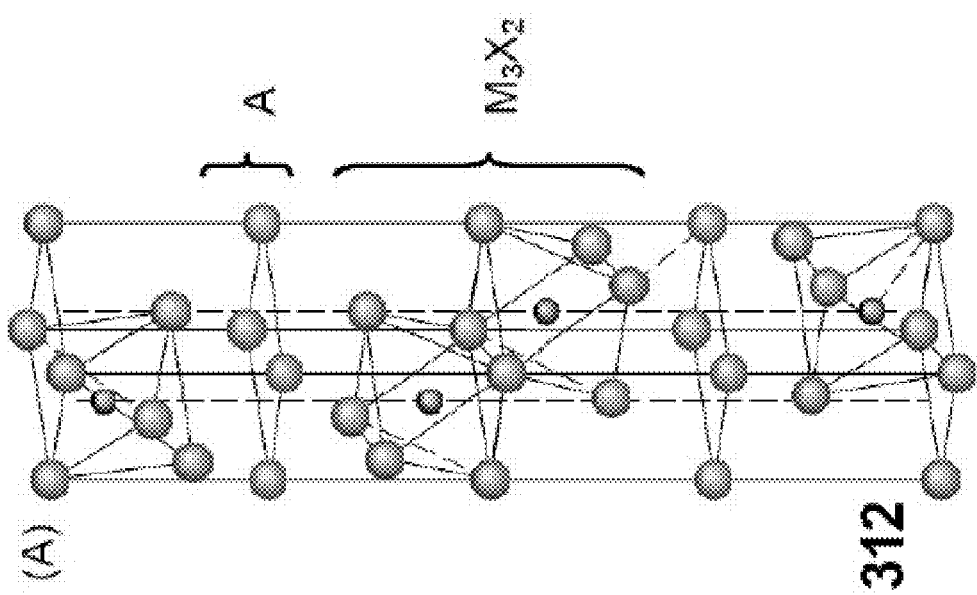

Analogous to other so-called two-dimensional, atomically-scaled layered solid materials, such as graphene or hexagonal BN, these MXene crystalline compositions may be free-standing or be present in stacked compositions. As used herein, the term "free standing" refers to individual layers wherein the adjacent composite crystal layers are not bonded to one another by covalent bonds or connected by metal-lattice bonds, but may be joined by intervening hydrogen (or even weaker) bonding, such that each such layer can be physically manipulated. See e.g., FIGS. 2 and 3. However, this term does not preclude the deposition of these layers or stacked layers on substrates or within polymer compositions (see also below).

The term "crystalline compositions comprising at least one layer having first and second surfaces, each layer comprising a substantially two-dimensional array of crystal cells" refers to the unique character of these materials. For purposes of visualization, the two-dimensional array of crystal cells may be viewed as an array of cells extending in an x-y plane, with the z-axis defining the thickness of the composition, without any restrictions as to the absolute orientation of that plane or axes. It is preferred that the at least one layer having first and second surface contain but a single two-dimensional array of crystal cells (that is, the z-dimension is defined by the dimension of approximately one crystal cell), such that the planar surfaces of said cell array defines the surface of the layer, it should be appreciated that real compositions may contain portions having more than single crystal cell thicknesses.

That is, as used herein, "a substantially two dimensional array of crystal cells" refers to an array which preferably includes a lateral (in x-y dimension) array of crystals having a thickness of a single cell (e.g., corresponding to the $M_2X$, $M_3X_2$, or $M_4X_3$ cells as depicted in FIG. 1), such that the top and bottom surfaces of the array are available for chemical modification.

It should also be appreciated that, analogous to graphene or hexagonal BN compositions, this description of a planar or two-dimensional array should not be interpreted to describe a necessarily flat structure; rather such compositions may also take the form of a curved or undulating plane, a scroll, or a cylinder or tube (e.g., analogous to the structure of a carbon or BN nanotube).

In certain embodiments, the compositions may contain C or N atoms, or a mixture thereof, but in any case, these atoms are positioned within an octahedral or pseudo-octahedral array of M atoms, reminiscent of the positioning of the carbon or nitrogen atom within MAX-phase materials. While not necessarily being bound to the scientific accuracy of this statement, this arrangement appears to protect the C and/or N atoms from external chemical attack, while at the same time providing a degree of structural strength to the 2-dimensional layers.

Given the difficulties in obtaining crystallographic evidence as to the crystallinity of materials having such few layers (e.g., less than about 5 cell layers), owing to the reduced level or lack of constructive interference of such few layers, these materials may be characterized by measuring the thickness of the individual layers (measured, for example, by Transmission Electron Micrography or atomic force microscopy). Depending on the particular empirical formula of the given material, the thickness of a given single cell layer will be on the order of about 0.2 to about 0.3 nm (preferably about 0.25 nm) for $M_2X$ compositions, about 0.3 to about 0.7 nm (preferably about 0.5 nm) for $M_3X_2$ compositions, and about 0.6 to about 0.9 nm (preferably about 0.75 nm) for $M_4X_3$ compositions. As described more fully below, one method of preparing these compositions is to react a precursor MAX phase material so as to remove the labile A-phase, and exfoliating the resulting structure. In these cases, it is so generally observed that the crystallinity of the resulting MXene framework, which existed in the original MAX phase structure, is sufficiently robust as to be retained during the preparation process, so that the thickness measurements by themselves can be used to characterize the materials, even in the absence of crystallographic analysis.

Figure 7:
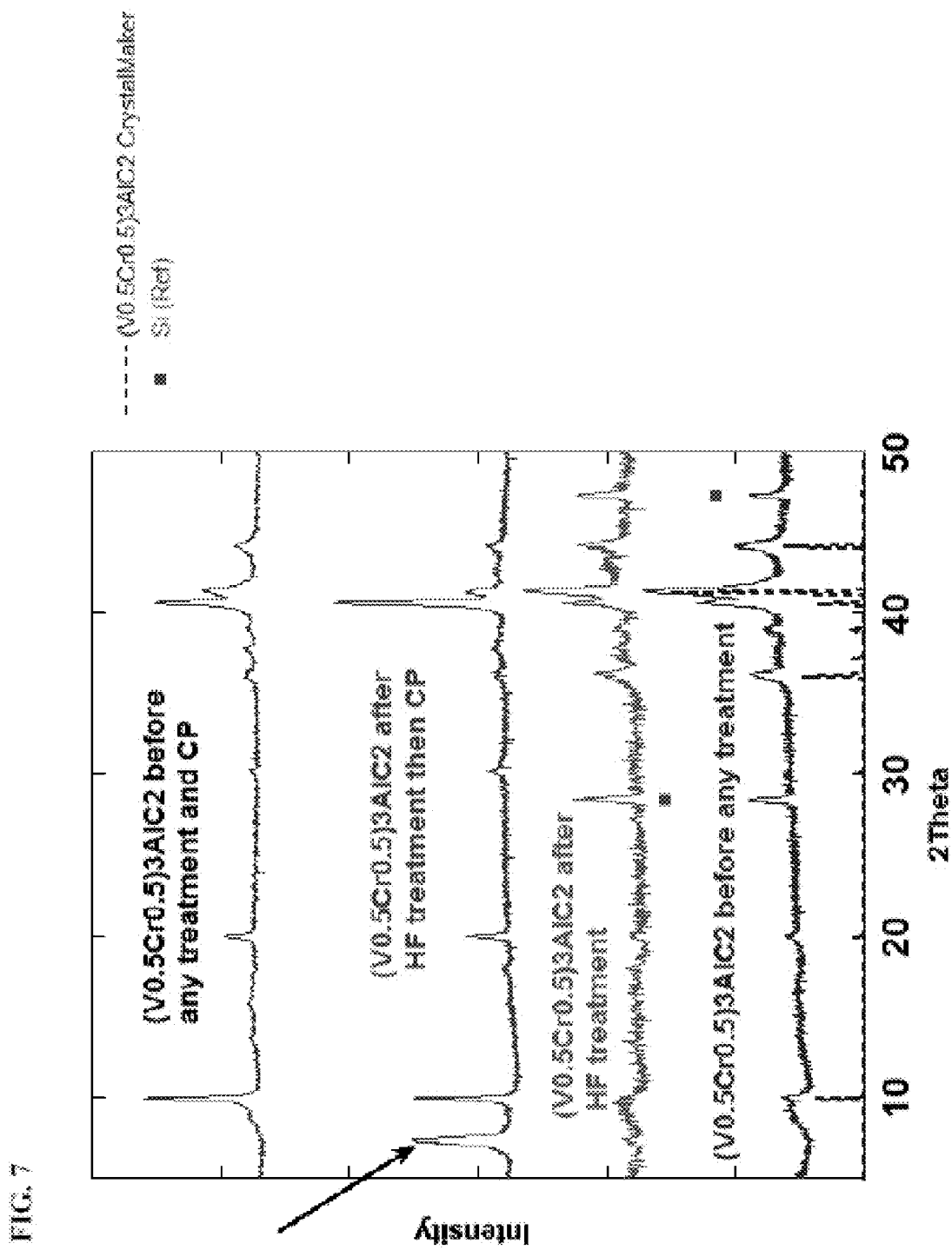
FIG. 7 provides X-ray diffraction patterns of $(V_{1/2}Cr_{1/2})_3AlC_2$ before and after exfoliation. From the bottom up, FIG. 7 provides a simulated XRD pattern for $(V_{1/2}Cr_{1/2})_3AlC_2$ as determined by CrystalMaker software, and measured XRD patterns for powdered $(V_{1/2}Cr_{1/2})_3AlC_2$ before any treatment, $(V_{1/2}Cr_{1/2})_3AlC_2$ after HF treatment, $(V_{1/2}Cr_{1/2})_3AlC_2$ after HF treatment and cold pressing (CP), and $(V_{1/2}Cr_{1/2})_3AlC_2$ before any treatment or cold pressing. The peak at 2θ=7.3° appears only after HF treatment and cold pressing. By analogy to the results shown for $Ti_3AlC_2$, this peak is attributed to $(V_{1/2}Cr_{1/2})_3C_2$. See Example 5.

These MXene materials (even individual or exfoliated layers) can also be characterized by measuring the X-ray diffraction (XRD) spectra of (optionally cold pressed) stacked layers (see, e.g., Example 2, FIG. 4(a) and Example 4, FIG. 7 below). That is, such stacking provides a sample of sufficient thickness (number of layers) to allow for sufficient constructive interference so as to provide for a measurable XRD pattern to be obtained. One distinguishing feature of XRD patterns thus generated is the presence of peaks at 2θ of ca. 5-7° (i.e., between about 4.5° and about 9.5° when Cu $K_\alpha$ radiation is used), corresponding to the d-spacing (thickness) of the individual layers (including the surface coatings of each layer) and lower than the (002) peaks of the corresponding MAX phase materials. That this MXene peak occurs at lower 2θ values, reflecting higher d-spacings of the layers, than the corresponding (002) plane in a corresponding MAX phase material is consistent with the greater spacing of the crystal cells of the two materials in the former relative to the latter (e.g., referring to FIG. 3, the individual layers of the $Ti_3C_2$ in FIG. 3(b) are spaced further apart than the corresponding layers in FIG. 3(a)).

As described herein, the terms "M" or "M atoms," "M elements," or "M metals" refers to one or more members of the Groups IIIB, IVB, VB, or VIB or (aka) Groups 3-6 of the periodic table, either alone or in combination, said members including Sc, Y, Lu, Ti, Zr, Hf, V, Nb, Ta, Cr, Mo, and W. The terms "M" or "M atoms," "M elements," or "M metals" may also include Mn. In preferred embodiments, the transition metal is one or more of Sc, Ti, Zr, Hf, V, Nb, Ta, Cr, and/or Mo. In other preferred embodiments, the transition metal is one or more of Ti, Zr, V, Cr, Mo, Nb, and/or Ta. In even more preferred embodiments, the transition metal is Ti, Ta, Mo, Nb, V, and/or Cr.

The empirical formula $M_{n+1}X_n$, wherein X is C, N, or a combination thereof, and n=1, 2, or 3 gives rise to a number of possible composition. For example, and while not intending to be limited to this list, exemplary compositions when n=1 includes those wherein the empirical formula of the crystalline phase is $Sc_2C$, $Sc_2N$, $Ti_2C$, $Ti_2N$, $Mo_2C$, $V_2C$, $V_2N$, $Cr_2C$, $Cr_2N$, $Zr_2C$, $Zr_2N$, $Nb_2C$, $Nb_2N$, $Hf_2C$, and $Hf_2N$. Similarly, non-limiting exemplary compositions when n=2 includes those wherein the empirical formula of the crystalline phase is $Ti_3C_2$, $Ti_3N_2$, $V_3C_2$, $V_3C_2$, $Ta_3C_2$, and $Ta_3N_2$ and when n=3 includes those wherein the empirical formula is $Ti_4C_3$, $Ti_4N_3$, $V_4C_3$, $V_4N_3$, $Ta_4C_3$ and $Ta_4N_3$. Especially important independent embodiments include those where M comprises at least one Group IVB element, for example Ti, Zr, or Hf and those where M comprises at least one Group V elements, for example V, Nb, or Ta. More preferred independent embodiments include those where M is Ti or Ta, especially structures wherein the empirical formula of the crystalline phase is $Ti_2C$, $Ti_2N$, $Ti_3C_2$, $Ti_3N_2$, $Ti_4C_3$, or $Ti_4N_3$, or $Ta_3C_2$, $Ta_3N_2$, $Ta_4C_3$ or $Ta_4N_3$, especially $Ti_2C$ or $Ta_4C_3$ The range of compositions available can be seen as extending even further when one considers that each M-atom position within the overall $M_{n+1}X_n$ matrix can be represented by more than one element. That is, one or more type of M-atom can occupy each M-positions within the respective matrices. In certain exemplary non-limiting examples, these can be $(M^A_xM^B_y)_2C$ or $(M^A_xM^B_y)_2N$, $(M^A_xM^B_y)_3C_2$ or $(M^A_xM^B_y)_3C_2$, or $(M^A_xM^B_y)_4C_3$ or $(M^A_xM^B_y)_4C_3$, where $M^A$ and $M^B$ are independently members of the same group, and x+y=1. For example, in but one non-limiting example, such a composition can be $(V_{1/2}Cr_{1/2})_3C_2$. In the same way, one or more type of X-atom can occupy each X-position within the matrices, for example solid solutions of the formulae $M_{n+1}(C_xN_y)_n$, or $(M^A_xM^B_y)_{n+1}(C_xN_y)_n$.

In various embodiments, the composition's layer has first and second surfaces which are capable of being physically or chemically interrogated or modified. This feature distinguishes these compositions from sputtered matrices or so-called MAX phase compositions. While it may be possible to describe sputtered matrices or MAX phase compositions as containing two-dimensional arrays of crystal cells, in each case these are embedded within vertically integrated and practically bound to other layers within the respective matrices (e.g., in the case of sputtered matrices, to other neighboring sputtered layers or the substrate; in the case of MAX-phase compositions, to interleaved A-group element arrays), either by covalent, metallic, or lattice bonds, and which cannot be separately accessed. By contrast, in various embodiments of the present compositions, each layer has two available or accessible surfaces sandwiching each substantially two-dimensional array of crystal cells, each of which surfaces can be accessed for physical or chemical interrogation or modification.

It is important to note that, as prepared, the 2D MXene surfaces are not M-terminated (e.g., Ti-terminated), but primarily covered by oxide, OH, F groups or some combination thereof. For example in the case of a MXene of nominal composition $Ti_3C_2$ (e.g., derived from MAX phase $Ti_3AlC_2$) in fact is probably better represented by a formula such as $Ti_3C_2(OH)_xO_yF_z$. However, since the exact surface composition may not be known with certainty and can vary from sample to sample, and for the sake of brevity, herein, such MXene compositions of this sort (e.g., such as derived from $Ti_3AlC_2$) may be referred to as $Ti_3C_2(OH)_xO_yF_z$, $Ti_3C_2$, or $Ti_3C_2T_s$ (where $T_s$ refers to "surface terminations"), or more generally $M_{n+1}X_nT_s$, the latter terms being useful to replace the more cumbersome former term, in a manner similar to the use of a general name "graphene oxide" for oxidized graphene, which has a variety of oxygen-containing groups.

Having said this, the ability to functionalize the surfaces of the layers of the present invention to provide enrichment of a particular functional group provides a considerable synthetic and structural flexibility. Because of the arrangement of the M atoms within the $M_{n+1}X_n$ framework, wherein each X is positioned within an octahedral array of M atoms, the "unfunctionalized" surface comprises largely M atoms. For example, in the absence of imperfections, a substantially planar array of crystal cells having an empirical formula $Ti_3C_2$ will provide or present external surfaces comprising a planar array of Ti atoms (see, e.g., FIG. 3). At the same time, owing to the chemical reactivity of Ti (or any of the M atoms), these surfaces will be coated with one or more organic or inorganic moieties, generally comprising heteroatoms or having heteroatom linking groups.

For example, in certain embodiments, at least one of the surfaces are coated with a coating comprising H, N, O, or S atoms, for example, a hydride, oxide, sub-oxide, nitride, sub-nitride, sulfide, or sub-sulfide. In preferred embodiments, the coating comprises a hydrated or anhydrous oxide, a sub-oxide, or some combination thereof. As used herein the terms "sub-oxide," "sub-nitride," or "sub-sulfide" is intended to connote a composition containing an amount reflecting a sub-stoichiometric or a mixed oxidation state of the M metal at the surface of oxide, nitride, or sulfide, respectively. For example, various forms of titania are known to exist as $TiO_x$, where x can be less than 2. Accordingly, the surfaces of the present invention may also contain oxides, nitrides, or sulfides in similar sub-stoichiometric or mixed oxidation state amounts.

In other embodiments, at least one surface is coated with a coating having a pendant moiety which is linked to the surface by an N, O, or S atom (e.g., an M-N, M-O, or M-S bond, respectively). Such surface coatings then may comprise at least one hydroxide, alkoxide, carboxylate, amine, amide, or thiol. These pendants may contain organic moieties, including saturated, unsaturated, and/or aromatic moieties. These organic moieties may optionally include heteroatoms, be linear or branched, and/or may contain one or more functional groups, for example amines and derivatives therefrom, (thio)carboxylic acids and derivatives therefrom, hydroxy or ether groups, and/or thiol groups. The moieties and/or optionally available functional groups may exist in their neutral or ionized state.

In other embodiments, the coating of at least one surface comprises at least one halide, for example F, Cl, Br, or I, preferably F. As used herein, the terms "halide" and, e.g., "fluoride" are intended to reflect the presence of metal-halogen or metal-fluorine bonds, respectively, without regard to the specific nominal charge on the halogen or fluorine.

The skilled artisan will be able to interchange the pendant groups by methods known in the art. Without the need for an exhaustive delineation of such methods, in one non-limiting example, a hydroxy or alkoxy surface may be prepared by providing an excess hydroxide or alkoxide so as to displace the halide from an initially presented M-halide surface or so as to hydrate or alkoxylate a metal oxide or sub-oxide surface. Similarly, an originally presented M-hydroxide surface may be converted to oxide or sub-oxide surface by application of heat or other dehydrating conditions. Nitrogen and sulfur surfaces may be analogously interconverted by methods known in the art for making such conversions. Similarly, hydrides may be prepared by exposing precursors to reducing conditions, either electrolytically or by contacting with reducing agents such as hydrides (e.g., $NaBH_4$), hydrogen gas, or ammonia.

In certain embodiments, the compositions may be electrically conducting or semi-conducting.

In certain embodiments, the compositions of the present invention comprises at least one individual layer having first and second surfaces, each layer comprising a substantially two-dimensional array of crystal cells having an empirical formula $Ti_3C_2$, with at least one surface coated with a coating comprising a hydroxide, an oxide, a sub-oxide, or a combination thereof, and so optionally represented as $Ti_3C_2T_s$. In other embodiments, the coating comprises fluorine or fluoride.

In other embodiments, the crystalline composition comprises at least one individual layer having first and second surfaces, each layer comprising a substantially two-dimensional array of crystal cells having an empirical formula $Ta_4C_3$, with at least one surface coated with a coating comprising a hydroxide, an oxide, a sub-oxide, or a combination thereof, and so represented as $Ta_4C_3T_s$.

In still other embodiments, the crystalline composition comprises at least one individual layer having first and second surfaces, each layer comprising a substantially two-dimensional array of crystal cells having an empirical formula $(Cr_xV_x)_3C_2$ (including where $x=y=\frac{1}{2}$) with at least one surface coated with a coating comprising a hydroxide, an oxide, a sub-oxide, or a combination thereof.

As described above, certain additional embodiments provide MXene compositions which exhibit conductive or semi-conductive behavior, as well as those electronic devices (e.g., transistors, where the use of graphene and $MoS_2$ has been successfully demonstrated) which incorporate such compositions so as to take advantage of this property. Further, it is shown that variations in the nature of the surface coating effects that behavior, as shown by density functional theory (DFT) calculations (methods described in Example 1, below) (FIG. 5(g)). For example, the calculated band structure of a single $Ti_3C_2$ layer resembles a typical semi-metal with a finite density of states at the Fermi level. Indeed, the resistivity of the thin disk shown in FIG. 4(e) is estimated to about an order of magnitude higher than the same disc made with unreacted $Ti_2AlC$ powders, which translates to a resistivity of ca. 0.03 μΩm. By contrast, when terminated with OH and F groups, the band structure has a semiconducting character with a clear separation between valence and conduction bands by 0.05 eV and 0.1 eV, respectively (FIG. 5(g)), thereby supporting the conclusion that it is possible to tune the electronic structure of exfoliated MAX layers—or MXene compositions—by varying the functional groups. Such further modifications of the functional groups themselves may provide additional flexibility in this regard.

In certain embodiments, MXene films or papers are sufficiently thin as to be transparent (see, e.g., Example 16), while maintaining surface conductivity. Optical transparencies as high as 90% have been obtained, though in certain embodiments, such MXene films or papers may exhibit optical transparencies (i.e., at least one wavelength in a range of about 250 nm to about 850 nm) in a range of from about 0% to about 95% or higher, from about 50% to about 95%, from about 70% to about 95%, or from about 70% to about 90%. Such thin films may be prepared by delaminating epitaxially grown thin films, either as-prepared or intercalated with one or more materials as described herein.

Additional embodiments provide for the use or incorporation of MXene compositions into other materials, or the incorporation of other materials within them. For example, various embodiments provide polymer composites into which a MXene composition is incorporated. More particularly, further embodiments provide polymer composite compositions wherein the MXene compositions comprises between amounts in the range of about 0.1 wt % to about 50 wt %, relative to the combined weight of the polymer and MXene composition. Still other embodiments provide that the MXene composition is present in a range whose lower amount is about 0.1, about 1, about 2, about 5, or about 10 wt % and the upper amount is about 50 wt %, about 40 wt %, about 30 wt %, about 20 wt %, about 10 wt %, or about 5 wt %, relative to the combined weight of the polymer and the MXene composition comprising a polymer.

The polymer composite may be comprised of organic polymers, more specifically thermoset or thermoplastic polymers or polymer resins, elastomers, or mixtures thereof. Various embodiments include those wherein the polymer or polymer resin contains an aromatic or heteroaromatic moiety, for example, phenyl, biphenyl, pyridinyl, bipyridinyl, naphthyl, pyrimidinyl, including derivative amides or esters of terephthalic acid or naphthalic acid. Other embodiments provide that the polymer or polymer resin comprises polyester, polyamide, polyethylene, polypropylene, polyethylenenaphthalate (PEN), polyethylene terephthalate (PET), polybutylene terephthalate (PBT), polyether etherketone (PEEK), polyamide, polyaryletherketone (PAEK), polyethersulfone (PES), polyethyleneimine (PEI), poly (p-phenylene sulfide) (PPS), polyvinyl chloride (PVC), fluorinated or perfluorinated polymer (such as a polytetrafluoroethylene (PTFE or TEFLON®), polyvinylidene difluoride (PVDF), a polyvinyl fluoride (PVF or TEDLAR®)) (TEFLON® and TEDLAR® are registered trademarks of the E.I. DuPont de Nemours Company, of Wilmington, Del.)

It is believed that the planar nature of MXene layers may be well suited to organizing themselves in those anisotropic polymers, for example having planar moieties, e.g., aromatic moieties, especially when (but not only when) these planar organic moieties are directionally oriented to be parallel in a polymer composite composition. Such embodiments include the inclusion of MXene compositions into liquid crystal polymers. Moreover, the ability to produce MXene compositions having both hydrophobic and hydrophilic pendants provides for compatibility with a wide-ranging variety of polymer materials.

Additional embodiments of the present invention provide polymer composites, including those wherein the polymer composite is in a form having a planar configuration—for example, a film, sheet, or ribbon—comprising a MXene layer or multilayer composition. Still further embodiments provide such polymer composites wherein the two-dimensional crystal layers of the MXene materials are aligned or substantially aligned with the plane of a polymer composite film, sheet, or ribbon, especially when the organic polymers are oriented in the plane of that film, sheet, or ribbon.

The large elastic moduli predicted by ab initio simulation, and the possibility of varying their surface chemistries (beyond those exemplified herein, which are terminated by hydroxyl and/or fluorine groups) render these nanosheets attractive as polymer composite fillers. For example, the elastic modulus of a single, exfoliated $Ti_3C_2(OH)_2$ layer, along the basal plane, is calculated to be around 300 GPa, which is within the typical range of transition metal carbides and significantly higher than most oxides and clays (see, e.g., P. H. Nadeau, Applied Clay Science 1987, 2, 83, which is incorporated by reference herein in its entirety). And while the 300 GPa value is lower than that of graphene (e.g., as described in S. Stankovich, et al., Nature 2006, 442, 282, which is incorporated by reference herein in its entirety), the ability to match the character of the MXene layered materials with that of the polymer matrix, as described above, is expected to ensure better bonding to and better dispersion in polymer matrices when these MXene layers are to be used as reinforcements in polymer composites. It is also important to note here that the functionalized $Ti_3C_2$ sheets described herein were much more stable than graphene sheets under the 200 kV electron beam in the TEM.

Accordingly, still further embodiments provide that the MXene composition-filled composite polymers, especially when these polymer composites have a planar configuration, such as that of film, sheet, or ribbon, especially an oriented film, sheet, or ribbon, exhibit a flexural strength (bending rigidity) and/or stiffness than that of the corresponding film, sheet, or ribbon of the same polymer without the MXene composition. In some embodiments, this greater flexural strength and/or stiffness is independently at least 5%, at least 10%, or at least 25% higher than the flexural strength or toughness than that exhibited by an otherwise equivalent, but unfilled material.

Thus far, the compositions have been described in terms of having individual layers having first and second surfaces, each layer comprising a substantially two-dimensional array of crystal cells. However, additional embodiments provide for stacked assemblies of at least two layers having first and second surfaces, each layer comprising a substantially two-dimensional array of crystal cells, each crystal cell having the empirical formula of $M_{n+1}X_n$, such that each X is positioned within an octahedral array of M; wherein M is a Group IIIB, IVB, VB, or VIB metal or Mn; each X is C or N; and n=1, 2, or 3; and wherein the layers are characterized as having an average surface area and interlayer distance.

In various embodiments of these stacked assemblies, each layer may retain the characteristics as described above, but be held in place or edge-wise connected such that the assembly has up to about 50 layers of crystal layers. In various embodiments, these number of crystal layers in these assemblies may be described as having a range having a lower end of 2, about 5, about 10, about 15, or about 20 and an upper range of about 50, about 40, about 30, about 25, about 20, and about 10, with exemplary ranges of 2 to about 50, 2 to about 25, 2 to about 20, about 5 to about 50, about 5 to about 25, about 5 to about 20, about 10 to about 50, about 10 to about 25, about 10 to about 20, about 10 to about 15, about 15 to about 20.

In various embodiments, the composite layers characterized as having an average surface area. While the bounds of these areas are not necessarily limited to any particular values, in certain preferred embodiments, the average surface or planar area is defined by a range of areas, with individual embodiments having a lower range value of about 50 nm$^2$, about 100 nm$^2$, about 250 nm$^2$, about 500 nm$^2$, or about 1000 nm$^2$, and having an upper range value of about 10,000 nm$^2$, about 5000 nm$^2$, about 2500 nm$^2$, about 1000 nm$^2$, about 500 nm$^2$, about 250 nm$^2$, or about 100 nm$^2$, with exemplary ranges of about 100 nm$^2$ to about 2500 nm$^2$, of about 250 nm$^2$ to about 2500 nm$^2$, of about 500 nm$^2$ to about 1500 nm$^2$, of about 500 nm$^2$ to about 1000 nm$^2$, 50 nm$^2$ to about 250 nm$^2$, or about 750 nm$^2$ to about 1000 nm$^2$.

In other preferred embodiments, the average surface or planar area is defined by a range of areas, with individual embodiments having a lower range value of about 5 μm$^2$, about 10 μm$^2$, about 25 μm$^2$, about 50 μm$^2$, about 100 μm$^2$, about 250 μm$^2$, about 500 μm$^2$, or about 1000 μm$^2$ and having an upper range value of about 100,000 μm$^2$, 10,000 μm$^2$, about 1000 μm$^2$, about 500 μm$^2$, about 250 μm$^2$, about 100 μm$^2$, about 50 μm$^2$, about 25 μm$^2$, or about 10 μm$^2$, with exemplary ranges of about 10 μm$^2$ to about 250 μm$^2$, of about 25 μm$^2$ to about 250 μm$^2$, of about 50 μm$^2$ to about 150 μm$^2$, of about 50 μm$^2$ to about 100 μm$^2$, 5 μm$^2$ to about 25 μm$^2$, or about 75 μm$^2$ to about 125 μm$^2$.

While the surface of these composite layer may be of any shape, it is convenient to describe such shapes as having a major and minor planar dimension (or x-axis and y-axis dimensions, using the envisioned x-y plane as described above). For example, if a quadrilateral or pseudo-quadrilateral shape, the major and minor dimension is the length and width dimensions. In preferred embodiments, the ratio of the lengths of the major and minor axes is in the range of about 1 to about 10 (1:10) to about 10 to about 1 (10:1), about 1 to about 5 (1:5) to about 5 to about 1 (5:1), more preferably about 1 to about 3 (1:3) to about 3 to about 1 (3:1), or about 1 to about 2 (1:2) to about 2 to about 1 (2:1).

Additionally, in various embodiments, the interlayer distances (i.e., the distances between the composite crystal layers) in these stacked assemblies is in the range of about 0.2 nm to about 1 nm, preferably in the range of about 0.3 nm to about 0.5 nm. When prepared by the methods described below (i.e., removing the labile A-phase elements from MAX phase materials, see below), these interlayer distances may be consistent with the atomic radii of the removed elements. For example, the atomic diameter of Al is about 0.25 nm and that of Sn about 0.3 nm.

Certain embodiments of the present invention provide stacked assemblies which are capable of intercalating atoms and/or ions between at least some of the layers of two-dimensional crystal layers. Such spontaneous intercalation of cations from aqueous solutions was not theoretically or previously demonstrated. For example, these atoms and/or ions can be metal or metalloid atoms or ions, including alkali, alkaline earth, and transition metals. In some embodiments, these are alkali metal atoms and/or ions (e.g., Li, Na, K, and/or Cs); and most preferably lithium. In other embodiments, the atoms and/or ions include ammonium, magnesium, and aluminum. In some embodiments, these atoms and/or ions are able to move into and out of the stacked assemblies.

In certain embodiments, the cations intercalated spontaneously, on exposure of the cations to the MX-ene materials, using alkaline or acidic aqueous media (see, e.g., Example 13.2). Carbonates, carboxylates (such as described in Example 13.2), hydroxides, and sulfates may be used to introduce the cations into between the MXene layers. In some cases, notably Al$^{3+}$, the intercalation can additionally be promoted electrochemically. These intercalated compositions are able to induce high capacitances in flexible Ti$_3$C$_2$T$_s$ paper electrodes in aqueous electrolytes. Generally, these intercalated structures may be incorporated into electrodes, double layer capacitors, or both, where said structures further comprise, for example, conductive carbon (e.g., onion-like carbon or carbon black) and fluoropolymer binders (including perfluorinated binders known in the art, e.g., PTFE).

These multilayer structures or assemblies may be used for the same types of applications described above for the MXene layer compositions.

Additionally, the ability to intercalate lithium atoms and/or ions, together with the electrical properties of the MXene layers described above, provides the opportunities that these stacked assemblies may be used as energy storing devices (e.g., anodes) comprising these intercalated stacked composition, or the energy storage devices themselves, for example, batteries, comprising these elements.

Figure 6:
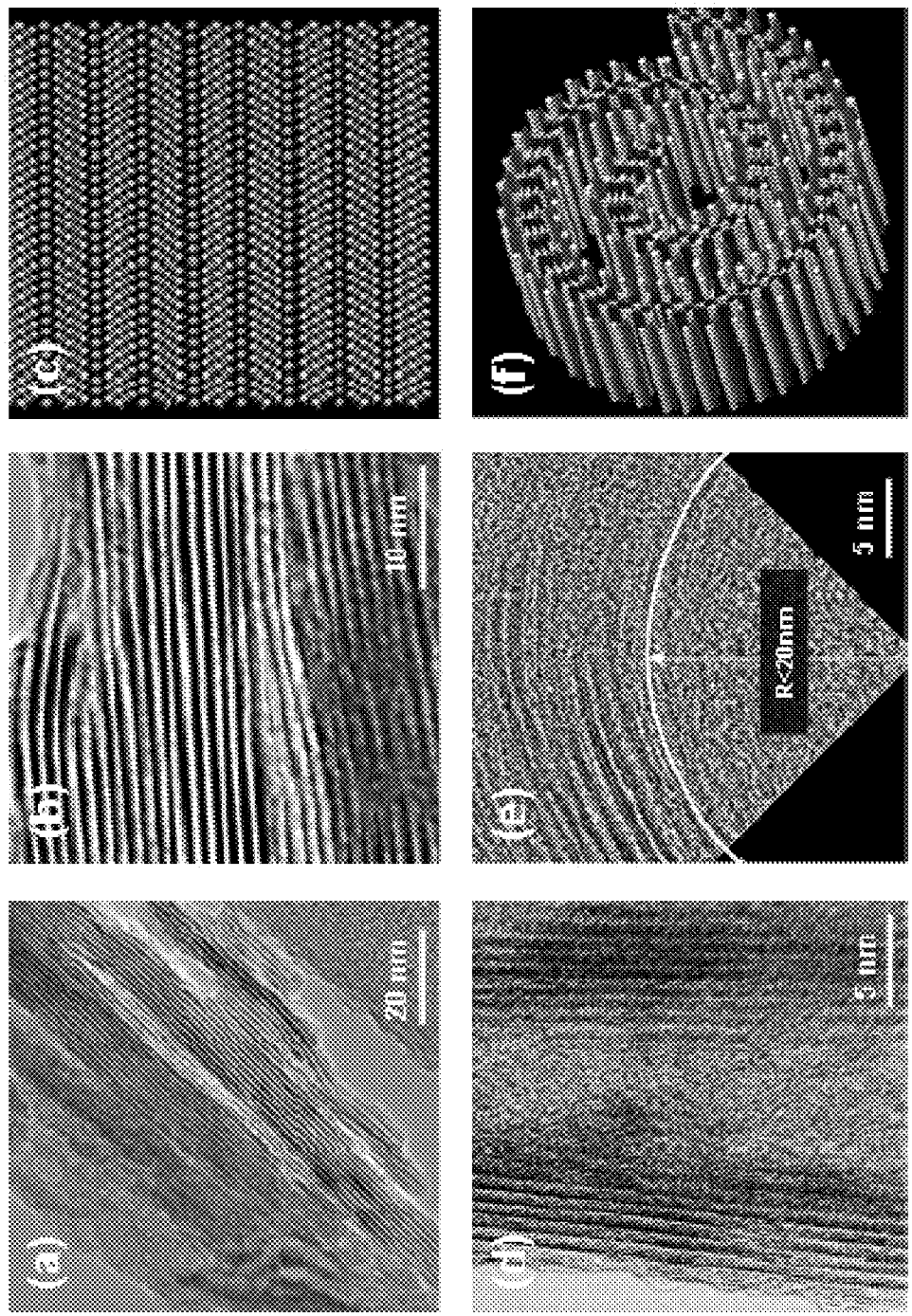
FIG. 6 provides TEM images and simulated structures of multi-layer MXene (a) TEM micrographs for stacked layers of Ti—C—O—F. Those are similar to multilayer graphene or exfoliated graphite that finds use in electrochemical storage. (b) TEM micrographs for the same stacked layers as in (a), but at a higher magnification. (c) a model of the Li-intercalated structure of $Ti_3C_2$ ($Ti_3C_2Li_2$). (d) TEM micrographs for a conical scroll of about 20 nm in outer diameter. (e) a cross sectional TEM image of a scroll with inner radius less than 20 nm. (f) a schematic representation of an MXene scroll (OH-terminated).

Density functional theory (DFT) calculations at 0 K and in Li-rich environments show that the formation of Ti$_3$C$_2$Li$_2$ as a result of the intercalation of Li into the space vacated by the Al atoms (FIG. 6(c)) assuming reaction

$$Ti_3C_2 + 2Li = Ti_3C_2Li_2 \qquad (4)$$

has an enthalpy change of 0.28 eV. One possible reason for the positive value maybe the fact that Li has an atomic radius of 145 pm, whereas that of Al is 125 pm. The structure shown in FIG. 6(c) would provide a capacity of 320 mAhg$^{-1}$, which is comparable to the 372 mAhg$^{-1}$ of graphite for (LiC$_6$). More recently, a steady state capacity of ca. 410 mAhg$^{-1}$ has been achieved for MX-ene compositions comprising Ti$_3$C$_2$ intercalated with Lit Accordingly, various embodiments of the present invention include Li-ion batteries (FIG. 6(c)) and pseudo-capacitor electrodes, wherein the MXene layers or assemblies replace layered transition metal oxides, which show useful red-ox properties and Li-intercalation, but which have lower electrical conductivities than described herein for the MXene materials.

The ability of MXene to intercalate ions, including lithium ions, so as to allow these materials to act as Li-ion batteries and/or pseudo-capacitor electrodes, is shown in Example 10, below. Similarly, the ability to intercalate a wide range of cations from aqueous solutions (as shown in Example 13), both from multilayer MX-enes and MX-ene "paper" made from a few layers of MX-ene materials, makes these ionically intercalated materials useful for those embodiments comprising flexible and wearable energy storage devices. The fact that a variety of ions, as different as Na$^+$ and Al$^{3+}$, can be accommodated between the MXene layers provide for embodiments comprising batteries as well as in metal-ion capacitors (battery-supercapacitor hybrids) which comprise these intercalated MXene as well.

Other embodiments of the present invention provide stacked assemblies which are capable of being intercalated or actually are intercalated by small molecules or salts thereof between at least some of the layers of two-dimensional crystal layers. In this regard, the term "small molecules," describes molecules comprising C, H, N, O, or S, and having molecular weights less than about 250 daltons. These molecules or salts are preferably, but not necessarily, polar. These molecules or salts are preferably, but not necessarily, aprotic. In some embodiments, the stacked assemblies are capable of being intercalated or actually are intercalated by molecules or salts thereof, said molecules or salt being those which are known to intercalate into kaolinite between at least some of the layers of two-dimensional crystal layers. In this regard, they may be described to as "kaolinitic intercalators." Without being bound to any particular theory, it appears that these intercalating chemicals are capable of stably interacting with the surface functionalities of the individual layers of the MX-ene materials. Exemplary small molecules or kaolinitic intercalators include hydrazine, hydrazine monohydrate, DMSO, urea, and N, N-dimethylformamide. Ammonium hydroxide has also been demonstrated to intercalate into these stacked assemblies. N-methylformamide (NMF) and 1-methyl-2-pyrrolidone (NMP) are also known to intercalate into kaolinite matrices Example 14 describes some exemplary, non-limiting methods of intercalating these types of chemicals into the MX-ene matrices. It is noted that for at least some of these chemicals, the intercalation is reversible—i.e., they can be inserted and removed by varying processing conditions, including simple exposure to the potential intercalant and variations in temperature, or both. It should also be apparent that introducing a first intercalated chemical into a given MX-ene matrix, may provide an opportunity to substitute it by a second chemical or chemicals, perhaps larger organic molecules, either by co- or post-intercalation, thereby providing a route to a broader class of intercalated compositions, similar to intercalated kaolinite derivatives. For example, pyrrolidinium halide and benzamide intercalation compounds of kaolinite are known to be available from DMSO intercalated kaolinite, and similar substitutions may be available for analogous compounds comprising these MX-ene materials. The specific embodiments described in Example 14 are deemed part of the present invention.

In addition to the compositions of the MXene materials, various embodiments provide for the preparation of such materials. Certain embodiments provide methods of preparing compositions comprising: (a) removing substantially all of the A atoms from a MAX-phase composition having an empirical formula of $M_{n+1}AX_n$; wherein M is an early transition metal or a mixture thereof, wherein A is a so-called A-group element (typically described, see below, as including Al, Si, P, S, Ga, Ge, As, Cd, In, Sn, Tl, and Pb); wherein X is C or N, or a combination thereof; and wherein n=1, 2, or 3 so as to provide a free standing composition comprising a framework of a substantially two-dimensional composite crystal layer having first and second surfaces.

MAX phase compositions are generally recognized as comprising layered, hexagonal carbides and nitrides have the general formula: $M_{n+1}AX_n$, (MAX) where n=1 to 3, in which M is typically described as an early transition metal (comprising a Group IIIB, IVB, VB, or VIB metal, or Mn), A is described as an A-group (mostly IIIA and IVA, or groups 13 and 14) element and X is either carbon and/or nitrogen. See, e.g., M. W. Barsoum, et al., "Synthesis and Characterization of a Remarkable Ceramic: $Ti_3SiC_2$," *J. Amer. Ceramics. Soc.*, 79, 1953-1956 (1996); M. W. Barsoum, "The $M_{N+1}AX_N$ Phases: A New Class of Solids: Thermodynamically Stable Nanolaminates," *Progress in Solid State Chemistry*, 28, 201-281 (2000), both of which are incorporated by reference herein. While $Ti_3AlC_2$ is among the most widely studied of these materials, more than 60 MAX phases are currently known to exist and are useful in the present invention. While not intending to be limiting, representative examples of MAX phase materials useful in the present invention include: (211) $Ti_2CdC$, $Sc_2InC$, $Ti_2AlC$, $Ti_2GaC$, $Ti_2InC$, $Ti_2TlC$, $V_2AlC$, $V_2GaC$, $Cr_2GaC$, $Ti_2AlN$, $Ti_2GaN$, $Ti_2InN$, $V_2GaN$, $Cr_2GaN$, $Ti_2GeC$, $Ti_2SnC$, $Ti_2PbC$, $V_2GeC$, $Cr_2AlC$, $Cr_2GeC$, $V_2PC$, $V_2AsC$, $Ti_2SC$, $Zr_2InC$, $Zr_2TlC$, $Nb_2AlC$, $Nb_2GaC$, $Nb_2InC$, $Mo_2GaC$, $Zr_2InN$, $Zr_2TlN$, $Zr_2SnC$, $Zr_2PbC$, $Nb_2SnC$, $Nb_2PC$, $Nb_2AsC$, $Zr_2SC$, $Nb_2SC$, $Hf_2InC$, $Hf_2TlC$, $Ta_2AlC$, $Ta_2GaC$, $Hf_2SnC$, $Hf_2PbC$, $Hf_2SnN$, $Hf_2SC$; (312) $Ti_3AlC_2$, $V_3AlC_2$, $Ti_3SiC_2$, $Ti_3GeC_2$, $Ti_3SnC_2$, $Ta_3AlC_2$, and (413) $Ti_4AlN_3$, $V_4AlC_3$, $Ti_4GaC_3$, $Ti_4SiC_3$, $Ti_4GeC_3$, $Nb_4AlC_3$, and $Ta_4AlC_3$. Solid solutions of these materials can also be used as described herein (e.g., see Example 4).

MAX phase materials are themselves known to exist as laminated structures with anisotropic properties. These materials are layered hexagonal (space group $P6_3/mmc$), with two formula units per unit cell (FIG. 1). Near close-packed M-layers are interleaved with pure A-group element layers, with the X-atoms filling the octahedral sites between the former.

Within the MAX phase structure, the $M_{n+1}X_n$ layers are chemically quite stable, possibly owing to the strength of the M-X bond. By comparison, the A-group atoms are the most reactive species, reflective of their relatively weak binding. For example, heating $Ti_3SiC_2$ in a C-rich atmosphere or heating in molten cryolite or molten aluminum is known to result in the loss of Si and the formation of $TiC_x$. In the case of cryolite, the vacancies that form lead to the formation of a partially ordered cubic $TiC_{0.67}$ phase. In both cases, the high temperatures lead to a structural transformation from a hexagonal to a cubic lattice and a partial loss of layering. In some cases, such as $Ti_2InC$, simply heating in vacuum at ca. 800° C., results in loss of the A-group element and $TiC_x$ formation. Removing of both the M and A elements from MAX structure by high temperature chlorination results in a porous carbon known as carbide derived carbon with useful and unique properties.

By contrast, the present methods surprisingly provide for the preparation of compositions comprising layers or stacked assemblies of at least one layer having first and second surfaces, each layer comprising a substantially two-dimensional array of crystal cells, each crystal cell deriving from the $M_{n+1}X_n$ layers of MAX phase compositions. These compositions are capable of free-standing or can be organized into stacked assemblies of coated crystal layers.

As used herein, the term "removing substantially all of the A atoms from a MAX-phase composition" connotes embodiments wherein at least 50 atomic % of the A atoms are removed from a finally recovered sample, relative to the original MAX phase composition. In other more preferred independent embodiments, more than about 60 atomic %, more than about 70 atomic %, more than about 80 atomic %, more than about 90 atomic %, more than about 95 atomic %, more than about 98 atomic %, and more than about 99 atomic % of the A atoms are removed from a finally recovered sample, relative to the original MAX phase composition.

Certain embodiments provide a process for removing these A atoms comprising treatment with an acid, preferably a strong acid capable of reacting with the A atoms. Such acids may be organic or inorganic acids, and may be applied in the gas or liquid phase, provided the resulting A-atom product can be removed from the lattice. In this regard, strong acids which include fluorine atoms appear to be especially preferred. Aqueous hydrofluoric acid is among those acids which appear especially useful. Aqueous ammonium hydrogen fluoride (NH$_4$F.HF) is another, more safely handled, acid which may be useful in effecting removal of the A atom. Other alkali metal bifluoride salts (i.e., QHF$_2$, where Q is Li, Na, or K) may also be useful for this purpose. Indeed, even conditions which generate aqueous HF in situ (for example, using alkali metal fluoride salts (e.g., NaF) in the presence of mineral acids, such as HCl or HNO$_3$, have been shown to provide mixtures capable of effectively removing the A atom from MAX phase materials. The skilled artisan will also appreciate that any reactant known to react preferentially with the A atoms of a given MAX phase composition, relative to the M$_{n+1}$X$_n$ may also be useful, for example selective chelants. Uses of such reactants are considered within the scope of this invention.

The extraction of the A group layers may be done at room, or even moderate, temperature, for example in the range of about 20° C. to about 800° C., preferably in temperature ranges wherein the lower temperature is about 20° C., about 25° C., about 30° C., about 40° C., about 50° C., about 60° C., about 80° C., about 100° C., about 200° C., or about 300° C., and wherein the upper temperature is about 600° C., about 500° C., about 400° C., about 300° C., about 250° C., about 200° C., about 150° C., about 100° C., about 80° C., or about 60° C. Exemplary examples of ranges include temperatures in the range of about 20° C. to about 100° C., about 20° C. to about 60° C., or about 30° C. to about 60° C. The extractions may be conducted using liquid or gas phase extraction methods. Gas phase reactions are generally to be done at the higher temperatures.

In further embodiments, the chemically treated materials are subjected to sonication, either using ultrasonic or mega sonic energy sources. This sonication may be applied during or after the chemical treatment.

One embodiment of the chemical exfoliation process for one representative material is diagrammatically illustrated in FIG. 3, and described further below. In this example, the treatment of Ti$_3$AlC$_2$ powders for 2 h in aqueous HF resulted in the formation of exfoliated 2-D Ti$_3$C$_2$ layers. The term "exfoliated" refers to a process of delaminating the individual (or multiple individual layers) from the stacked assemblies (see, e.g., the second step illustrated in FIG. 3). The exposed Ti surfaces appear to be terminated by OH and/or F (see Examples below). While not intending to be bound by the correctness of any single theory or mechanism, based on the experimental information provided below, it appears that the following simplified reactions occur when Ti$_3$AlC$_2$ is immersed in aqueous HF:

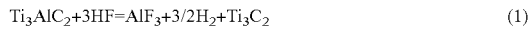  (1)

  (2)

  (3)

Reaction (1) appears to be a necessary step, at least to the extent that it provides for the extraction of AlF$_3$ in some form (e.g., perhaps some soluble derivative, such as H$_3$AlF$_6$), followed or accompanied by reaction (2) and/or (3). Evidence consistent with the aforementioned reactions and that they result in the exfoliation of 2-D Ti$_3$C$_2$ layers, with OH and/or F surface groups is presented below. Reactions (2) and (3) are simplified in that they assume the terminations are OH or F, respectively, when in fact they may be a combination of both.

Non-limiting examples of MXene compositions prepared by chemical exfoliation are illustrated in FIGS. 9-18.

In other embodiments, the exfoliation can be accomplished electrochemically. In various embodiments, MAX phase materials are selectively exfoliated to form the corresponding MXene by the application of potentiostatic or galvanostatic polarization. See Example 9, below.

It should also be recognized that, in addition to those embodiments described for the compositions provided above, other embodiments provide for compositions provided by the methods of preparation described herein. For example, those composition obtained from subjecting a MAX phase material to a chemical exfoliation process, said exfoliation process comprising treatment with aqueous HF and sonication, wherein a substantial portion of the A atoms are removed should also be considered within the scope of the present invention.

The following listing of embodiments is intended to complement, rather than displace or supersede, the previous descriptions.

Embodiment 1

A composition comprising at least one layer having first and second surfaces, each layer comprising:
a substantially two-dimensional array of crystal cells,
each crystal cell having an empirical formula of M$_{n+1}$X$_n$, such that each X is positioned within an octahedral array of M,
wherein M is at least one Group IBB, IVB, VB, or VIB metal, or Mn
wherein each X is C, N, or a combination thereof, and n=1, 2, or 3.

Embodiment 2

The composition of Embodiment 1 comprising a plurality of layers.

Embodiment 3

The composition of Embodiment 1 or 2, wherein M is at least one Group IVB, Group VB, or Group VIB metal.

Embodiment 4

The composition of any one of Embodiments 1 to 3, wherein M$_{n+1}$X$_n$ comprises Sc$_2$C, Sc$_2$N, Ti$_2$C, Ti$_2$N, Mo$_2$C, V$_2$C, V$_2$N, Cr$_2$C, Cr$_2$N, Zr$_2$C, Zr$_2$N, Nb$_2$C, Nb$_2$N, Hf$_2$C, Hf$_2$N, Ti$_3$C$_2$, Ti$_3$N$_2$, V$_3$C$_2$, V$_3$C$_2$, Ta$_3$C$_2$, Ta$_3$N$_2$, or Ti$_4$C$_3$, Ti$_4$N$_3$, V$_4$C$_3$, V$_4$N$_3$, Ta$_4$C$_3$, Ta$_4$N$_3$, or a combination thereof.

Embodiment 5

The composition of any one of Embodiments 1 to 4, wherein M$_{n+1}$X$_n$ comprises Ti$_3$C$_2$, Ti$_3$CN, Ti$_2$C, Ta$_4$C$_3$, or (V$_{1/2}$Cr$_{1/2}$)$_3$C$_2$.

Embodiment 6

The composition of any one of Embodiments 1 to 4, wherein M$_{n+1}$X$_n$ comprises V$_2$C, Mo$_2$C, Nb$_2$C$_3$, and Mo$_3$C$_2$.

Embodiment 7

The composition of any one of Embodiments 1 to 5, wherein M is Ti, and n is 1 or 2.

Embodiment 8

The composition of any one of Embodiments 1 to 5, wherein M is Ta.

Embodiment 9

The composition of any one of Embodiments 1 to 7, wherein n=1

Embodiment 10

The composition of any one of Embodiments 1 to 8, wherein n=

Embodiment 11

The composition of any one of Embodiments 1 to 5, wherein n=3.

Embodiment 12

The composition of any one of Embodiments 1 to 11, wherein the layer is in the form of a plane, a scroll, or a tube.

Embodiment 13

The composition of any one of Embodiments 1 to 12, wherein at least one of said surfaces is coated with a coating comprising alkoxide, carboxylate, halide, hydroxide, hydride, oxide, sub-oxide, nitride, sub-nitride, sulfide, thiol, or a combination thereof.

Embodiment 14

The composition of Embodiment 13, wherein the coating comprises fluorine atoms or fluoride ions.

Embodiment 15

The composition of Embodiment 13, wherein the coating comprises hydrated or anhydrous oxide or sub-oxide, or combination thereof

Embodiment 16

The composition of Embodiment 1, the crystal cells having an empirical formula $Ti_3C_2$ or $Ti_2C$ and wherein at least one of said surfaces is coated with a coating comprising hydroxide, oxide, sub-oxide, or a combination thereof.

Embodiment 17

The composition of Embodiment 1, the crystal cells having an empirical formula $Ta_4C_3$ and wherein at least one of said surfaces is coated with a coating comprising hydroxide, oxide, sub-oxide, or a combination thereof.

Embodiment 18

The composition of any one of Embodiments 1 to 17, wherein the composition comprises an electrically conductive or semiconductive surface.

Embodiment 19

A polymer composite comprising an organic polymer and the composition of any one of Embodiments 1 to 18.

Embodiment 20

The copolymer composite of Embodiment 19, wherein the polymer composite is in a form having a configuration defined by a two-dimensional plane, wherein the organic polymer is oriented coincident with the plane of that planar configuration.

Embodiment 21

The polymer composite of Embodiment 19 or 20, wherein the substantially two-dimensional array of crystal cells defines a plane, and said plane is substantially aligned with the plane of the polymer composite.

Embodiment 22

The polymer composite of any one of Embodiments 19 to 21, wherein the flexural strength and/or stiffness in the planar dimension of the polymer composite is greater than the flexural strength and/or stiffness of a corresponding polymer composition without the composition of claim 1.

Embodiment 23

A stacked assembly of at least two layers having first and second surfaces, each layer comprising:
a substantially two-dimensional array of crystal cells,
each crystal cell having the empirical formula of such that each X is positioned within an octahedral array of M;
wherein M is a Group TIM, IVB, VB, or VIB metal, or Mn;
each X is C, N, or a combination thereof; and
n=1, 2, or 3;
wherein the layers are characterized as having an average surface area and interlayer distance.

Embodiment 24

The stacked assembly of Embodiment 23, wherein $M_{n+1}X_n$ comprises $Sc_2C$, $Sc_2N$, $Ti_2C$, $Ti_2N$, $Mo_2C$, $V_2C$, $V_2N$, $Cr_2C$, $Cr_2N$, $Zr_2C$, $Zr_2N$, $Nb_2C$, $Nb_2N$, $Hf_2C$, $Hf_2N$, $Ti_3C_2$, $Ti_3N_2$, $V_3C_2$, $V_3C_2$, $Ta_3C_2$, $Ta_3N_2$, or $Ti_4C_3$, $Ti_4N_3$, $V_4C_3$, $V_4N_3$, $Ta_4C_3$, $Ta_4N_3$, or a combination thereof.

Embodiment 25

The stacked assembly of Embodiment 23, wherein $M_{n+1}X_n$ comprises $Ti_2C$, $Ti_2N$, $Ti_3C_2$, $Ti_3N_2$, $Ti_4C_3$, $Ti_4N_3$, $Ta_3C_2$, $Ta_3N_2$, $Ta_4C_3$, or $Ta_4N_3$, or a combination thereof.

Embodiment 26

The stacked assembly of any one of Embodiments 23 to 25, wherein $M_{n+1}X_n$ comprises $Ti_3C_2$, TiNbC, $Nb_2C$, $Ti_3CN$, $Ti_2C$, $Ta_4C_3$, or $(V_{1/2}Cr_{1/2})_3C_2$.

Embodiment 27

The stacked assembly of Embodiments 23 or 24, wherein comprises $V_2C$, $Mo_2C$, $Nb_2C_3$, and $Mo_3C_2$.

Embodiment 28

The stacked assembly of Embodiments 23, wherein $M_{M+1}X_n$ is $Ti_3C_2$, TiNbC, $Ti_3CN$, or $Ti_2C$.

Embodiment 29

The stacked assembly of Embodiments 23, wherein is $Ti_3C_2$.

Embodiment 30

The stacked assembly of any one of Embodiments 23 to 29, wherein at least one of the surfaces has bound thereto alkoxide, carboxylate, halide, hydroxide, hydride, oxide, sub-oxide, nitride, sub-nitride, sulfide, thiol, or a combination thereof.

Embodiment 31

The stacked assembly of any one of Embodiments 23 to 30, wherein the number of layers is in the range of 2 to about 50.

Embodiment 32

The stacked assembly of any one of Embodiments 23 to 29, wherein the average area of the layers is in the range of about 100 nm$^2$ to about 10,000 nm$^2$ or about 100 μm$^2$ to about 10,000 μm$^2$.

Embodiment 33

The composition of any one of Embodiments 23 to 30, capable of intercalating atoms and/or ions between at least some of the layers.

Embodiment 34

The stacked assembly of any one of Embodiments 23 to 31, said assembly resulting from the deposition of delaminated flakes of the composition onto a surface.

Embodiment 35

The stacked assembly of any one of Embodiments 23 to 34, said assembly exhibiting at least 65% tranparency to at least one wavelength of light in a range of from about 250 nm to about 850 nm and a surface resistivity of less than about 50 micro-ohm-meter.

Embodiment 36

The stacked assembly of any one of Embodiments 23 to 35, wherein atoms, ions, or both atoms and ions of the same material are intercalated between at least some of the layers.

Embodiment 37

The stacked assembly of any one of Embodiments 23 to 36, wherein the atoms, ions, or both atoms and ions of the same material comprise lithium, sodium, potassium, magnesium, or a combination thereof Embodiment 38

The stacked assembly of Embodiment 37, wherein the atoms, ions, or both atoms and ions of the same material comprise or consist essentially of lithium.

Embodiment 39

The stacked assembly of any one of Embodiments 23 to 38, further comprising a kaolinitic intercalator intercalated between at least some of the layers.

Embodiment 40

The stacked assembly of Embodiment 39, wherein the kaolinitic intercalator is hydrazine, DMSO, urea or N, N-dimethylformamide.

Embodiment 41

An energy-storing device or electrode comprising the stacked assembly of any one of Embodiments 23 to 40.

Embodiment 41

A battery comprising the stacked assembly of any one of Embodiments 23 to 40.

Embodiment 42

A method of preparing a composition comprising:
removing substantially all of the A atoms from a MAX-phase composition having an empirical formula of $M_{n+1}AX_n$.
wherein M is at least one Group TIM, IVB, VB, or VIB metal, or Mn,
wherein A is an A-group element;
each X is C, N, or a combination thereof and
n=1, 2, or 3,
thereby providing a composition comprising at least one layer having a first and second surface, each layer comprising a substantially two-dimensional array of crystal cells.

Embodiment 43

The method of Embodiment 42, wherein the A atoms are removed by a process comprising a treatment with a fluorine-containing acid.

Embodiment 44

The method of Embodiments 43, wherein the fluorine-containing acid is aqueous hydrofluoric acid.

Embodiment 45

The method of Embodiment 43, wherein the fluorine-containing acid is a substantially anhydrous gas.

Embodiment 46

The method of Embodiment 43, wherein the fluorine-containing acid comprises aqueous ammonium hydrogen fluoride ($NH_4F.HF$), $NaHF_2$, or a mixture resulting from the combination of an alkali metal salt with a mineral acid.

Embodiment 47

The method of any one of Embodiments 42 to 46, further comprising sonication.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Example 1

Methods and Materials

Powder of $Ti_3AlC_2$ was prepared by ball-milling $Ti_2AlC$ (>92 wt. % 3-ONE-2, Voorhees, N.J.) and TiC (99% Johnson Matthey Electronic, NY) powders in a 1:1 molar ratio for 24 h using zirconia balls. The mixture was heated to 1350° C. for 2 h under argon, Ar. The resulting loosely held compact was crushed in a mortar and pestle. Roughly 10 g of powders are then immersed in 100 ml of a 50% concentrated hydrofluoric acid, HF, (Fisher Scientific, Fair Lawn, N.J.) solution at room temperature for 2 h. The resulting suspension was then washed several times using de-ionized water and centrifuged to separate the powders. In some cases, to align the flakes and produce free-standing discs, the treated powders were cold pressed at a load corresponding to a stress of about 1 GPa in a steel die.

X-ray diffraction (XRD) patterns were obtained with a powder diffractometer (Siemens D500, Germany) using Cu $K_\alpha$ radiation, and a step scan of 0.02° and 1 s per step. Si powder was added to some samples as an internal standard. A scanning electron microscope, (SEM, Zeiss Supra 50VP, Germany) was used to obtain high magnification images of the treated powders. Transmission electron microscopes, TEMs, (JEOL JEM-2100F and JEM 2100, Japan; FEI, Tecnai G2 TF20UT FEG, Netherlands) operating at 200 kV were used to characterize the exfoliated powders. Chemical analysis in the TEM was carried out using an ultra-thin window X-ray energy dispersive spectrometer, EDAX (EDAX, Mahwah, N.J.). The TEM samples were prepared by deposition of the flakes—from an isopropanol suspension—on a lacey-200 mesh carbon-coated copper grid. Raman spectroscopy of the cold pressed samples was carried out on a microspectrometer (inVia, Renishaw plc, Gloucestershire, UK) using an Ar ion laser (514.5 nm) and a grating with 1800 lines/mm. This corresponds to a spectral resolution of 1.9 $cm^{-1}$ and a spot size of 0.7 μm in the focal plane. X-ray photoelectron spectroscopy, XPS, (PHI 5000, ULVAC-PHI, Inc., Japan) was used to analyze the surfaces of samples before and after exfoliation.

Theoretical calculations were performed by density functional theory (DFT) using the plane-wave pseudo-potential approach, with ultrasoft pseudopotentials and Perdew Burke Ernzerhof (PBE) exchange—Wu-Cohen (WC) correlation functional, as implemented in the CASTEP code in Material Studio software (Version 4.5). A 8×8×1 Monkhorst-Pack grid and planewave basis set cutoff of 500 eV were used for the calculations. Exfoliation was modeled by first removing Al atoms from the $Ti_3AlC_2$ lattice. Exposed Ti atoms located on the bottom and top of the remaining $Ti_3C_2$ layers were saturated by OH (FIG. 3(b)) or F groups followed by full geometry optimization until all components of the residual forces became less than 0.01 eV/Å. Equilibrium structures for exfoliated layers were determined by separating single $Ti_3C_2$ layers by a 1.2 nm thick vacuum space in a periodic supercell followed by the aforementioned full geometry optimization. Band structures of the optimized materials were calculated using a k point separation of 0.015 $Å^{-1}$. The elastic properties of the 2-D structures were calculated by subjecting the optimized structure to various strains and calculating the resulting second derivatives of the energy density.

Example 2

Experimental Characterization of $Ti_3C_2(OH)_2$ and $Ti_3C_2(F)_2$

Figure 4:
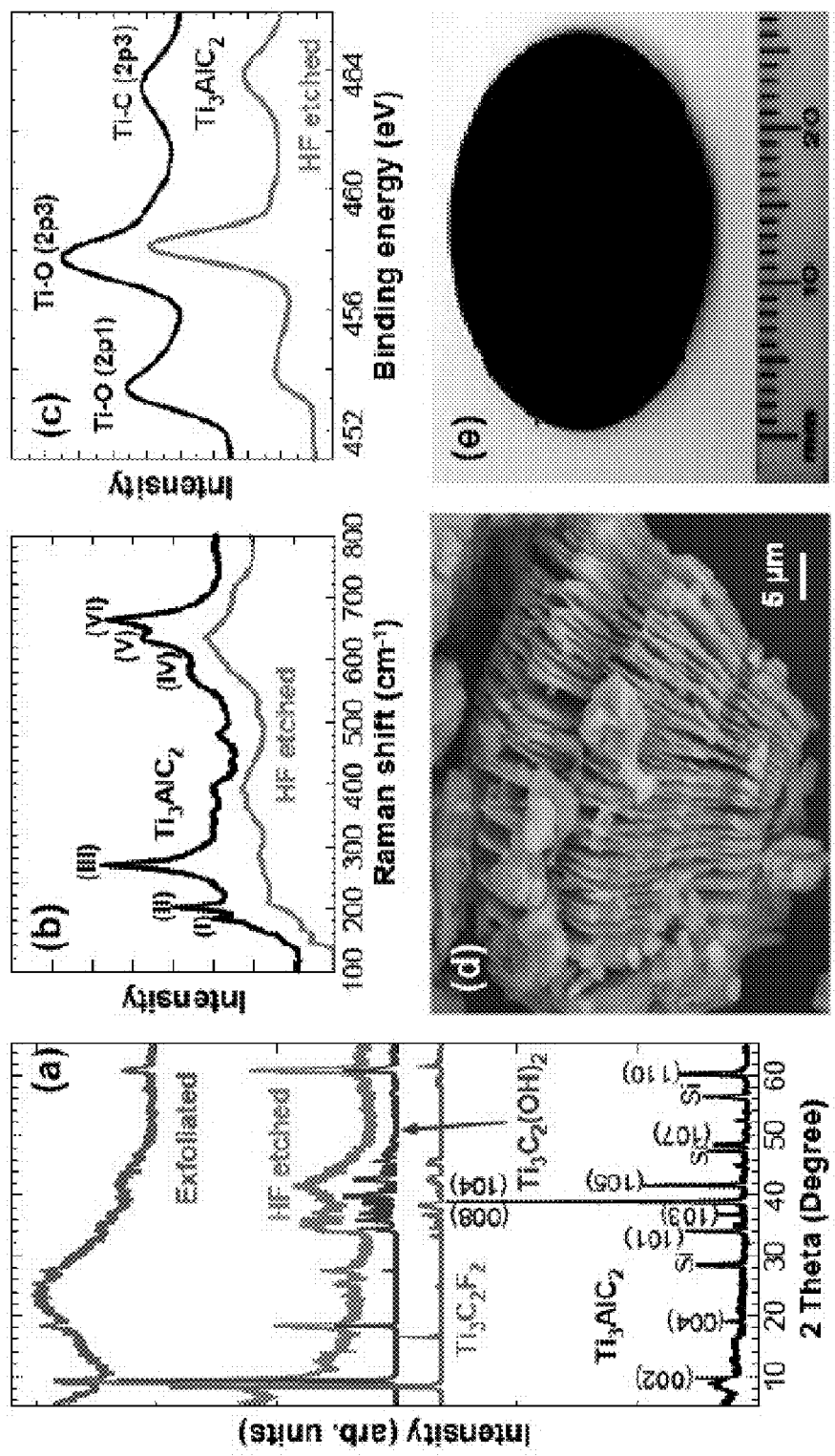
FIG. 4 provides analytical date of the $Ti_3AlC_2$ before and after exfoliation. (a) an XRD pattern for $Ti_3AlC_2$ before any treatment, simulated XRD patterns of $Ti_3C_2F_2$ and $Ti_3C_2(OH)_2$, measured XRD patterns of $Ti_3AlC_2$ after HF treatment, and exfoliated nanosheets produced by sonication. (b) Raman spectra of $Ti_3AlC_2$ before and after HF treatment. (c) XPS spectra of $Ti_3AlC_2$ before and after HF treatment. (d) an SEM image of a sample after HF treatment. (e) a cold processed 25 mm disk of etched and exfoliated material after HF treatment.

XRD spectra of the initial $Ti_2AlC$—TiC mixture after heating to 1350° C. for 2 h resulted in peaks that corresponded mainly to $Ti_3AlC_2$ (bottom curve in FIG. 4(a)). When the $Ti_3AlC_2$ powders were placed into the HF solution, bubbles, believed to be $H_2$, were observed suggesting a chemical reaction. Ultrasonication of the reaction products in methanol for 300 s resulted in significant weakening of the peaks and the appearance of an amorphous broad band around 24° (top spectrum in FIG. 4(a)). In other words, exfoliation leads to a loss of diffraction signal in the out-of-plane direction, and the non-planar shape of the nanosheets results in broadening of peaks corresponding to in-plane diffraction. When the same powders were cold pressed at 1 GPa, into free-standing, 300 μm thick and 25 mm diameter discs (FIG. 4(e)), their XRD showed that most of the non-basal plane peaks of $Ti_3AlC_2$—most notably the most intense peak at ≈39°—disappear (curve labeled "HF etched" in FIG. 4(a)). On the other hand, the (001) peaks, such as the (002), (004) and (010), broadened, lost intensity, and shifted to lower angles compared to their location before treatment. Using the Scherrer formula, as described in B. D. Cullity, Elements of X-ray diffraction, Addison-Wesley 1978, which is incorporated by reference herein, the average particle dimension in the [0001] direction after treatment is estimated to be 11±3 nm, which corresponds to roughly ten $Ti_3C_2(OH)_2$ layers. To identify the peaks we simulated XRD patterns of hydroxylated, viz. $Ti_3C_2(OH)_2$, (curve labeled "$Ti_3C_2(OH)_2$" in FIG. 4(a)) and fluorinated, $Ti_3C_2F_2$, structures (curved labeled as such in FIG. 4(a)). Clearly, both were in good agreement with the XRD patterns of the pressed sample (curve labeled "HF etched" in FIG. 4(a)), the agreement was better with the former. The disappearance of the most intense diffraction peak of $Ti_3AlC_2$ at 39° and the good agreement between the simulated XRD spectra for $Ti_3C_2(OH)_2$ and the experimental results provides strong evidence of the formation of the latter. The presence of OH groups after treatment was confirmed by FTIR.

Figure 5:
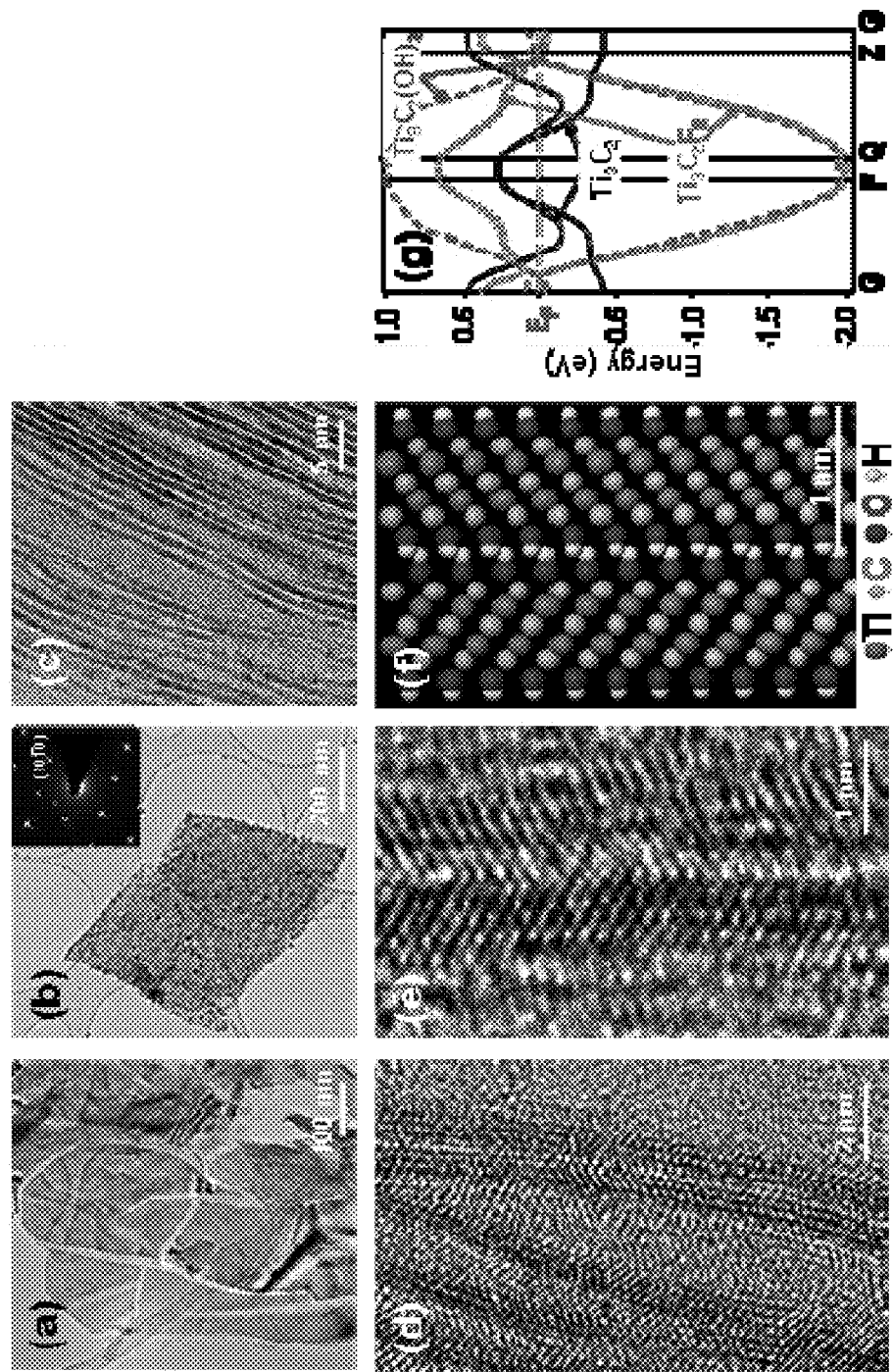
FIG. 5 shows micrographs of exfoliated MXene nanosheets. (a) TEM micrographs of exfoliated 2-D nanosheets of Ti—C—O—F. (b) TEM micrographs of exfoliated 2-D nanosheets; inset selected area diffraction, SAD, shows hexagonal basal plane. (c) TEM micrographs of single and double layer MXene sheets. (d) an HRTEM image showing the separation of individual sheets after sonication. (e) an HRTEM image of bilayer $Ti_3C_2(OH)_xF_y$ (alternatively, $Ti_3C_2T_s$). (f) an atomistic model of the layer structure shown in (e). (g) a calculated band structure of single layer MXene with —OH and —F surface termination and no termination ($Ti_3C_2$), showing a change from metal to semiconductor as a result of change in the surface chemistry.

Further DFT geometry optimization of the hydroxylated (FIG. 5(f)) and fluorinated structure resulted in 5% and 16% expansion of the original $Ti_3AlC_2$ lattice, respectively, as observed. If Al were simply removed, and not replaced by functional groups, the DFT optimization caused the structure to contract by 19%, which is not observed. The increase of the c-lattice parameters upon reaction (FIG. 4(a)) is thus strong evidence for the validity of reactions 2, 3.

Raman spectra of $Ti_3AlC_2$, before and after HF treatment, are shown in FIG. 4(b). Peaks II, III, and IV vanished after treatment, while peaks VI and VII, merged, broadened and downshifted. Such downshifting has been observed in Raman spectra of very thin layers of inorganic layered compounds, and is characteristic of such materials. See, e.g., C. N. R. Rao, et al., Science and Technology of Advanced Materials 2010, 11, 054502, which is incorporated by reference herein in its entirety. The line broadening, and the spectral shifts in the Raman spectra are consistent with exfoliation and are in agreement with the broadened XRD profiles. In analogy with $Ti_3SiC_2$ (see J. Spanier, S. Gupta, M. Amer, M. W. Barsoum, Physical Review B 2005, 71, 012103, which is also incorporated by reference herein), peaks I to III in FIG. 4(b) can be assigned to Al—Ti vibrations, while peaks V and VI involve only Ti—C vibrations. The fact that only the latter two exist after etching confirms both the mode assignments, but more importantly the loss of Al from the structure. Note that peaks V and VI are combined, broadened and downshifted after reaction.

The Ti 2p XPS spectra, before and after treatment, are shown in FIG. 4(c). The C is and Ti 2p peaks before treatment match previous work on $Ti_3AlC_2$. See, e.g., S. Myhra, et al., Journal of Physics and Chemistry of Solids 2001, 62, 811, which is incorporated by reference herein. The presence of Ti—C and Ti-0 bonds was evident from both spectra, indicating the formation of $Ti_3C_2(OH)_2$ after treatment. The Al and F peaks (not shown) were also observed and their concentrations were calculated to be around 3 at. % and 12 at. %, respectively. Aluminum fluoride ($AlF_3$)—a reaction product, see below—can probably account for most of the F signal seen in the spectra. The O 1s main signal (not shown at ~530.3 $cm^{-1}$) suggest the presence of OH group. See, e.g., M. Schmidt, S. G. Steinemann, Fresenius' Journal of Analytical Chemistry 1991, 341, 412, which is also incorporated by reference herein.

A SEM image of a ≈1500 $\mu m^3$ $Ti_3AlC_2$ particle (FIG. 4(d)) shows how the basal planes fan out and spread apart as a result of the HF treatment. EDAX of the particles showed them to be comprised of Ti, C, O and F, with little, or no, Al. This implies that the Al layers were replaced by oxygen (i.e. OH) and/or F. Note that the exfoliated particles maintained the pseudo-ductility of $Ti_3AlC_2$ and could be easily cold press into free-standing disks (FIG. 4(e)). This property can prove crucial in some potential applications, such as anodes for Li-ion batteries, as described above.

TEM analysis of exfoliated sheets (FIG. 5(a), (b)) shows them to be quite thin and transparent to electrons since the carbon grid is clearly seen below them. This fact strongly suggests a very thin foil, especially considering the high atomic number of Ti. The corresponding selected area diffraction, SAD (inset in FIG. 5(b)) shows the hexagonal symmetry of the basal planes. EDAX of the same flake showed the presence of Ti, C, O, and F. FIG. 5(c), (d) show cross-sections of exfoliated single- and double-layer MXene sheets. FIG. 5(e), (f) show high-resolution TEM micrographs and a simulated structure of two adjacent OH-terminated $Ti_3C_2$ sheets, respectively. The experimentally observed interplanar distances and angles are found to be in good agreement with the calculated structure. FIG. 6(a), (b) show stacked multilayer MXene sheets. The exfoliated layers can apparently also be rolled into conical shapes (FIG. 6(d)); some are bent to radii of <20 nm (FIG. 6(e)). Note that if Al atoms had been replaced by C atoms, the concomitant formation of strong Ti—C bonds—as when, for example, $Ti_3SiC_2$ reacts with cryolite at 900° C.—exfoliation would not have been possible. It follows that the reaction must have resulted in a solid in which the Ti—Al bonds are replaced by much weaker hydrogen or van der Waals bonds. This comment notwithstanding, the EDAX results consistently show the presence of F in the reaction products implying that, as noted above, the terminations are most likely a mixture of F and OH. The presence of up to 12 at. % F has also been confirmed using XPS. In the latter case, however, some of it could originate from $AlF_3$ residue in the sample.

Lastly, it is instructive to point out the similarities between MXene and graphene such as,
  (i) the exfoliation of 2-D $Ti_3C_2$ layers (FIGS. 6(a) and (b)) into multilayer sheets that resemble exfoliated graphite, see L. M. Viculis, et al., *Journal of Materials Chemistry* 2005, 15, 974, which is incorporated by reference herein.
  (ii) the formation of scrolls (FIGS. 6(d) and (e)).
Also, as cross-sectional TEM (FIG. 6(e)) shows, some nanosheets were bent to radii <20 nm without fracture, which is evidence for strong and flexible $Ti_3C_2$ layers. Similar scrolls were produced by sonication of graphene. See, e.g., L. M. Viculis, et al., Science 2003, 299, 1361; M. V. Savoskin, et al., Carbon 2007, 45, 2797, both of which are incorporated by reference herein. It is possible that the sonication used for exfoliation caused some nanosheets to roll into scrolls, as schematically shown in FIG. 6(f).

Example 3

Experimental Characterization of the Product of the Reaction Between $Ta_4AlC_3$ and Aqueous HF—$Ta_4C_3$$(OH)_x(F)_y$ $Ta_4AlC_3$ powder (ca. 10 g) was immersed in approximately 100 mL of a 50% concentrated hydrofluoric acid, HF, (Fisher Scientific, Fair Lawn, N.J.) solution at room temperature for 72 h. The resulting suspension was then washed several times using deionized water and centrifuged to separate the powders.

XRD analysis of the resulting material showed sharp peaks corresponding only to TaC, known to be an impurity in the starting material (i.e., in addition to peaks attributable to TaC, the XRD spectrum contained only broad peaks centered around $2\theta$ values of ca. 6° and 34-36°). However, the XRD spectrum of a sample obtained by cold pressing the resulting material, showed strong, albeit broadened peaks at about $2\theta$=5.7° and 6.8° (apparently shifted from $2\theta$~7.5 in XRD of $Ta_4AlC_3$), smaller peaks at about $2\theta$=13° (apparently shifted from $2\theta$~15° in XRD of $Ta_4AlC_3$), 26°, and 29°, and broad, albeit low intensity peaks centered at about $2\theta$=27-30° and 36°, none of which appear to correspond to TaC, but which are interpreted as being consistent with simulated spectra of $Ta_4C_3(OH)_2$. Compared with the XRD spectra of the original XRD spectrum of $Ta_4AlC_3$ (and its an accompanying pattern simulated by CrystalMaker®), the XRD pattern of the cold-pressed material also showed no evidence of otherwise distinguishing peaks at $2\theta$~22°, 29.5°.

Figure 10:
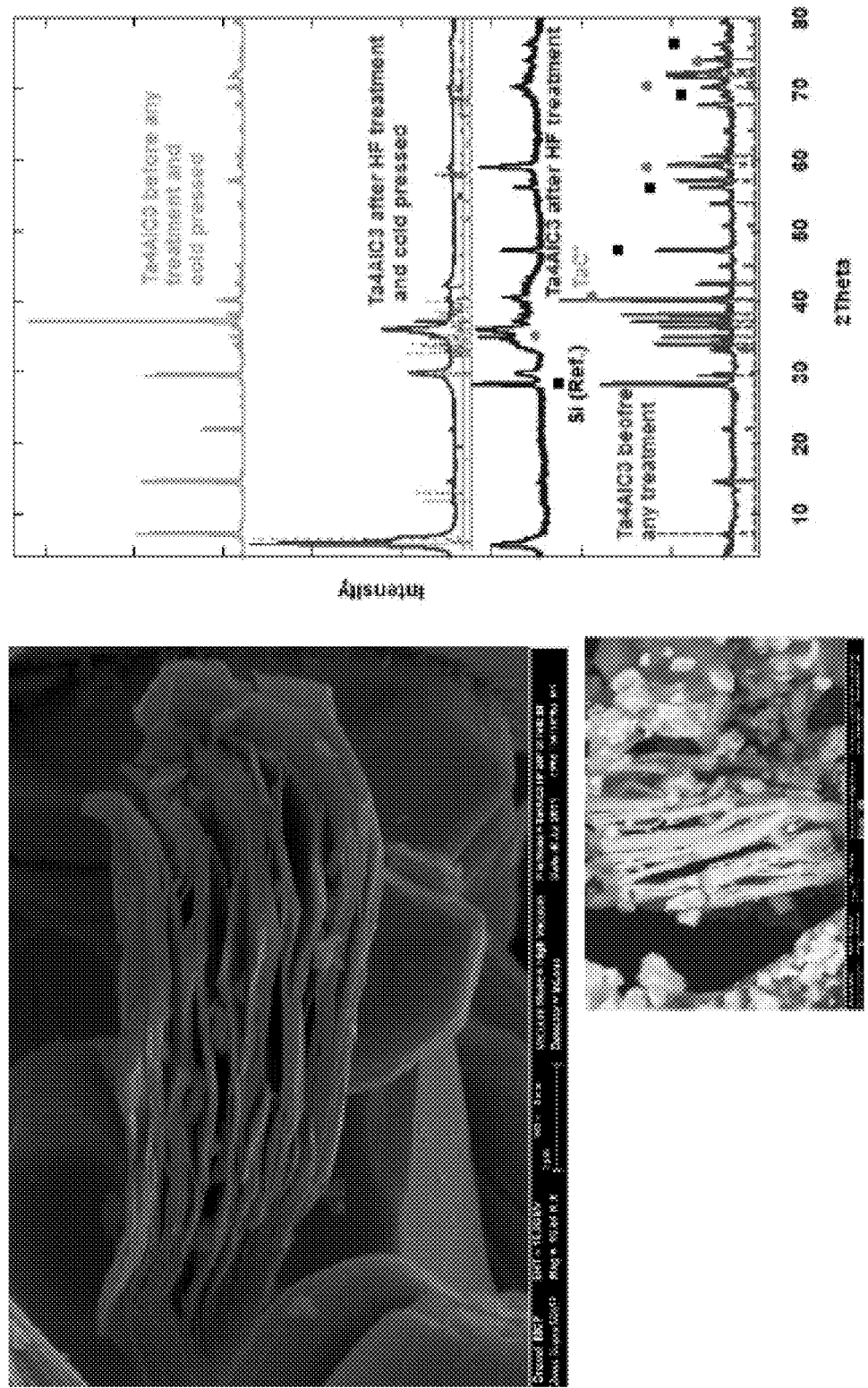
FIG. 10 shows SEM micrographs and XRD spectra of chemically exfoliated $Ti_4AlC_3$ (50% HF 72 hours at RT).

An illustrative XRD spectrum for an exfoliated, characterized to be $Ta_4C_3(OH)_x(F)_y$, are shown in FIG. 10.

Example 4

Figure 8:
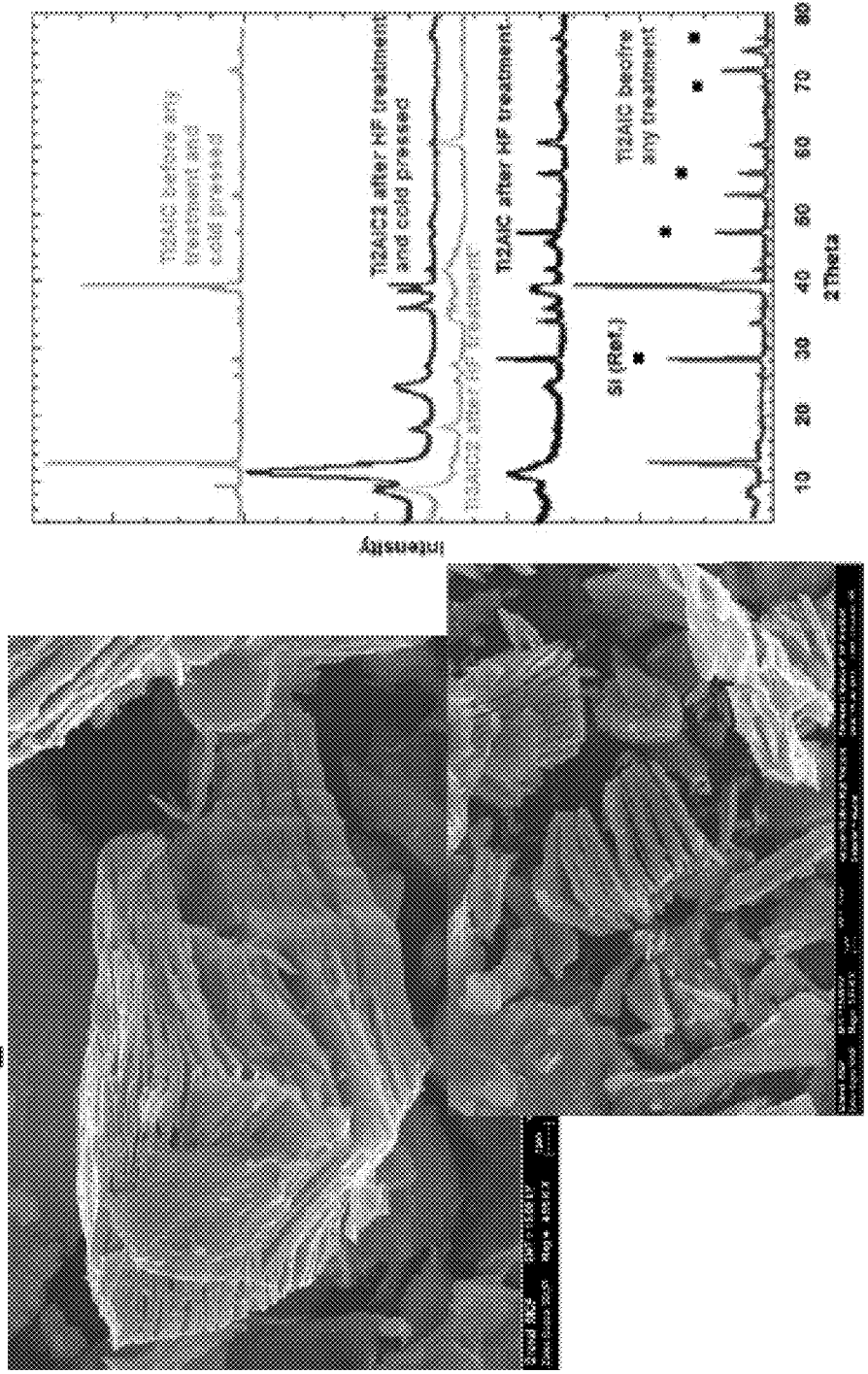
FIG. 8 shows SEM micrographs and XRD spectra of chemically exfoliated $Ti_2AlC$.

Experimental Characterization of the Product of the Reaction Between $Ti_2AlC$ and Aqueous HF—$Ti_2C$$(OH)_x(F)_y$ $Ti_2AlC$ powder (Kanthal Corp., Sweden) was immersed in approximately 100 mL of a 10% concentrated hydrofluoric acid, HF, (Fisher Scientific, Fair Lawn, N.J.) solution at room temperature for 10 h. The resulting suspension was then washed several times using deionized water and centrifuged to separate the powders. SEM micrographs and XRD spectra of the resulting materials are shown in FIG. 8.

Example 5

Figure 9:
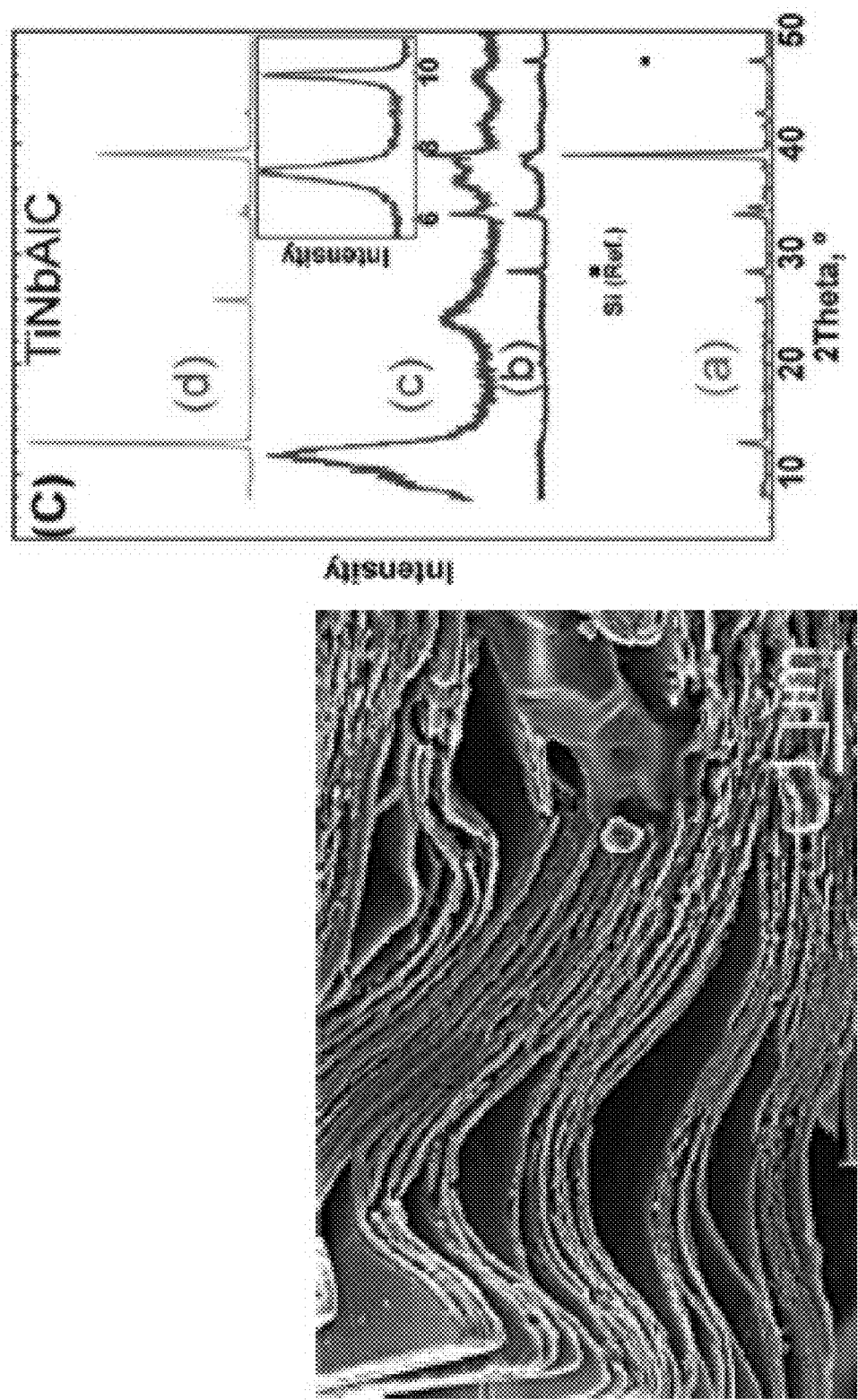
FIG. 9 shows a secondary electron SEM micrograph for TiNbAlC after HF treatment and XRD patterns before and after HF treatment at room temperature for TiNbAlC (50% HF 28 hrs) (inset is the XRD for $(V_{0.5}Cr_{0.5})AlC_2$; 50% HF 65 hrs, and cold pressed zoomed-in on the (0002) peak).

Experimental Characterization of the Product of the Reaction Between TiNbAlC and Aqueous HF)—TiNbC $(OH)_x(F)_y$ The TiNbAlC powders were made by mixing elemental titanium, Ti (Alfa Aesar, Ward Hill, USA, 99.5 wt % purity; 325 mesh), niobium, Nb (Atlantic Equipment Engineers, Bergenfield, USA, 99.8 wt % purity; 325 mesh), and the same Al and C used above, in the molar ratio of 1:1:1.2:1, respectively, in a ball mill for 12 h. The powders were then heated at the rate of 10° C./min in a tube furnace to 1500° C. for 1 h under flowing Ar. After cooling to room temperature, powders were processed as described above (see Table 1). SEM micrographs and XRD spectra of the resulting materials are shown in FIG. 9.

The XRD patterns for TiNbAlC, before and after HF treatment (FIG. 9), show that the intensity of the TiNbAlC peaks decreased significantly after HF treatment (considering that 10 wt % Si was used as an internal reference) and a new broad peak at ≈11.8° 2θ appeared after cold pressing. Here again a shoulder at a larger d spacing compared to the main peak is observed. The latter is most likely due to some exfoliated $(Ti_{0.5},Nb_{0.5})_3AlC_2$ that was present as a second phase in the starting powder. SEM micrographs (FIG. 9) clearly show exfoliated TiNbAlC particles. TEM micrographs, after sonication (not shown), show thin sheets composed of Ti, Nb, C, O, and F in an atomic ratio that EDX shows to be 14:16:23:34:13, respectively. HRTEM of a TiNbC layer (not shown) and its corresponding SAED again show hexagonal symmetry. At 0.2606 nm, the perpendicular separation of the (1010) lattice planes results in an a lattice constant of 0.301 nm. EELS for TiNbAlC after HF treatment and confirms the presence of Ti, Nb, C, F (not shown), and O, but no Al.

Example 6

Figure 14:
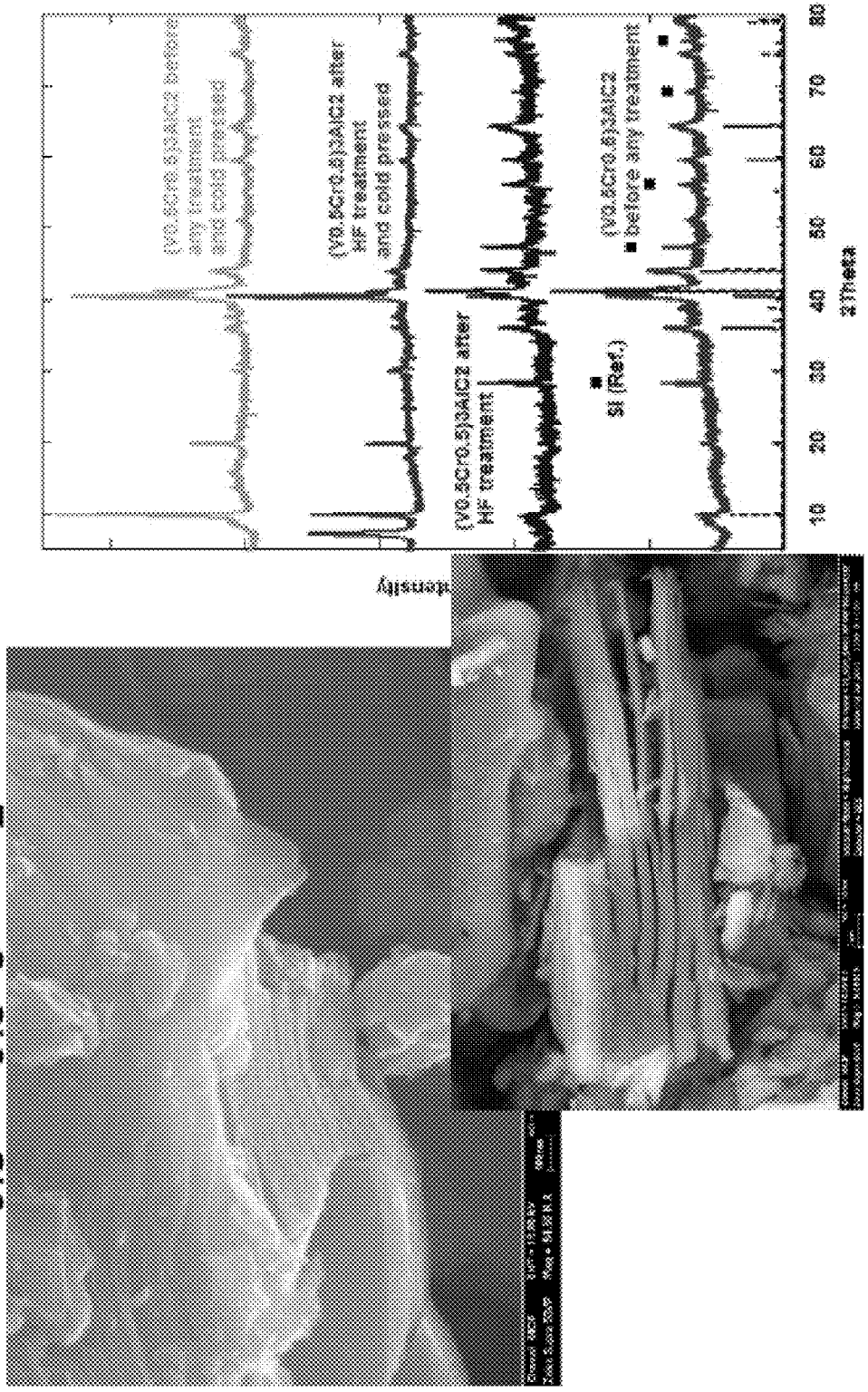
FIG. 14 shows SEM micrographs and XRD spectra of chemically exfoliated $(V_{1/2}Cr_{1/2})_3AlC_2$ (50% HF 69 hours at RT).
Figure 15:
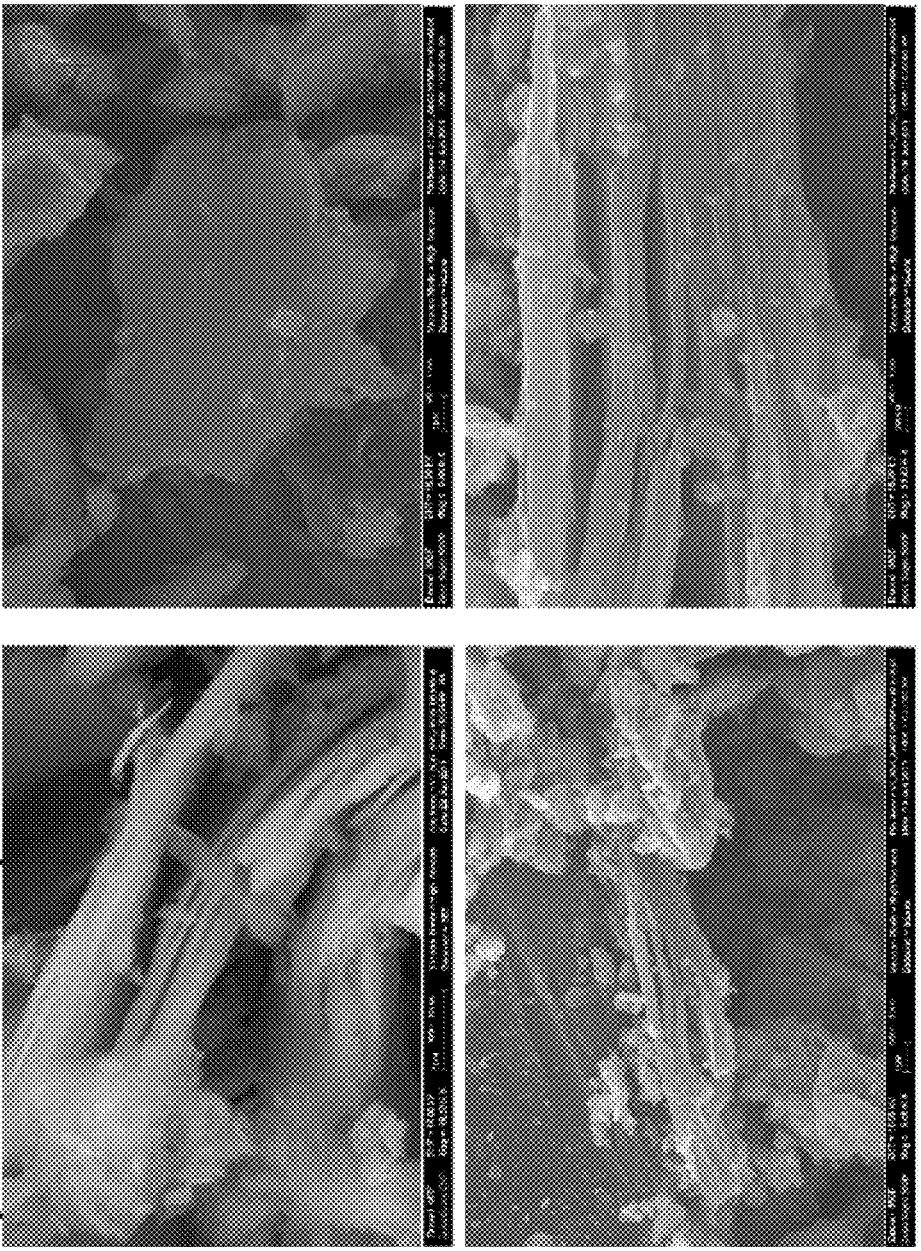
FIG. 15 shows additional SEM micrographs of chemically exfoliated $(V_{1/2}Cr_{1/2})_3AlC_2$ (50% HF 69 hours at RT).
Figure 16:
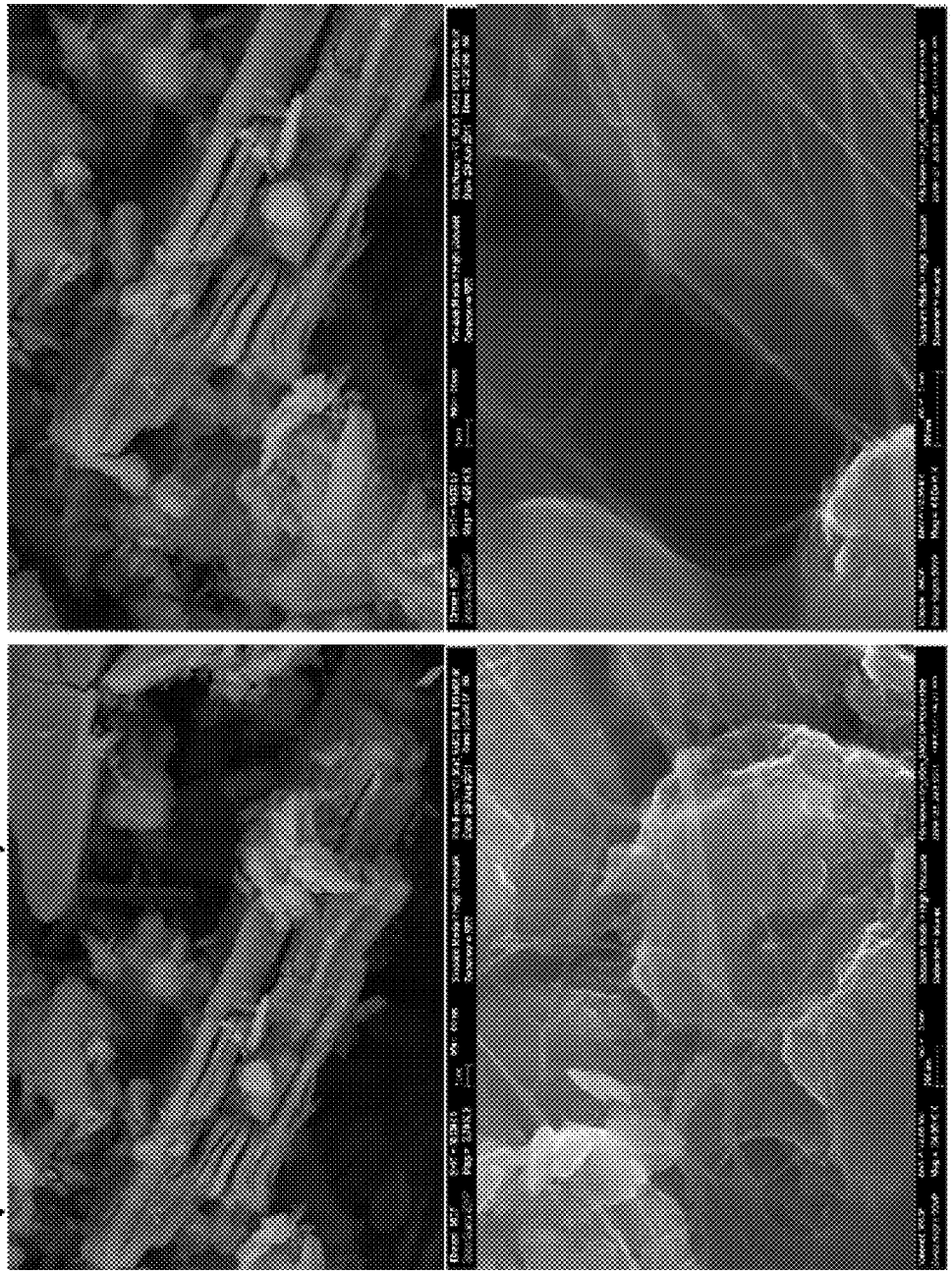
FIG. 16 shows SEM micrographs of chemically exfoliated $(V_{1/2}Cr_{1/2})_3AlC_2$ (50% HF 69 hours at RT).
Figure 17:
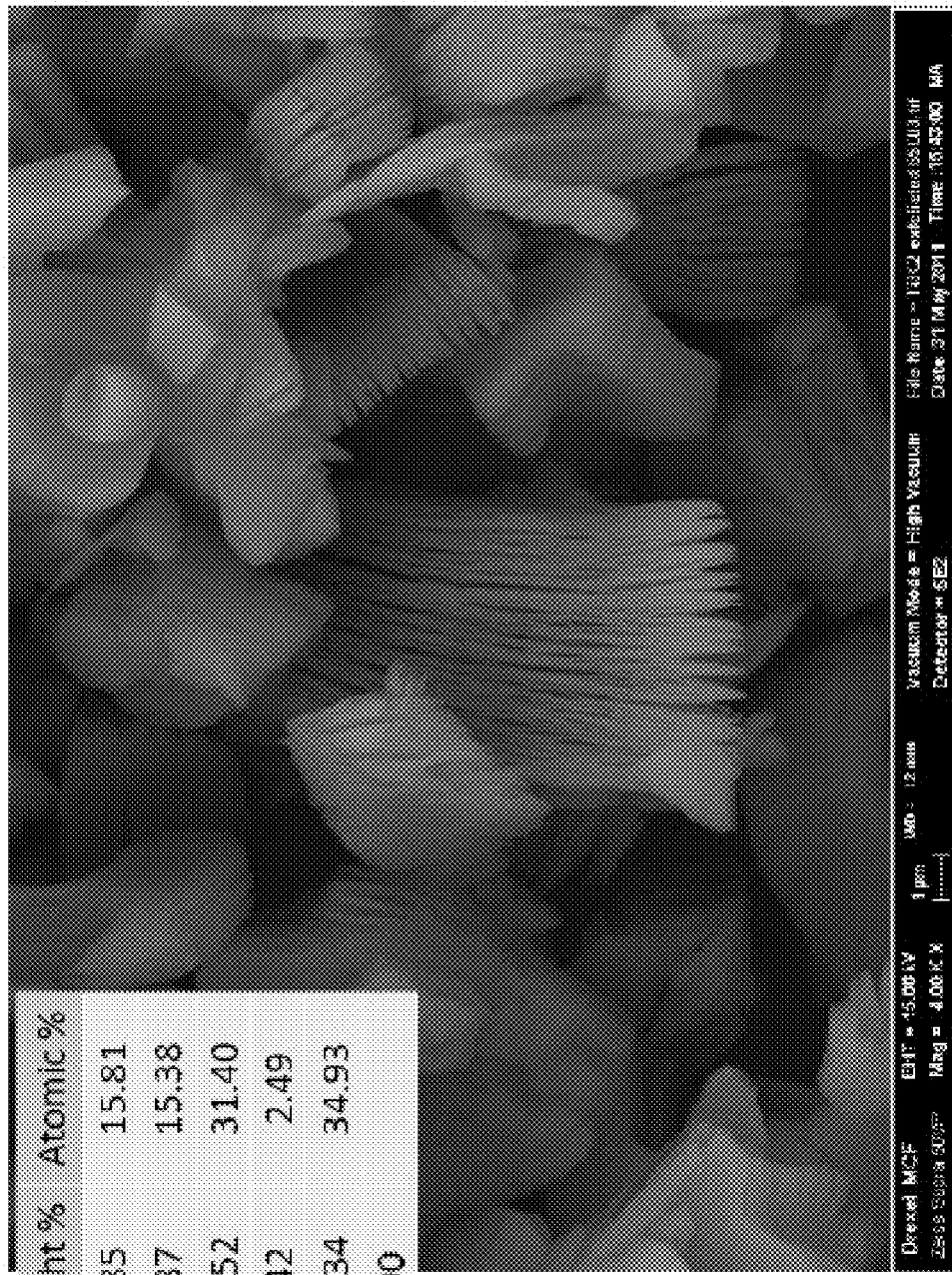
FIG. 17 shows SEM micrographs and EDX analytical results of chemically exfoliated $Ti_3AlC_2$ (10% HF 2 hours at 65° C.).
Figure 18B:
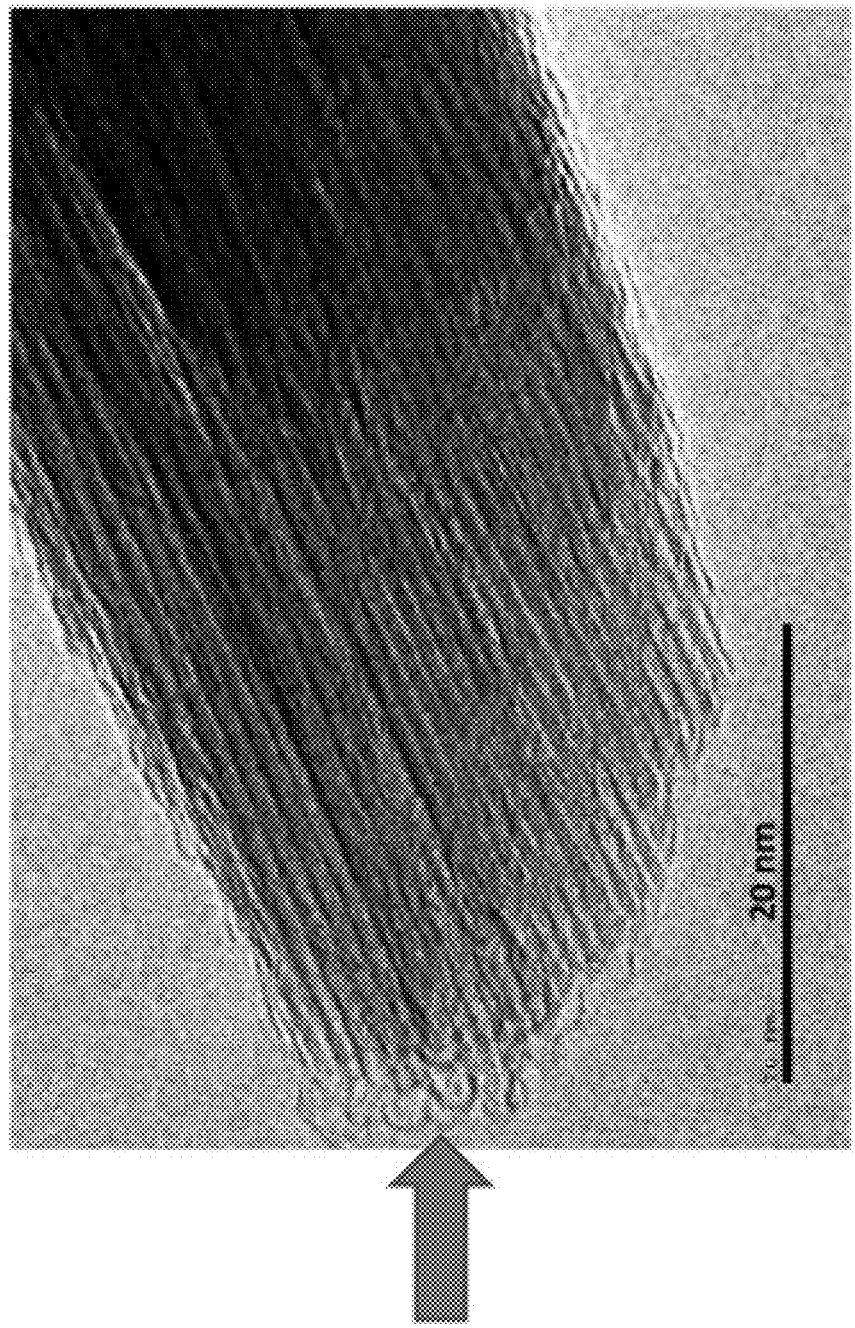
FIG. 18(b) is an enlargement of bottom micrograph of FIG. 18(a).
Figure 19:
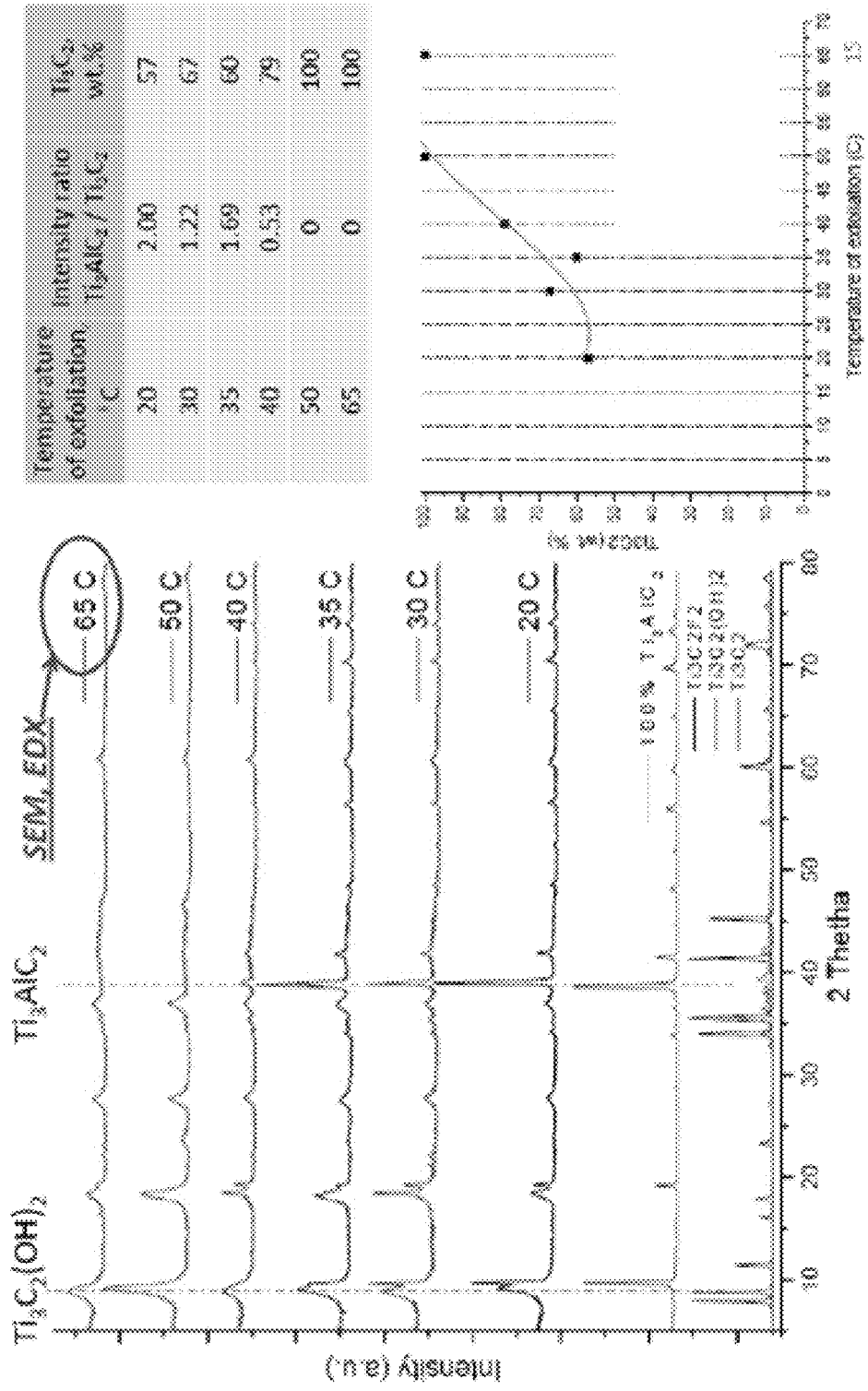
FIG. 19 shows XRD spectra for samples of chemically exfoliated $Ti_3AlC_2$, generated as a function of temperature in 50 wt % HF for 2 hours.
Figure 20:
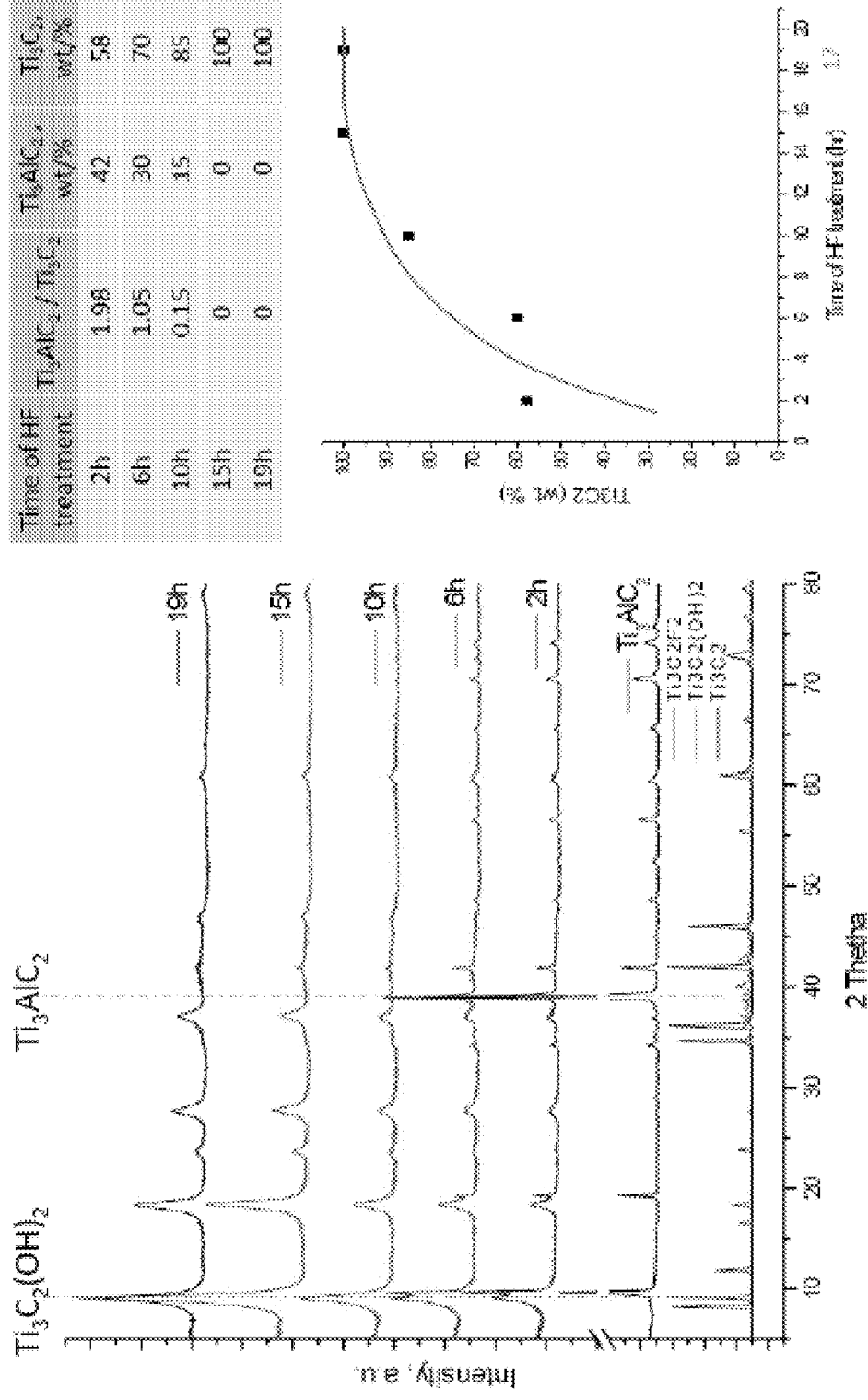
FIG. 20 shows XRD spectra for samples of chemically exfoliated $Ti_3AlC_2$, generated as a function of time in 50 wt % HF at room temperature.
Figure 22A:
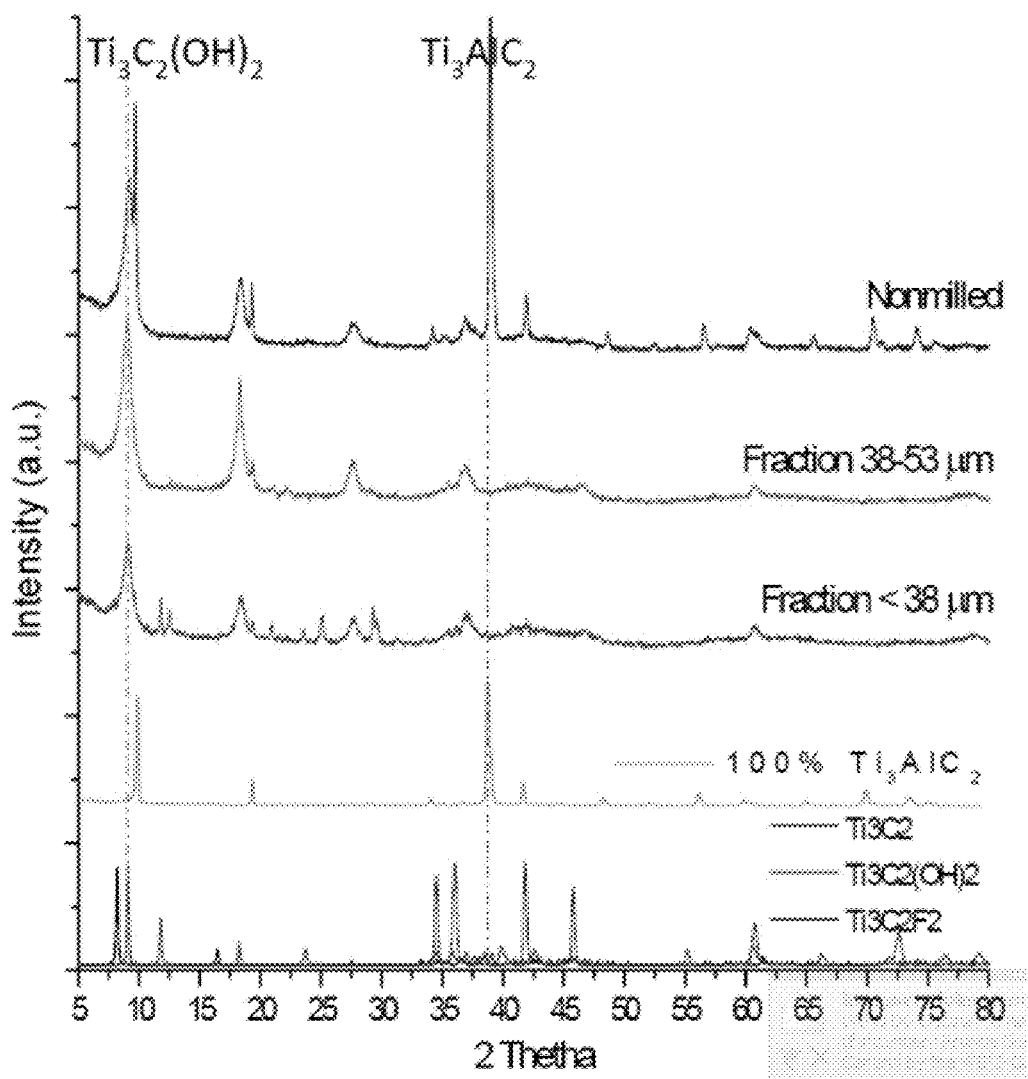
FIG. 22A shows XRD spectra for samples of chemically exfoliated $Ti_3AlC_2$, generated as a function of initial particle size of the MAX phase precursor. The materials were held for 2 hours in 50 wt % HF at room temperature.
Figure 22B:
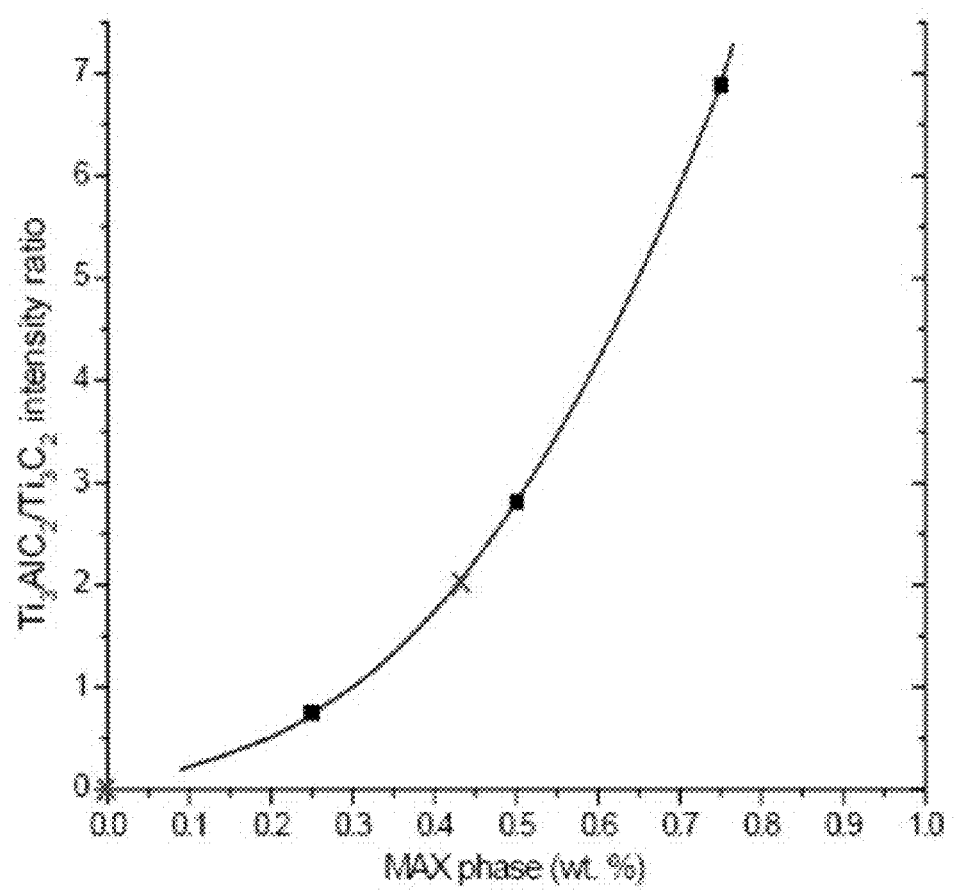
FIG. 22B shows corresponding intensity ratios as a function of MAX phase (wt %).
Figure 23:
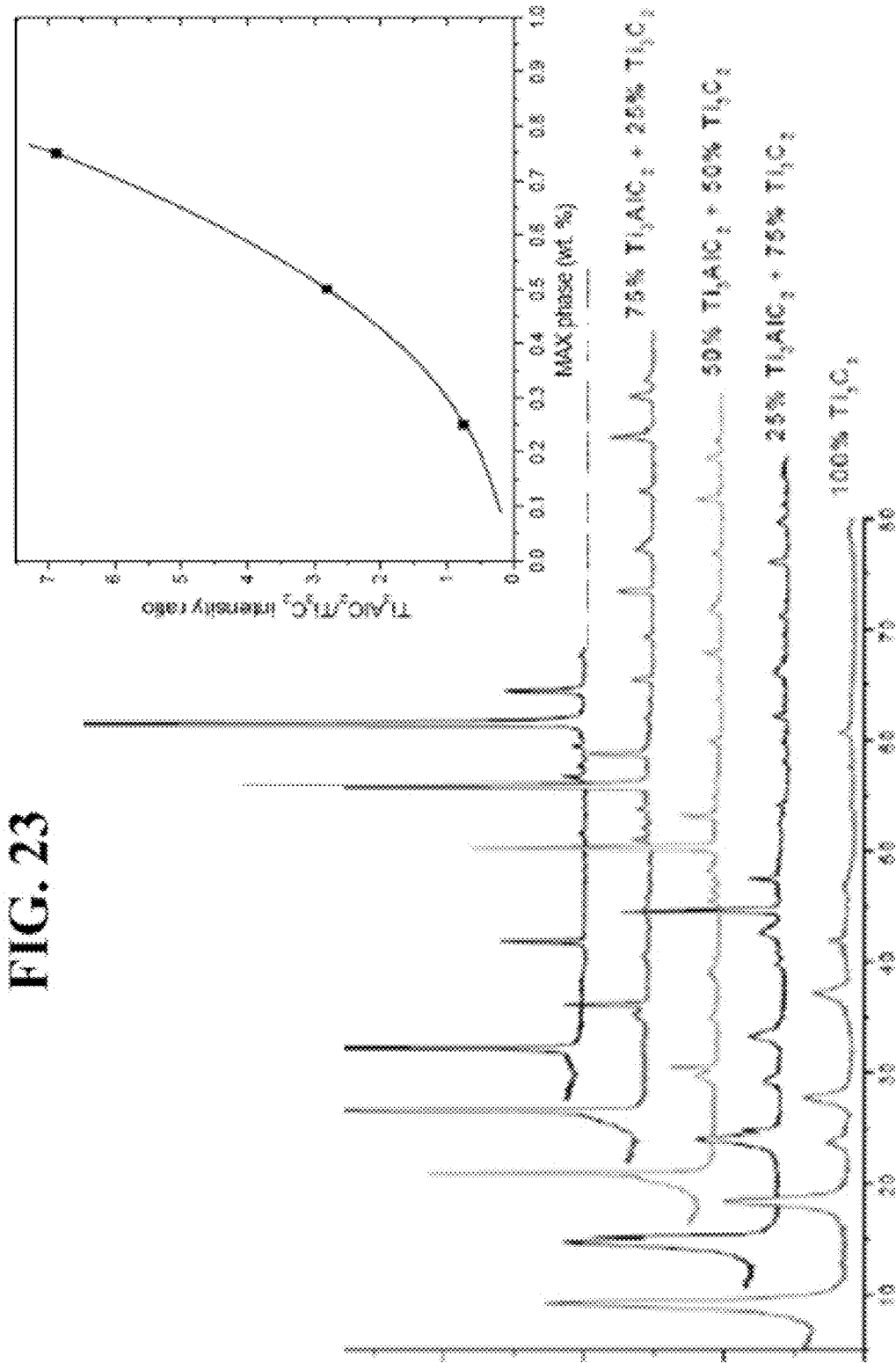
FIG. 23 shows XRD spectra forming the basis for a calibration curve of chemically exfoliated $Ti_3AlC_2$, generated as a function of composition.
Figure 24:
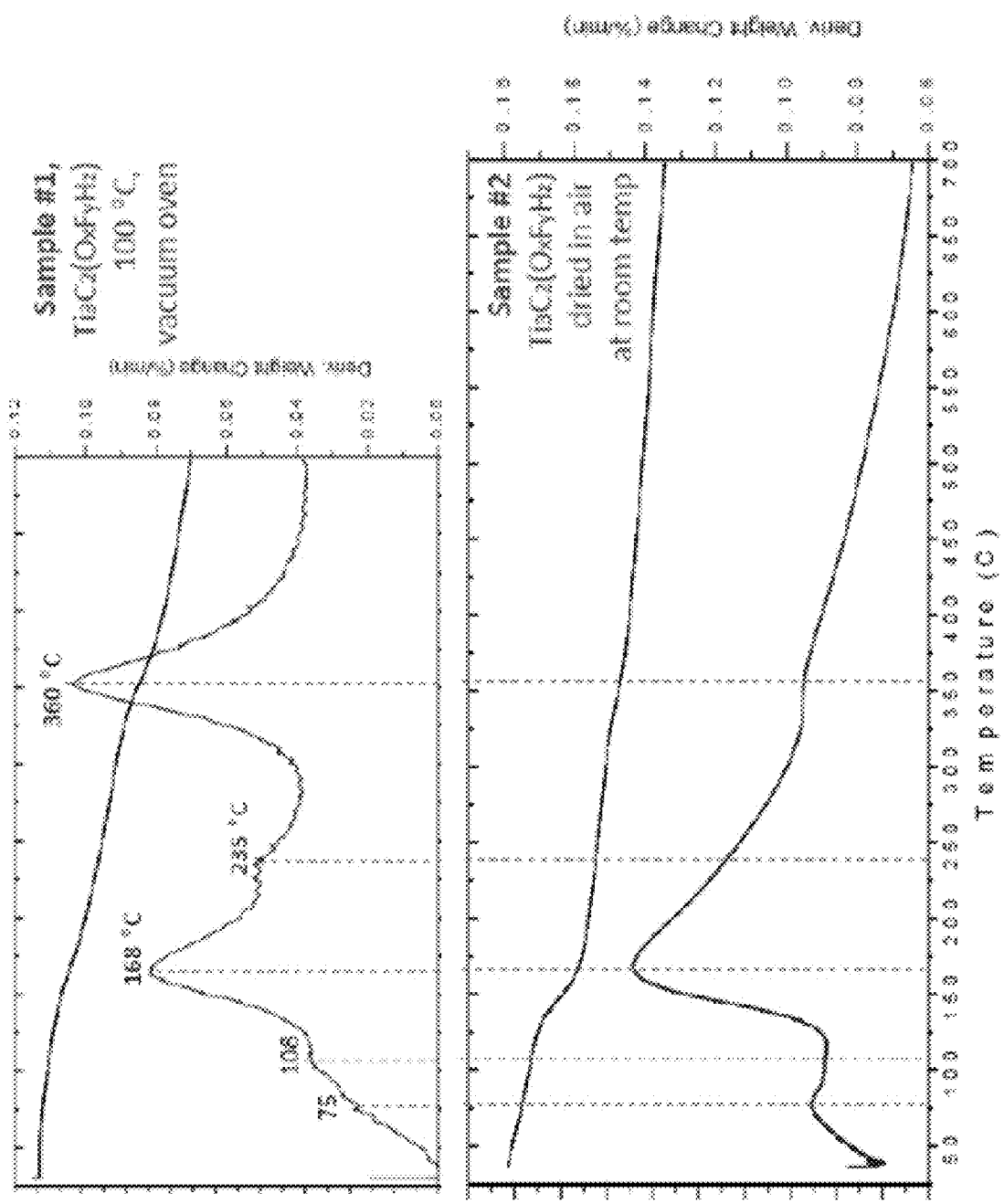
FIG. 24 shows TGA graphs for two samples of $Ti_3C_2(OH)_x(F)_y$ (alternatively, $Ti_3C_2T_s$) prepared at two different drying conditions

Experimental Characterization of the Product of the Reaction Between $(V_{1/2}Cr_{1/2})_3AlC_2$ and Aqueous HF—$(V_{1/2}Cr_{1/2})_3C_2(OH)_x(F)_y$ $(V_{1/2}Cr_{1/2})_3AlC_2$ powder was made by ball milling powders of 1.5V+1.5Cr+1.2Al+2C (molar ratios) for 12 hours, then heating the mixture under Ar to 1550° C., soaking at this temperature for 2 hours, and cooling to room temperature, after which a powder was obtained from the sintered mass using diamond coated milling bit. The powders were then exfoliated by stirring them in 50% aqueous HF at room temperature for 65 hr (5 gm powder in 50 mL acid). SEM micrographs and XRD spectra of the resulting materials are shown in FIGS. 14-16.

Example 7

Figure 11:
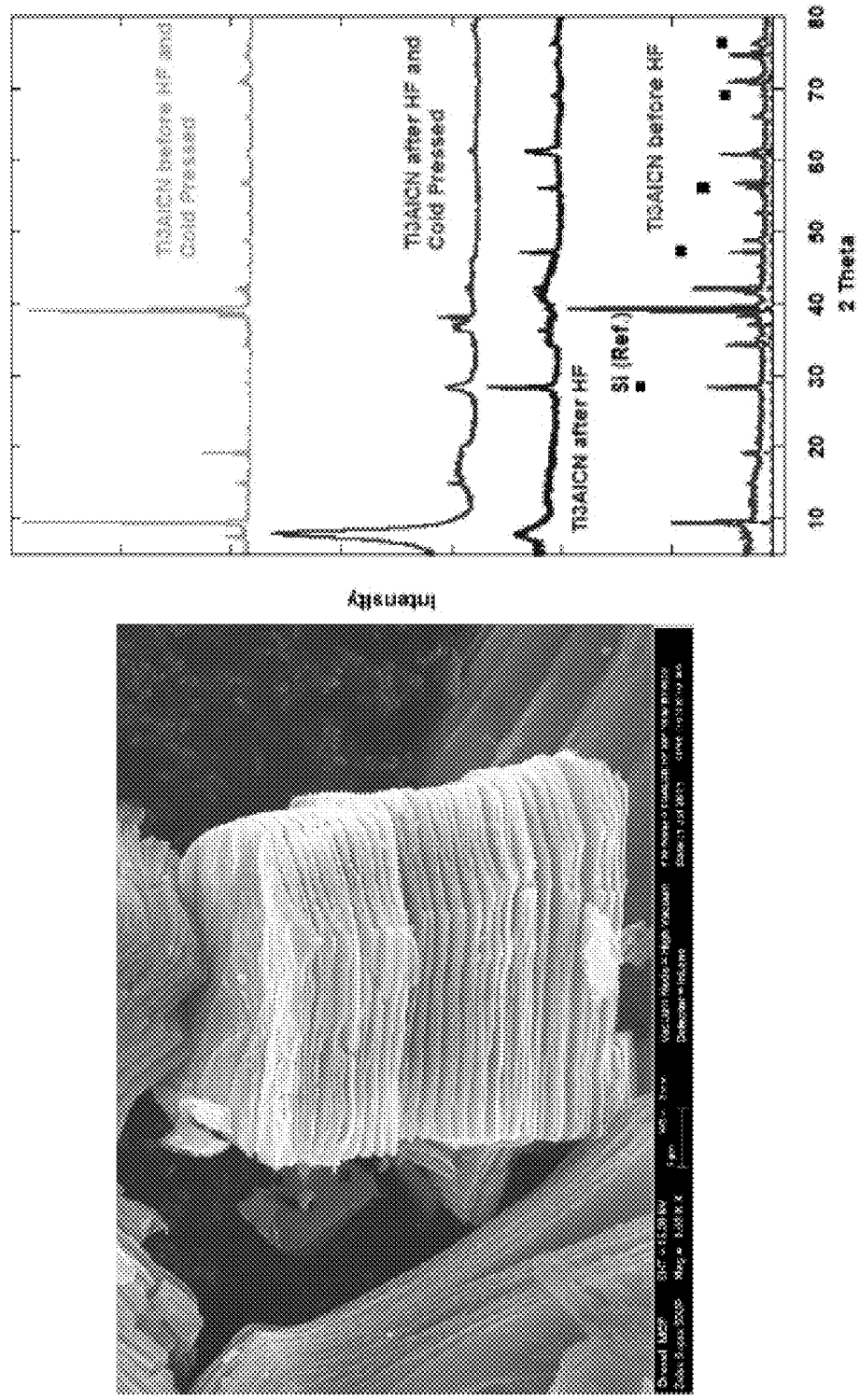
FIG. 11 shows SEM micrographs and XRD spectra of chemically exfoliated $Ti_3AlCN$ (30% HF 18 hours at RT).
Figure 12:
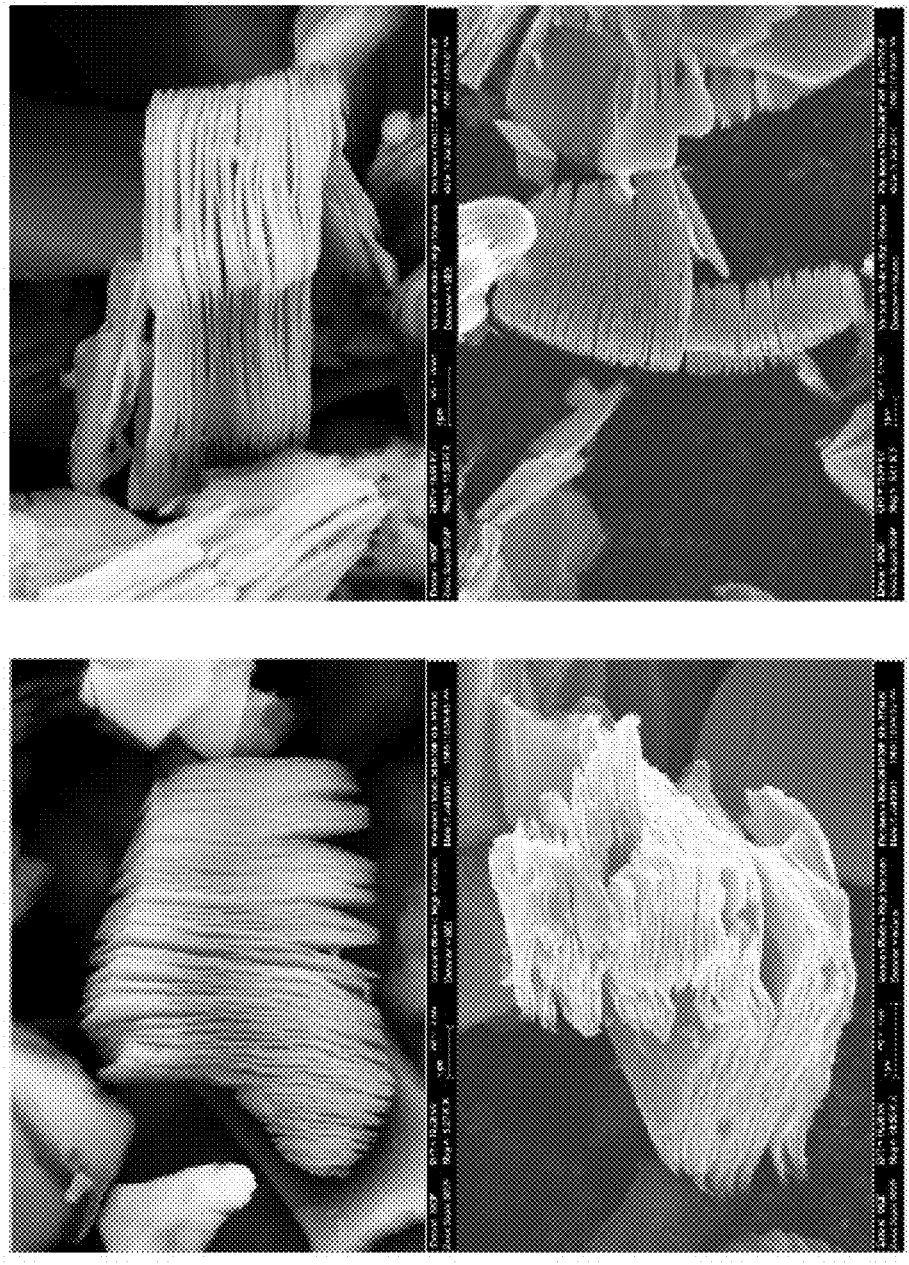
FIG. 12 shows additional SEM micrographs of chemically exfoliated $Ti_3AlCN$ (30% HF 18 hours at RT).
Figure 13:
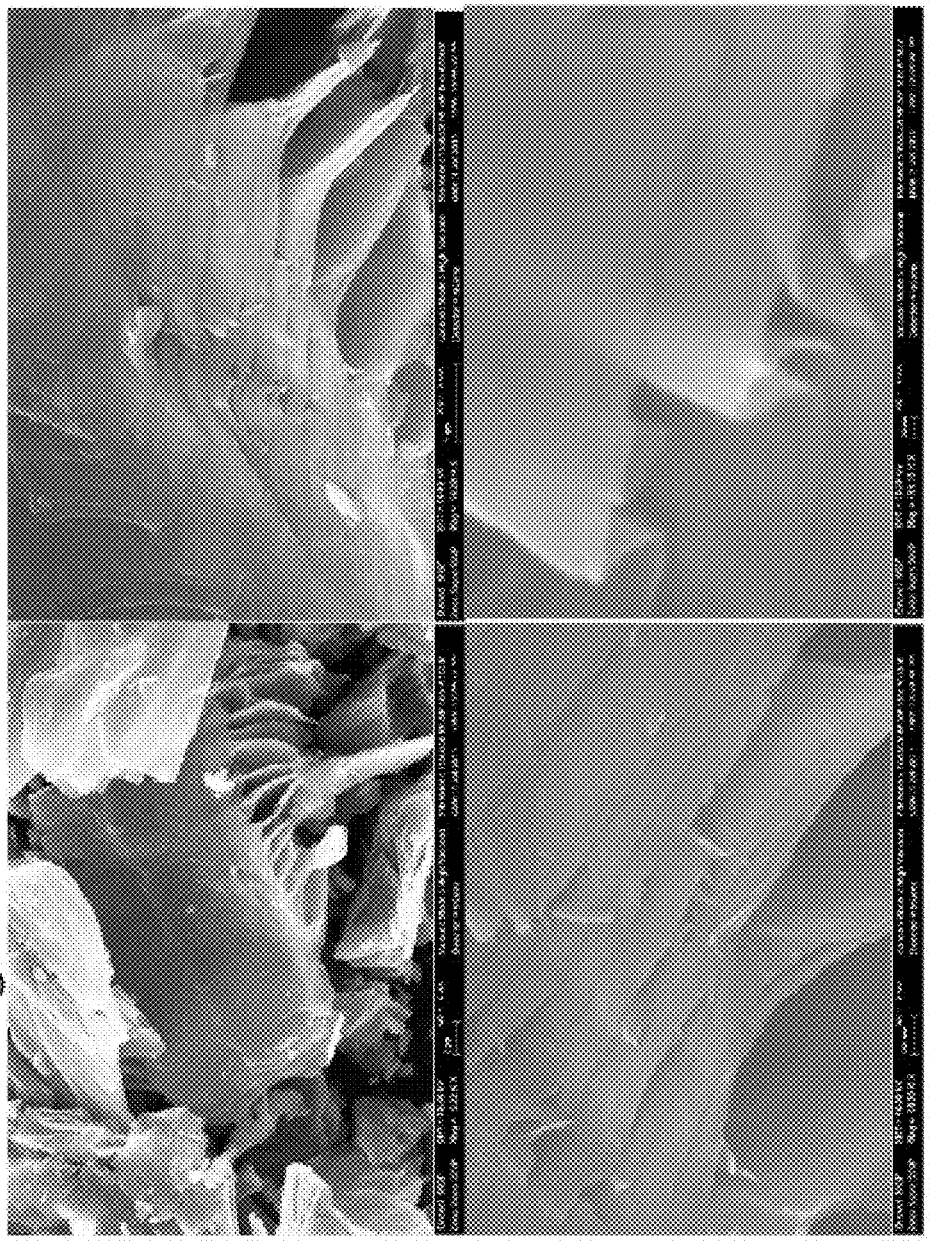
FIG. 13 shows additional SEM micrographs of chemically exfoliated $Ti_3AlCN$ (30% HF 18 hours at RT).

Experimental Characterization of the Product of the Reaction Between $Ti_3Al(CN)$ and Aqueous HF—$Ti_3(CN)(OH)_a(F)_b$ $Ti_3Al(CN)$ powder was prepared was made by ball milling Ti:AlN:C=3:1:1 (molar ratios) for 12 hours, then heating the mixture at 10° C./min to 1500° C., holding 2 hours, then cooling, all under Argon (C and Ti powders were purchased from Alfa Aesar, Ward Hill, Mass.). AN powder was purchased from Sigma-Aldrich. The resulting material was crushed using mortar and pestle. The resulting powder was immersed and stirred in 30% concentrated hydrofluoric acid, HF, (Fisher Scientific, Fair Lawn, N.J.) solution at room temperature for 18 h. The resulting suspension was then washed several times using deionized water and centrifuged to separate the powders. SEM micrographs and XRD spectra of the resulting materials are shown in FIGS. 11-13.

Example 8

Effect of Chemical Exfoliation Processing Conditions on Formation and Yield of MXene Compositions Starting with $Ti_3AlC_2$ powders as a representative material, a series of experiments were conducted to determine the effects of various process parameters on the chemical exfoliation of MAX phase materials to form the corresponding MXene compositions. In evaluating the effect of temperature on exfoliation, $Ti_3AlC_2$ powders were stirred in 50% aqueous HF for 2 hours at different temperatures (e.g., 20, 30, 40, 50, and 65° C.). The effect of processing time was studied by stirring $Ti_3AlC_2$ powders with 50% aqueous HF for 2 hours at room temperature over the time range of 2 to 19 hours. In testing the effect of initial particle size, $Ti_3AlC_2$ powders were crushed in ball milling machine and separated with sieves first, then exfoliated by stirring with 50% aqueous HF at room temperature for 2 hours. FIGS. 19, 20, 21, and 22 illustrate the effect of HF temperature, time of treatment, and initial particle size, respectively. The specific conditions employed, where different than those described above, are provided in each figure.

TABLE 1

List of MAX Phases Exfoliated in This Work and Exfoliation Process Parameters[a]

| Compound | HF Conc (%) | Time (hr) | c lattice constant (nm) Before HF | c lattice constant (nm) After HF | Domain size (nm) | Yield (wt %) |
|---|---|---|---|---|---|---|
| $Ti_2AlC$ | 10 | 10 | 1.36 | 4.504 | 6 | 60 |
| $Ta_4AlC_3$ | 50 | 72 | 2.408 | 3.034 | 38 | 90 |
|  |  |  |  | 2.843 | 18 |  |
| TiNbAlC | 50 | 28 | 1.379 | 1.488 | 5 | 80 |
| $(V_{0.5}Cr_{0.5})_3AlC_2$ | 50 | 69 | 1.773 | 2.426 | 28 | NA |
| $Ti_3AlCN$ | 30 | 18 | 1.841 | 2.228 | 7 | 80 |
| $Ti_3AlC_2$ | 30 | 2 | 1.842 | 2.051 | 11 | 100 |
| $Nb_2AlC$ | 50 | 90 | 1.388 | 2.234 | 5 | 100 |
| $Nb_4AlC_3$ | 50 | 90 | 2.419 | 3.047 | 27 | 100 |
| $V_2AlC$ | 50 | 90 | 1.313 | 1.973 | 10 | 60 |
| $Mo_2GaC$ | 50 | 96 | 1.317 | 2.021 | 15 | NA |

[a]The particle size for all MAX phases was <35 μm prior to exfoliation. The effects of HF treatment on the c lattice constant and the average domain size along [0001] deduced from the FWHM and the Scherrer formula are listed. The penultimate column shows the estimated process yields.

Example 9

Figure 25:
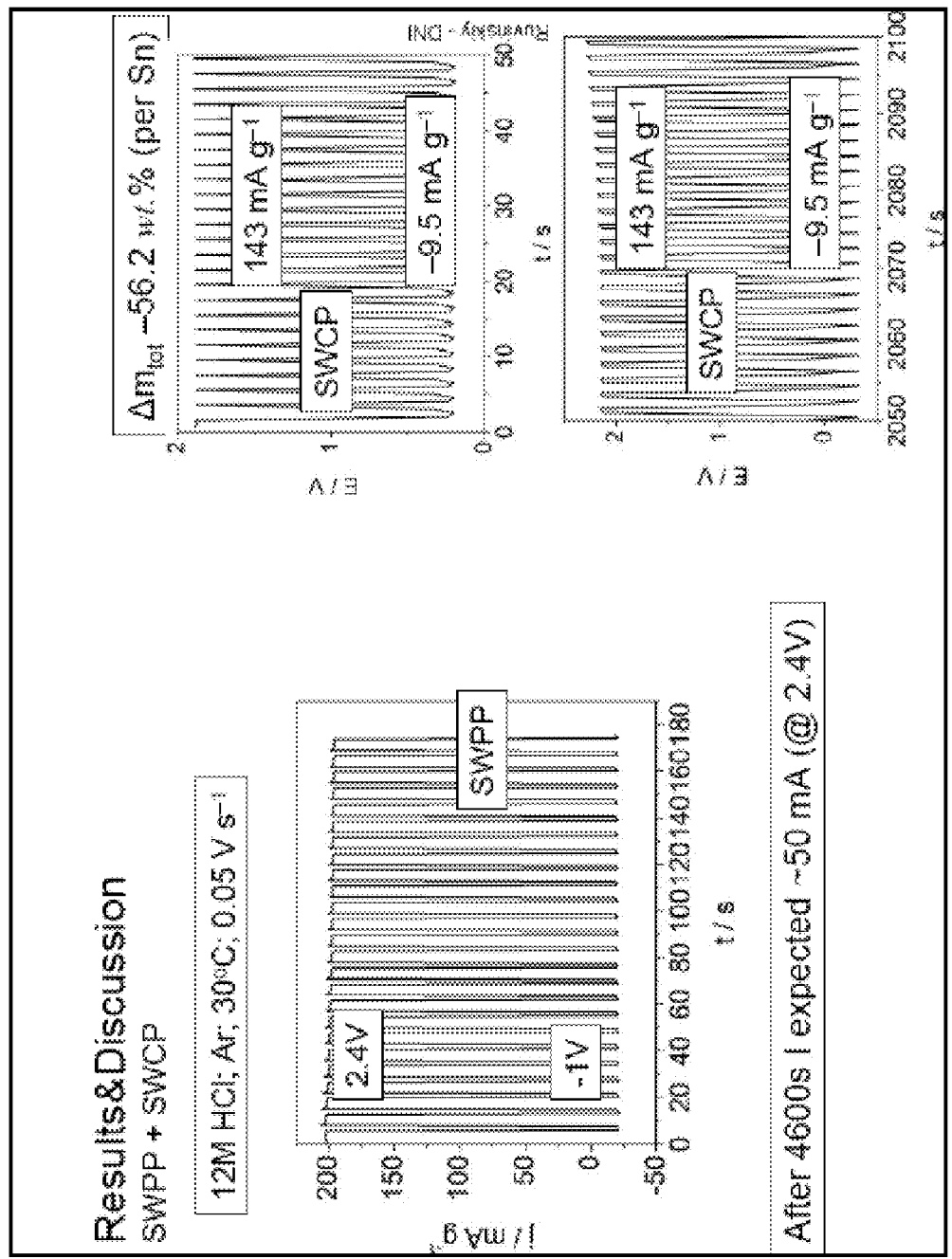
FIG. 25 shows exemplary experimental parameters for tests to evaluate the electrochemical exfoliation of MAX phase materials; see Example 9.

Preparation of MXene Compositions by the Electrochemical Exfoliation of MAX Phase Materials $Ti_2SnC$ was made by ball milling 2Ti+Sn+C (molar ratios) for 12 hr, then heating the mixture at a ramp rate of 10° C./minute to 1250° C., holding for 2 hours and cooling to room temperature, all under Ar atmosphere. The resulting material was crushed using mortar and pestle to form a powder (Ti, Sn, and C powders were purchased from Alfa Aesar, Ward Hill, Mass.). Exfoliation of $Ti_2SnC$ was demonstrated by selectively electrochemically removing Sn upon application of a repeated sequence composed of a short cathodic polarization (either potentiostatic or galvanostatic) followed by a long anodic polarization (either potentiostatic or galvanostatic) to an electrochemical system (see FIG. 25 for a representative set of conditions; SWPP=square wave potential polarization; SWCP=square wave current polarization. $\Delta m_{tot}$ refers to the loss in sample weight as a result of the electrochemical treatment). In this system, a hot pressed sample of $Ti_2SnC$ was used as the anode, and Pt was used as the reference and working electrode. The electrolyte was either aqueous 5 M or 12 M HCl, and high purity Ar gas was constantly purged through the working solution to maintain an inert atmosphere.

Figure 26:
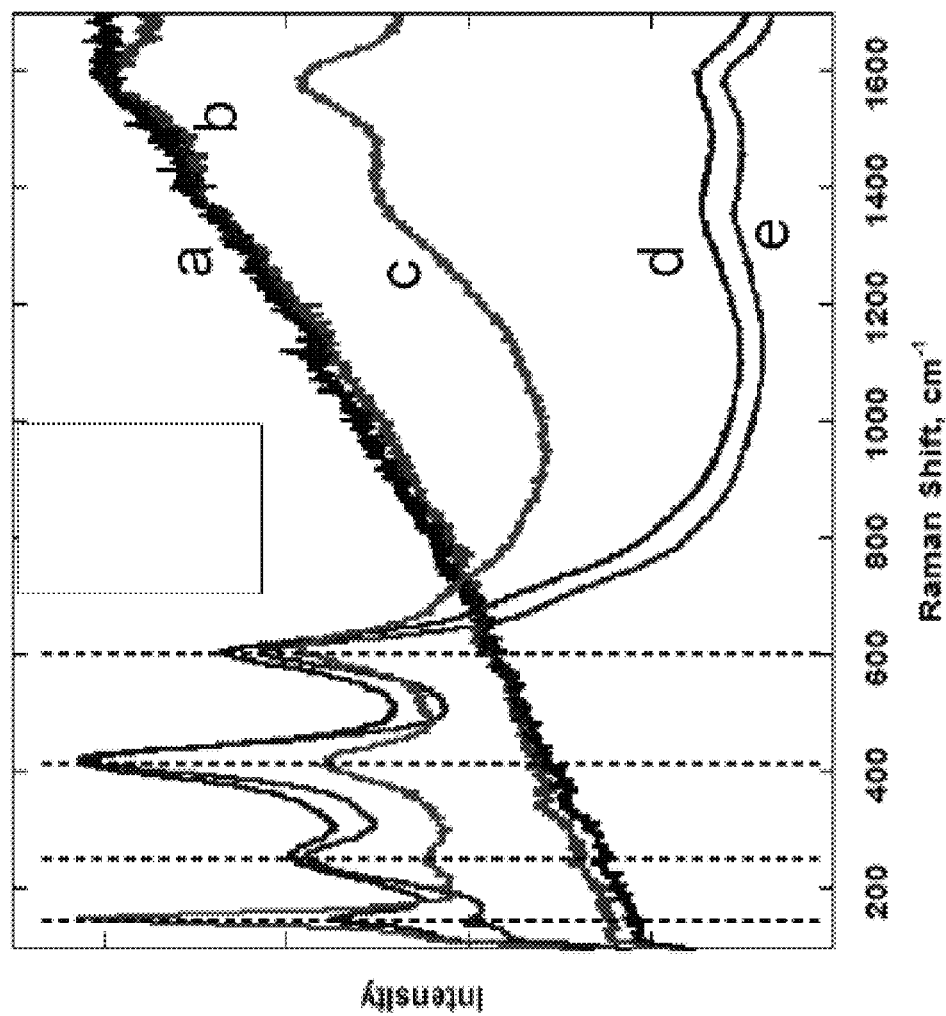
FIG. 26 shows a series of Raman spectra for samples obtained in tests described in Example 8. Curves (a) and (b) are the spectra of the exfoliated material obtained after the electrochemical anodic polarization treatment of the $Ti_2SnC$ MAX phase in 12 M HCl. Curves (c) through (e) are the initial spectra of $Ti_2SnC$.
Figure 27:
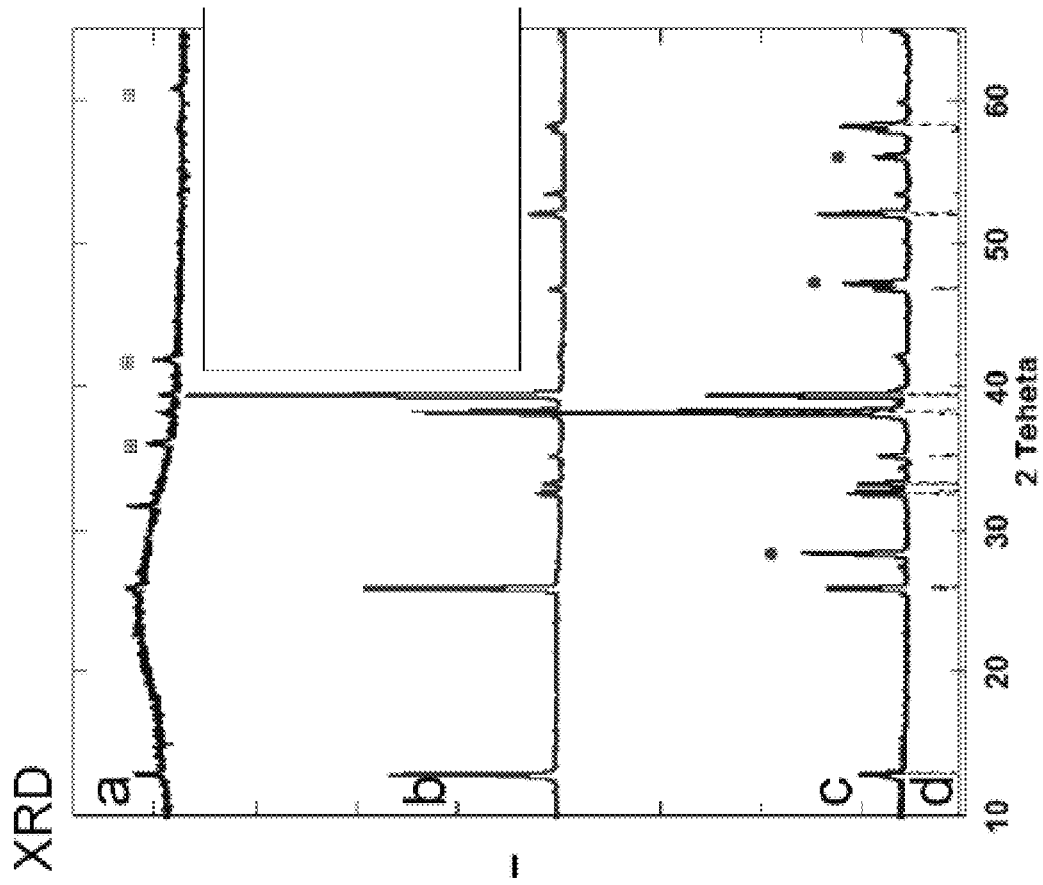
FIG. 27 shows the XRD data of the exfoliated material: (a) obtained after the electrochemical anodic polarization treatment of the $Ti_2SnC$ MAX phase in 12 M HCl. (b) the XRD data of the initial $Ti_2SnC$ material. (c) the XRD data of the $Ti_2SnC$ material treated in Ar as 1250° C. (d) a simulated XRD pattern for the $Ti_2SnC$ system. Note: the asterisks and crossed boxes mark the characteristic peak positions of $Si_{pc}$ and TiC, respectively.
Figure 28A:
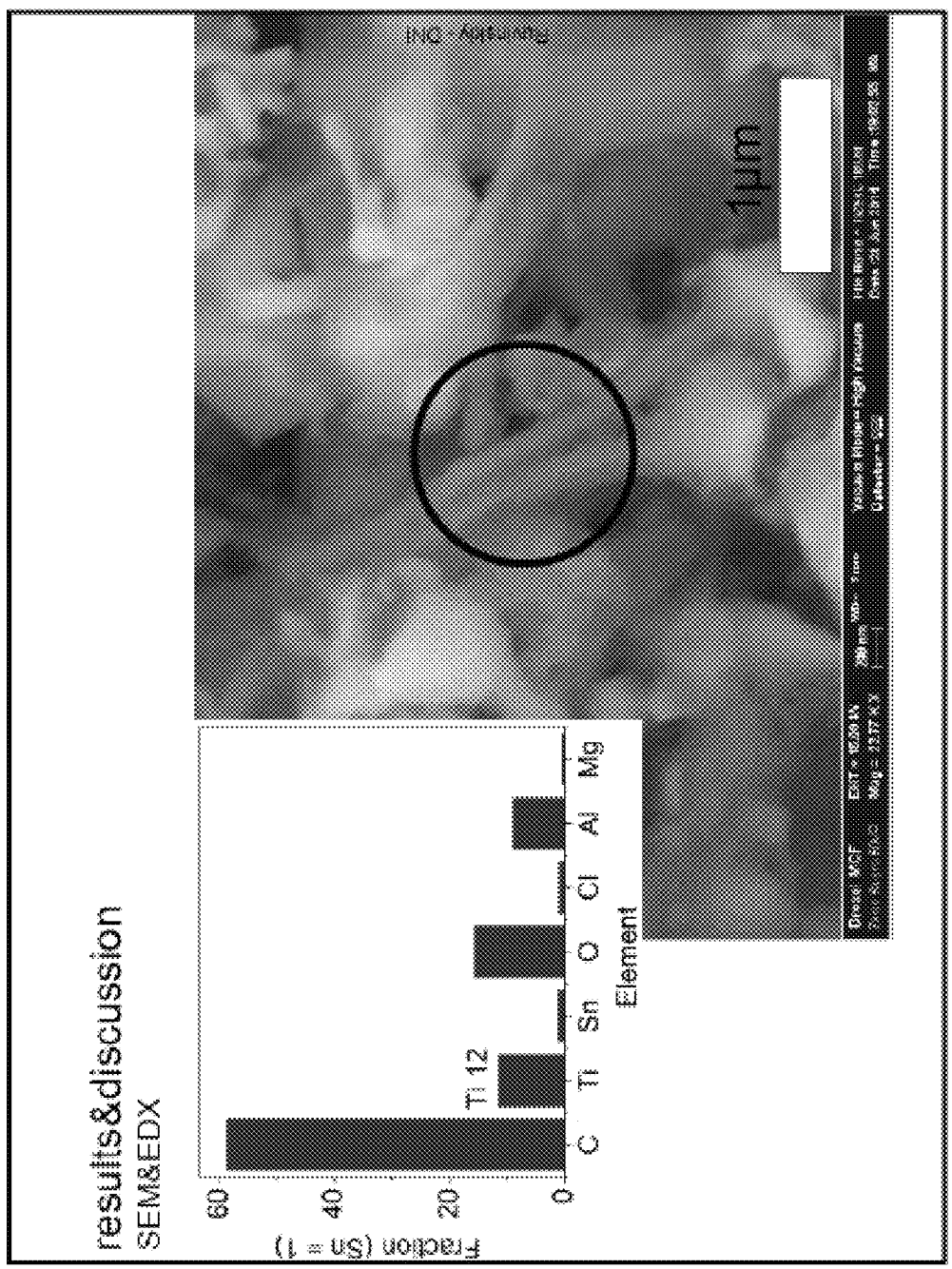
FIGS. 28A-C show SEM and EDX/EDS data of the exfoliated material obtained after the electrochemical anodic polarization treatment of the $Ti_2SnC$ MAX phase in 12 M HCl. The circles represent the approximate area subjected to EDX/EDS analysis.
Figure 28B:
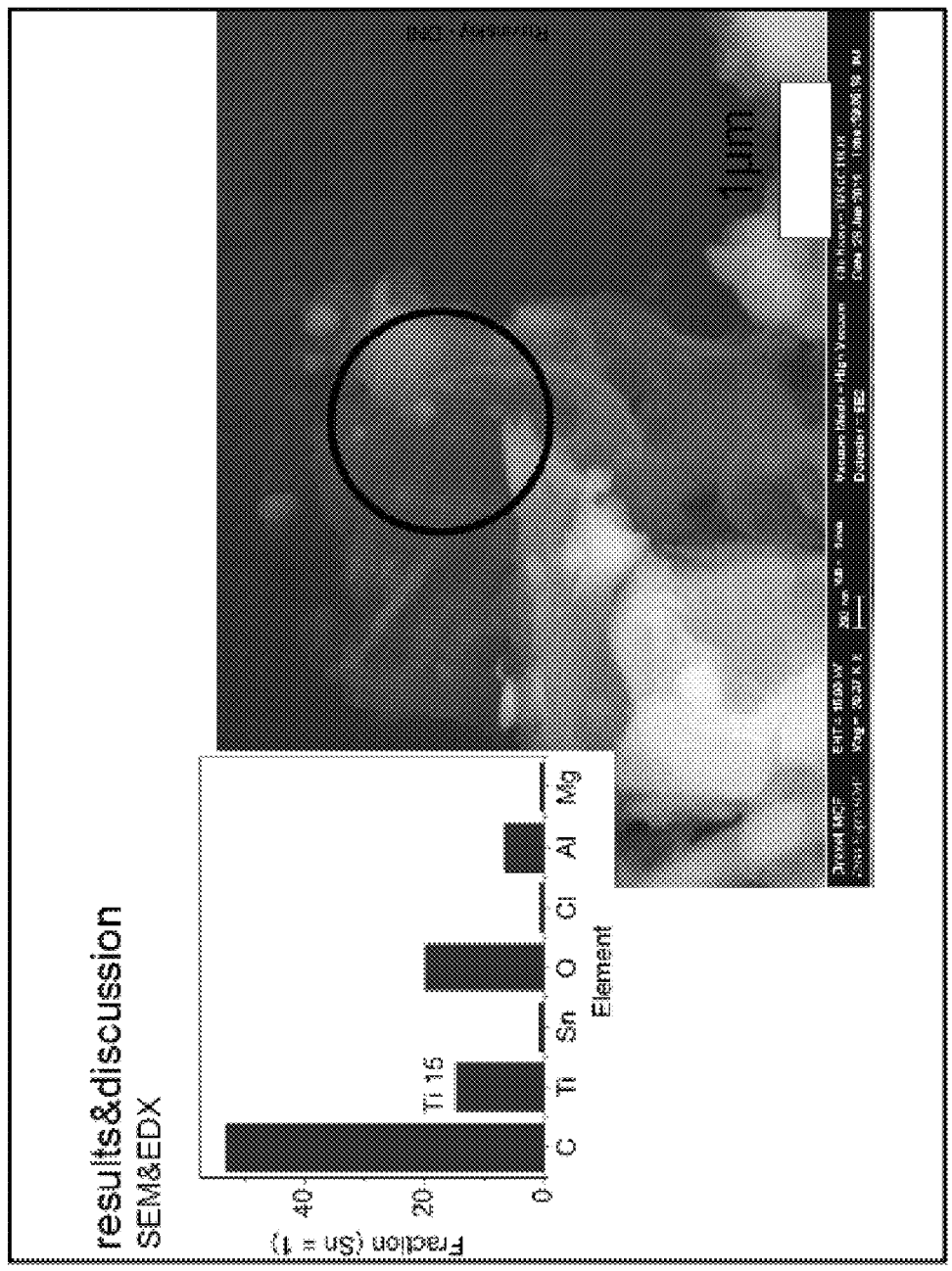
Figure 28C:
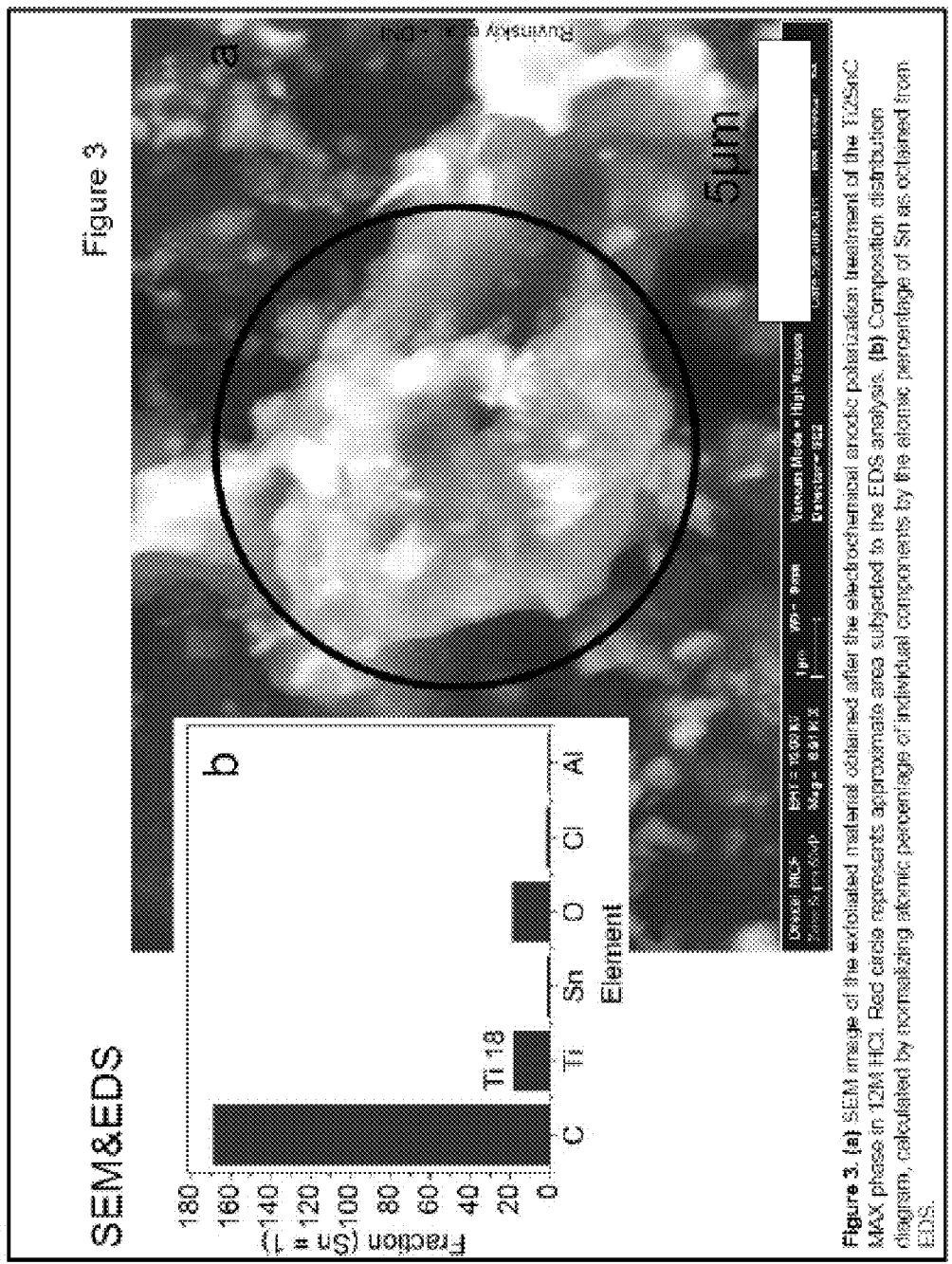

The rapid electrochemical corrosion of the anode material resulted in the formation of a finely dispersed powder which was collected at the bottom of the reaction vessel, washed with deionized water, and dried. The dried powder was subjected to a series of tests, the results of which are shown in FIGS. 25-28. FIG. 26 shows the dramatic difference in Raman spectra between the product (curves a and b) and the starting material (curves c-e), consistent with the changes seen in other similar transformations (compare, for example, the curves in FIG. 4(b)). Similarly, changes in the XRD spectra (FIG. 27) are indicative of the absence of starting material. Finally, EDX spectra shown in FIG. 28(A-C) show that the powder is devoid of appreciable Sn, confirming its elimination (Note: the presence of O in these EDX spectra is consistent with a surface coating of the MXene comprising oxide or hydroxide. The presence of Si in the spectra is attributed to the substrate used in the measurement.

Example 10

Intercalation of Lithium and Use of $Ti_3C_2$ in Batteries

Figure 29B:
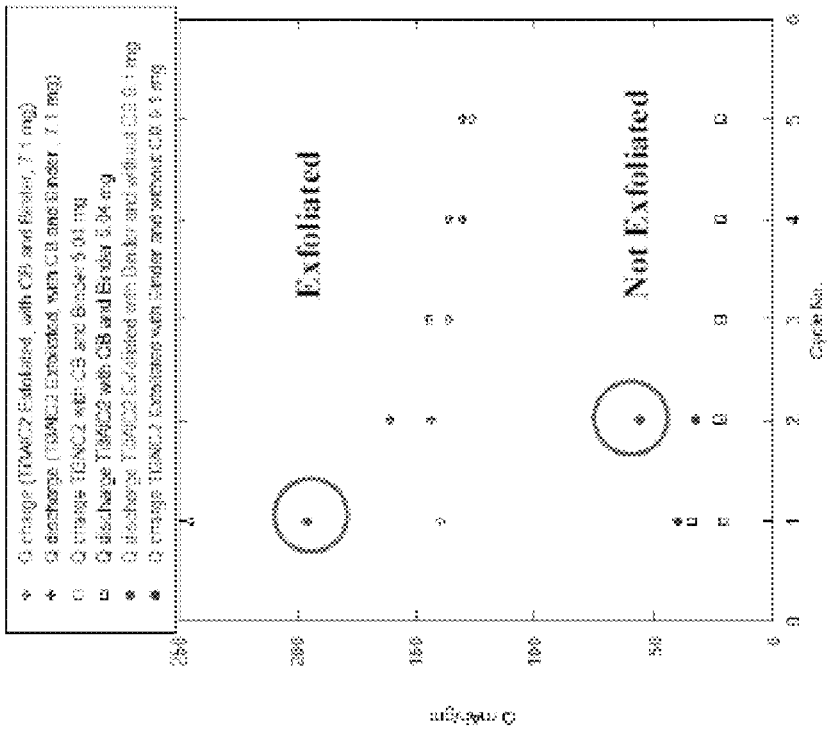
FIG. 29(a) shows the results of electrochemical testing described in Example 10. The labels "Exfoliated" and "Not Exfoliated" refer to the samples used in the testing corresponding to exfoliated and not exfoliated particles of $Ti_3AlC_2$

The electrochemical behavior of MXene compositions (exfoliated MX phase compositions) was compared to the corresponding MAX phase material in lithium ion battery tests. [The electrolyte used was a mixture of ethylene carbonate and dimethyl carbonate (EC/DMC) with lithium hexafluorophosphate ($LiPF_6$). After cell assembly inside a glove box, both Galvanostatic (GV) and Cyclic Voltammetry (CV) tests were used to study the electrochemical behavior of MAX phases in Li batteries. These electrochemical tests were carried out using a BioLogic VMP-4 potentiostat/galvanostat.] Electrodes were prepared using MAX phase and MXene compositions in a number of electrode configurations, including (a) cold pressed electrode with neither binder nor carbon black; (b) film of powder on copper foil with binder and without carbon black; (c) film f powder on copper foil with binder and carbon black; and (d) film of carbon black alone with a polyvinylidene-difluoride, PVDF, binder. CV and GV techniques were used to characterize the electrochemical nature of the resulting electrodes/cells. FIG. 29(A/B) shows the results where the performance of electrodes prepared using carbon black (CB) and binder, comparing the additional presence of $Ti_3AlC_2$ and exfoliated $Ti_3AlC_2$; i.e., MXene $Ti_3C_2(OH)_x(F)_y$. As shown in FIG. 29, the capacity of the MXene containing compositions showed significantly higher capacity an order of magnitude higher) than a comparable electrode made from the corresponding MAX phase material. It is known that lithium capacity in MAX phase materials is extremely low, owing to the lack of space between the layers into which ions may migrate. The significant increase in capacity with the electrodes containing the MXene composition results are consistent with the migration/intercalation of lithium within the stacked layers of MXene Example 11

Intercalation of Lithium and Use of $Ti_2C$ in Batteries

Testing comparable to that described in Example 10 with $Ti_3C_2$ (derived from $Ti_3AlC_2$) was also done with $Ti_2C$ derived from $Ti_2AlC$. As described below, testing demonstrated the insertion of Li into a new two-dimensional (2-D) layered $Ti_2C$-based material (MXene) with an oxidized surface, formed by etching Al from $Ti_2AlC$ in HF at room temperature. Nitrogen sorption of treated powders showed desorption hysteresis consistent with the presence of slit-like pores. At 23 $m^2 \cdot g^{-1}$, the specific surface area was an order of magnitude higher than untreated $Ti_2AlC$. Cyclic voltammetry exhibited lithiation and delithiation peaks at 1.6 V and 2 V vs. $Li^+$/Li, respectively. At C/25, the steady state capacity was 225 $mAh \cdot g^{-1}$; at 1 C, it was 110 $mAh \cdot g^{-1}$ after 80 cycles; at 3 C, it was 80 $mAh \cdot g^{-1}$ after 120 cycles; at 10 C, it was 70 $mAh \cdot g^{-1}$ after 200 cycles.

Pre-reacted, −325 mesh, $Ti_2AlC$ powders were commercially obtained (3-ONE-2, Voorhees, N.J., >92 wt. % purity). The exfoliation process was carried by immersing the $Ti_2AlC$ powder in diluted (10%) hydrofluoric acid, HF, (Fisher Scientific, Fair Lawn, N.J.) for 10 h at room temperature, as described above. The materials were characterized by SEM (Zeiss Supra 50VP, Germany), EDS (Oxford *Inca* X-Sight, Oxfordshire, UK), and gas sorption analysis (Quantachrome Autosorb-1 with $N_2$ adsorbate) as described above (i.e., samples were outgassed under vacuum at 200° C. for 48 h. Nitrogen sorption analysis at 77 K was used for calculating the specific surface area (SSA) using the Brunauer-Emmet-Teller (BET) equation).

Figure 30A:
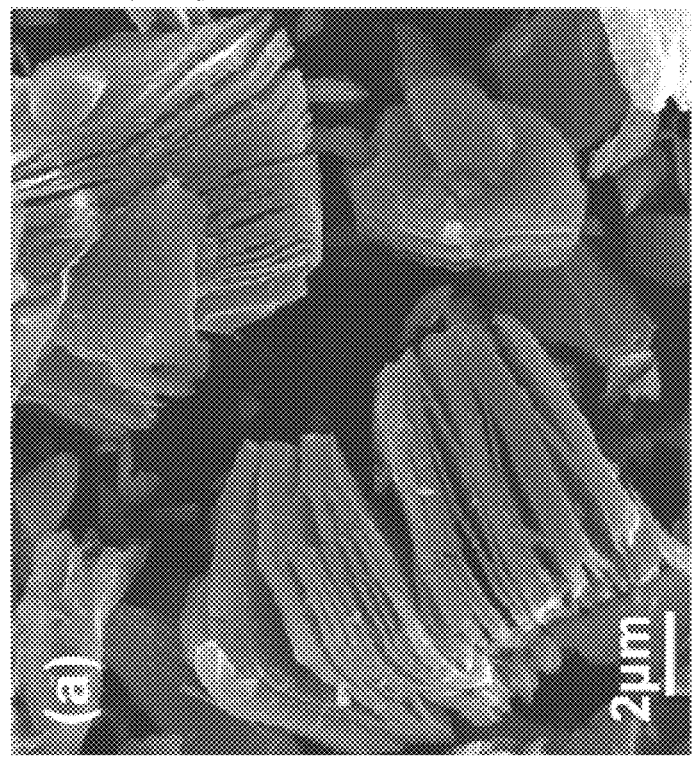
FIG. 30A shows an SEM image of exfoliated $Ti_2CO_x$ produced by HF treatment of $Ti_2AlC$.

X-ray diffraction, XRD, of the reacted powders indicated that the Al was selectively etched from the structure. EDS confirmed that the Al layers were replaced by O and F. SEM images of $Ti_2AlC$ particles after HF treatment (FIG. 30(a)) resemble images of exfoliated graphite and clearly show HF-induced delamination that are typical of MXenes.

Figure 30B:
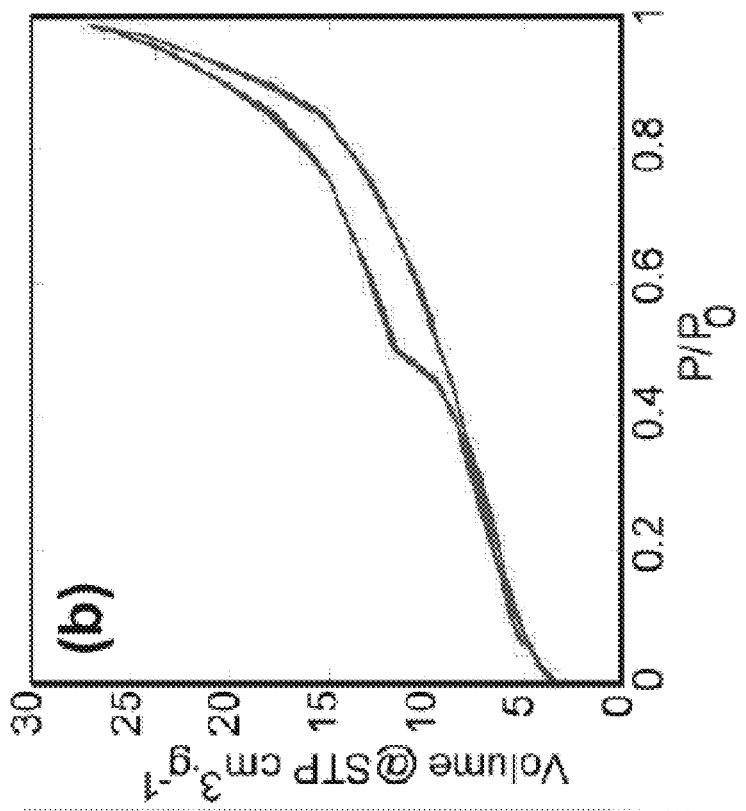
FIG. 30B shows $N_2$ adsorption-desorption isotherms of the material shown in FIG. 30(a), circles refer to adsorption and squares refer to desorption. The calculated SSA is approximately 23 m².g⁻¹.

The $N_2$ sorption isotherm of the treated powders (FIG. 30(b)) has a hysteresis loop with indications of the presence of mesopores and a shape typical for slit pores. The SSA calculated using the BET equation, for the HF treated $Ti_2AlC$ was 23 $m^2 \cdot g^{-1}$. This value is about an order of magnitude times higher than the as-received $Ti_2AlC$ powders measured at ≈2.5 $m^2 \cdot g^{-1}$.

The electrochemical behavior of exfoliated $Ti_2AlC$ in Li batteries was investigated using coin cells (CR 2016) prepared as follows. The working electrodes were made with 80 wt % $Ti_2C$ (as described above) and 10 wt. % Super P carbon black mixed with 10 wt. % Poly(vinylidene fluoride) dissolved in 1-Methyl-2-pyrrolidinone. The mixture was then spread onto a copper foil and dried at ca. 200° C. for 12 h, under a mechanical vacuum. CR 2016 coin-type cells were assembled using MXene as the positive electrode and Li metal foil as the negative electrode, separated by a sheet of borosilicate glass fiber (Whatman GF/A) separator saturated with 1 M $LiPF_6$ solution in a 1:1 weight mixture of ethylene carbonate and diethyl carbonate (EC:DEC) as the electrolyte. The cells were assembled inside an Ar-filled glove box with $H_2O$ and $O_2$ contents <1 ppm, to avoid any moisture contamination.

The cells were subjected to cyclic voltammetry and galvanostatic charge-discharge cycling using a potentiostat (VMP4, Biologic, S.A.). Electrochemical characterization was typically performed between 0.05 V and 2.5 V vs. $Li^+$/Li.

Figure 31A:
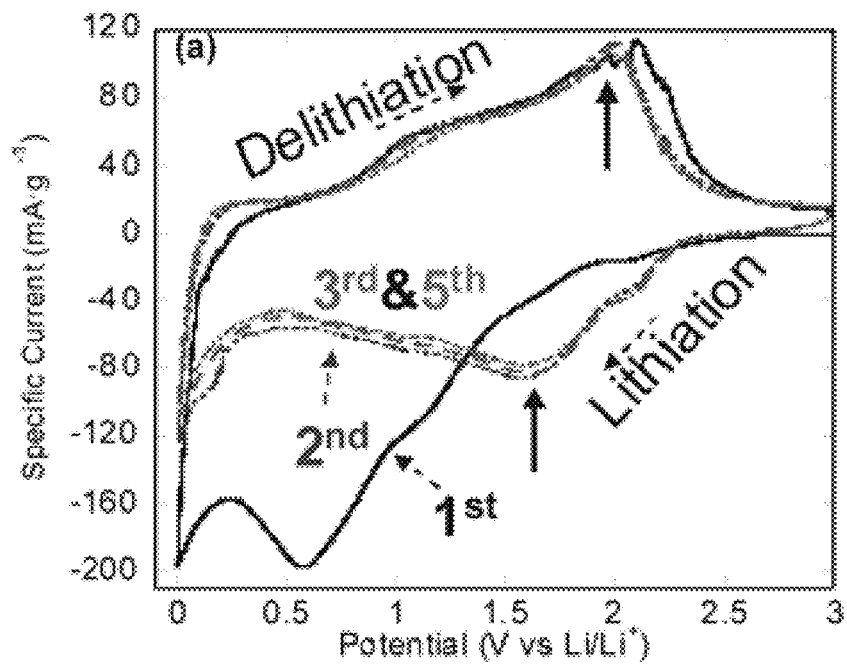
FIG. 31(A) shows cyclic voltammetry curves of exfoliated $Ti_2C$ (alternatively, $Ti_2CT_s$) at a constant scan rate of 0.2 mV·s⁻¹. The solid arrows refer to main peaks positions during lithiation and delithiation cycles.

Typical cyclic voltammetry curves, at a rate of 0.2 $mV \cdot s^{-1}$, for the exfoliated $Ti_2C$ are shown in FIG. 31(a). A broad, irreversible peak was observed around 0.6 V, during the first lithiation cycle (reduction); it was absent in subsequent cycles. This irreversible peak was assigned to the formation of a solid electrolyte interphase (SEI) and to an irreversible reaction with the electrode material. In all subsequent cycles, broad reversible peaks were observed at 1.6 V and 2.0 V vs. $Li^+$/Li during lithiation and de-lithiation, respectively. Because these peak potentials are similar to those reported for $TiO_2$ and lithiated titania, these peaks were tentatively assigned to the following redox reaction:

$$Ti_2CO_x + yLi^+ + ye^- H \leftrightarrow Li_yTi_2CO_x \quad (1)$$

The rationale for this assignment is that drying at 200° C., prior to assembling the coin cells, rids MXene of water or any OH species and leads to an oxygen terminated surface. In other words, the assumption is made that the $Ti_2CO_x$ surface is similar to that of titania. Like in the case of the titanates, even if the potentials vs. Li are relatively high, it is an advantage from a safety stand point. Ex situ XRD results (not shown) after lithiation produced no new peaks, but a downshift of the MXene peaks was observed, with an increase of the c parameter by 19.5% which indicates intercalation of Li between the MXene layers, and not a conversion reaction.

Figure 31B:
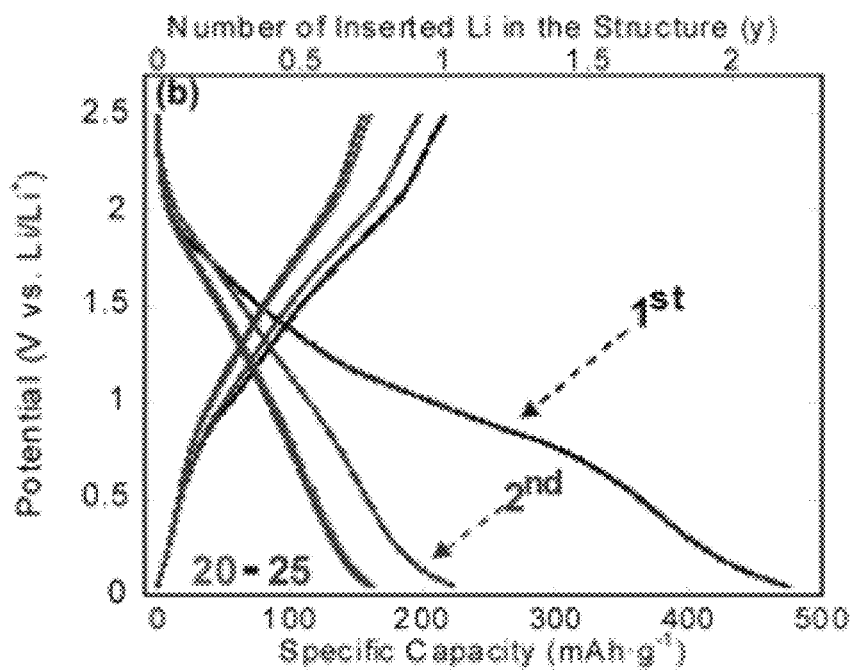
FIG. 31(B) provides the galvanostatic charge/discharge curves at a C/10 rate.

FIG. 31(b) shows the galvanostatic charge/discharge curves at a rate of C/10 (1 Li$^+$ per formulae exchanged in 10 h). The capacity loss in the first cycle can again be attributed to a SEI layer formation at potentials below 0.9V vs. Li$^+$/Li, as well as to the irreversible reduction of electrochemically active surface groups such as fluorine or possibly hydroxyls. The specific capacity stabilized after five cycles at ≈160 mAh·g$^{-1}$. This value corresponds to y≈0.75 in reaction 1.

At 160 mAh·g$^{-1}$, the capacity of the treated powders is about 5 times higher than that of the as-received Ti$_2$AlC (ca. 30 mAh·g$^{-1}$ at C/10) powders. This increase in capacity is traceable to the higher surface area, more open structure and weaker bonds between the MX layers after HF treatment. In addition to the morphological changes, the Li insertion sites are also now different (i.e. the site binding energies) which could also explain the differences in capacity.

Figure 31C:
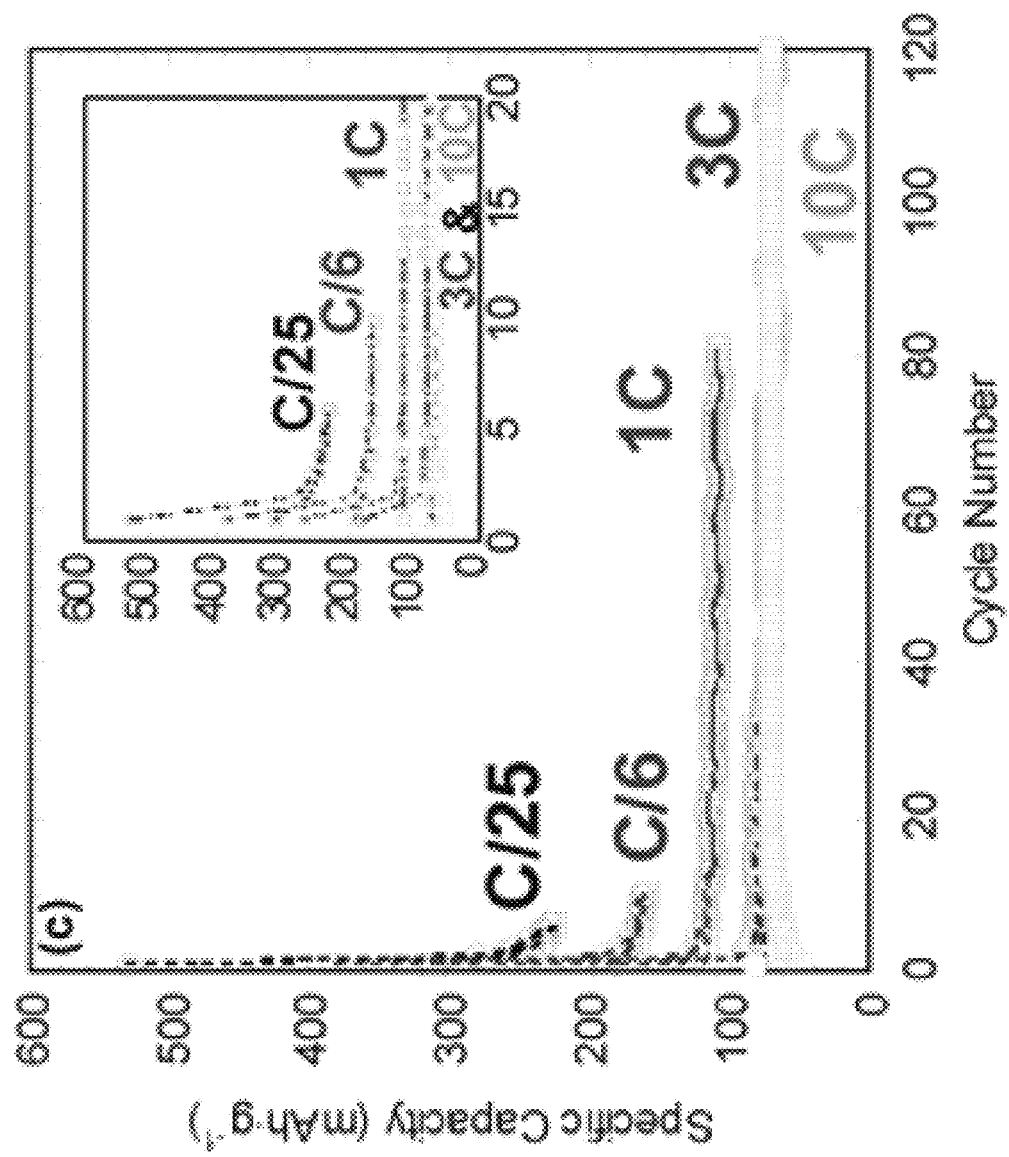
FIG. 31(C) shows specific lithiation (circles in the figure) and delithiation (squares in the figure) capacities (per mass of active material) vs. cycle number at different rates. The inset in FIG. 31(C) is a zoom of the first 20 cycles.

The specific capacities vs. cycle number at different cycling rates (C/25, C/6, 1 C, 3 C, and 10 C) calculated from galvanostatic curves are shown in FIG. 31(c). The highest capacity was obtained at a rate of C/25. The specific capacity values stabilize after 5 cycles, for all scan rates. At a C/25 rate, the capacity is 225 mAh·g$^{-1}$, which corresponds to y≈1. At rates of 1 C and 3 C, the capacities, after 80 cycles, were, respectively, 110 mAh·g$^{-1}$ and 80 mAh·g$^{-1}$. Even at rates of 10 C, a stable capacity of 70 mAh·g$^{-1}$ was obtained for more than 200 cycles. These results clearly demonstrate that it is possible to stably electrochemically intercalate Li$^+$ ions in the interlayer spaces between exfoliated Ti$_2$C sheets, and achieve stability.

The exfoliated Ti$_2$C, produced by HF treatment of Ti$_2$AlC powders, showed reversible capacity about 5 times higher than pristine Ti$_2$AlC, due to its open structure, weaker interlaminar forces, and higher SSA. Electrochemical measurements showed intercalation and deintercalation of Li$^+$ ions at 1.6 V and 2 V vs. Li$^+$/Li, respectively. The exfoliated Ti$_2$C material exhibited a stable capacity of 225 mAh·g$^{-1}$ at a C/25 rate, corresponding to about one Li per Ti$_2$CO$_x$ formula unit. A stable cycling capacity of 80 mAh·g$^{-1}$ was observed after 120 cycles at a 3 C rate, and 70 mAh·g$^{-1}$ was observed after 200 cycles at a 10 C rate.

Example 12

Intercalation of Lithium and Use of Other MXenes in Batteries

Similar experiments with Ti$_3$CN, TiNbC, Nb$_2$C, V$_2$C, and Ta$_4$C$_3$ have also shown that these materials can also be intercalated with Li and used in lithium ion batteries.

To explore the feasibility of using Nb$_2$CT$_s$ and V$_2$CT$_s$ as electrodes in lithium ion batteries (LIBs), cyclic voltammetry (CV) and galvanostatic charge-discharge cycling (GV) were carried out. The CV curves for Nb$_2$CT$_s$ showed no significant lithiation and delithiation capacity at voltages higher than 2.5 V. Hence, the GV for Nb$_2$CT$_s$ was carried out between 0 and 2.5 V against Li/Li$^+$. The voltage profile for Nb$_2$CT$_s$ at 1 C cycling rate yielded a first cycle capacity of ~422 mAh·g$^{-1}$. The second cycle capacity was about 250 mAh·g$^{-1}$. Without intending to be bound by the correctness of any particular theory, the reason for the first cycle irreversibility could be due to solid electrolyte interphase (SEI) formation or due to irreversible reaction of Li with the surface groups and/or water molecules in the as-synthesized MXene. In principle, this irreversibility could be minimized by controlling the surface chemistry of MXene or by prelithiating the electrode material. After 100 cycles, a reversible capacity of 170 mAh·g$^{-1}$ was obtained.

Because the CV for V$_2$CT$_s$ showed a large capacity close to 3 V, this material was tested between 0 and 3 V against Li/Li$^+$. The first cycle capacity was found to be ~380 mAh·g$^{-1}$ and the reversible capacity ~210 mAh·g$^{-1}$. Intriguingly, the V$_2$CT$_s$, produced by etching attrition milled V$_2$AlC, showed >30% enhancement in Li uptake compared to V$_2$CT$_s$ produced from unmilled V$_2$AlC. This might be explained by the decreased particle size, facilitating Li diffusion between the layers. A reversible capacity of 288 mAh·g$^{-1}$ was obtained instead of 210 mAh·g$^{-1}$ at the same cycling rate of 1 C after 50 cycles. A reversible capacity of 260 mAh·g$^{-1}$ was obtained for the V$_2$CT$_s$, produced by etching attrition milled V$_2$AlC, after 150 cycles.

More than ⅔ of the reversible lithiation capacity for Nb$_2$CT$_s$ was below 1 V, while for both Ti$_3$C$_2$ and Ti$_2$C, the capacities below 1 V were about ½ of the reversible capacity. Conversely, in the case of V$_2$CT$_s$, less than ½ of the reversible lithiation capacity is below 1 V and more than ⅔ of the delithiation capacity is at voltages higher than 1.5 V. This is an important finding since it shows that each MXene has its own active voltage window. With the variety of possible MXenes chemistries, selection of an optimum MXene for a required voltage window can in principle be achieved. That is, some MXenes could function better as anodes, while others could, in principle, be used as cathode materials for lithium ion batteriess. Both Nb$_2$CT$_s$ and V$_2$CT$_s$ (produced by HF treatment of attrition milled V$_2$AlC powders at RT for 8 h) were shown to be capable of handling high cycling rates. At 10° C., capacities of 110 mAh·g$^{-1}$ for Nb$_2$CT$_s$ and 125 mAh·g$^{-1}$ for V$_2$CT$_s$ were obtained after 150 cycles. These values were much higher than what was reported for commercial graphite when charged and discharged at 10° C. (graphite loses more than 80% of its theoretical capacity at 10° C.). The high rate capability could be explained by the low Li diffusion barrier in Mxenes. The coulombic efficiency at the reversible capacity was about 99.6% for Nb$_2$CT$_s$ at 10° C. For V$_2$CT$_s$, the coulombic efficiency varied between 98% and 100%. Although the reversible capacity of MXenes at high cycling rates (i.e., 10° C.) was comparable to titania based anodes, the latter have maximum theoretical capacities of the order of 170 mAh·g$^{-1}$ even at slow scan rates, while V$_2$CT$_s$ (produced from milled V$_2$AlC) has a reversible capacity of 260 mAh·g$^{-1}$ at 1° C. The results obtained herein were obtained on just synthesized and not well purified compounds and should thus be considered quite preliminary. The higher rate performances, however, were encouraging and suggest that Nb$_2$CT$_s$ and V$_2$CT$_s$ can be used as promising electrode materials in lithium ion batteries, especially for high power applications. For example, the Li-capacities of additives-free fully delaminated Ti$_3$C$_2$T$_s$ electrodes were roughly 4 times those of nondelaminated Ti$_3$C$_2$T$_s$.

Example 13

Intercalation of Sodium, Potassium, Ammonium, Magnesium, and Aluminum Ions

The examples provided herein for the intercalation of various ions use Ti$_3$C$_2$T$_s$ as a convenient template for investigation. It should be appreciated that the results described herein are expected to be reproducible with other MXene materials, and embodiments include those wherein the intercalation is described more generally with respect to these other MXene materials. That is, other specific embodiments include the other MXene materials described herein intercalated with the ions described herein, and the articles derived from such intercalated materials.

Example 13.1

Materials and Methods $Ti_3C_2T_s$ (where $T_s$ stands for surface termination, such as OH, O or F bonded to Ti atoms) was synthesized by exfoliating the corresponding MAX phases with "A" element etched away. $Ti_3AlC_2$ powder with particle size less than 38 μm was treated with 50% aqueous HF solution (Fisher Scientific, Fair Lawn, N.J.) at room temperature (RT), for 18 h. The resulting suspensions were washed six to seven times using deionized water and separated from remaining HF by centrifuging until the pH of the liquid reached around 5. The wet sediment was moved to a wide-mouth jar by ethanol and dried in air for 3 to 4 days. Then the obtained $Ti_3C_2T_s$ was placed into capped glass vials and stored at ambient conditions for further experiments.

Electrodes were prepared by mechanical processing of the pre-mixed slurry, containing ethanol (190 proof, Decon Laboratories, Inc.), $Ti_3C_2T_s$ powder, polytetrafluoroethylene (PTFE) binder (60 wt. % in $H_2O$, Aldrich) and onion-like carbon (OLC) (28), which was added to create a conductive network in-between the particles (MXene is anisotropic: good in-sheet conductivity, poor conductivity between the sheets). Resulting electrodes which were used for all experiments contained: 85 wt. % of the $Ti_3C_2T_s$, 10 wt. % of OLC, 5 wt. % of PTFE and had thickness of 75-100 μm and mass density per unit area of 7-9 mg/cm2. (1)

To intercalate $Ti_3C_2T_s$, 0.15 g of the powder was suspended in 5 ml of 30 wt. % aqueous solution of potassium hydroxide, potassium acetate, lithium acetate, sodium acetate, sodium formate, sodium citrate, and zinc sulfate; 25, 20 and 10 wt. % aqueous solution of magnesium sulfate, sodium sulfate and potassium sulfate, respectively; 30% aqueous solutions of acetic acid, sulfuric acid, and ammonium hydroxide. Then, the mixtures were stirred for 24 h with a magnetic stirrer at room temperature, RT. Afterwards, the resulting colloidal solutions were filtered through a polyester membrane (25 mm diameter, 3 μm pore size, Osmonics Inc., Minnetonka, Minn., USA) and dried in a desiccator under vacuum (<10 Torr) at RT.

To obtain few-layer $Ti_3C_2T_s$, multilayered $Ti_3C_2T_s$ was stirred with dimethyl sulfoxide (DMSO) for 18 h at room temperature, then the colloidal suspension was centrifuged to separate the intercalated powder from the liquid DMSO. After decantation of the supernatant, deionized water was added to the residue in a weight ratio of MXene to water of 1:500. Then the suspension was sonicated under Ar for 4 h, and centrifuged for 1 h with 3500 rpm. At last, the supernatant was decantated and filtered using a porous MF-millipore mixed cellulose ester membrane filter (47 mm diameter, 0.025 μm pore size, Fisher Scientific, Fair Lawn, N.J., USA) and dried in a desiccator under vacuum (<10 Torr) at RT for 24 h, resulting in MXene paper that detaches easily from the membrane 2 and can be further used as a free-standing electrode. The tickness of the MXene paper varied from 2 to 20 μm. Mass density per unit area of tested electrodes was 2-3 mg/cm2.

The following ionic compounds were used for intercalation into $Ti_3C_2T_s$: potassium hydroxide (≥85.0%, Fisher Chemical, Fair Lawn, N.J., USA), potassium sulfate (certified ACS crystalline, Fisher Scientific, Fair Lawn, N.J., USA), potassium acetate (ACS reagent grade, MP Biomedicals, LLC, Solon, Ohio, USA), lithium acetate anhydrous (≥99%, Acros Organics, Fair Lawn, N.J., USA), sodium acetate anhydrous (≥99.0%, Alfa Aesar, Ward Hill, Mass., USA), sodium formate (>99.0%, Alfa Aesar, Ward Hill, Mass., USA), sodium citrate tribasic dehydrate (>98%, Sigma Aldrich, St. Louis, Mo., USA), sodium sulfate anhydrous (99.7%, Acros Organics, Fair Lawn, N.J., USA), magnesium sulfate (≥99.5%, Alfa Aesar, Ward Hill, Mass., USA), zinc sulfate heptahydrate (≥99.0%, Sigma Aldrich, St. Louis, Mo., USA). Ammonium hydroxide (28-30 wt. % in water, Fisher Scientific, Fair Lawn, N.J., USA), acetic acid (99.8%, Acros Organics, Fair Lawn, N.J., USA), and sulfuric acid (50%, Ricca Chemical Company, Arlington, Tex., USA) were also used as intercalants.

The following salts were used as electrolytes in electrochemical experiments: potassium hydroxide (≥85.0%, Fisher Chemical, Fair Lawn, N.J., USA), potassium sulfate (certified ACS crystalline, Fisher Scientific, Fair Lawn, N.J., USA), sodium acetate anhydrous (≥99.0%, Alfa Aesar, Ward Hill, Mass., USA), sodium hydroxide (≥98%, Alfa Aesar, Shore Road, Heysham, Lancs UK), sodium nitrate (≥99%, Sigma Aldrich, St. Louis, Mo., USA), magnesium nitrate hexahydrate (≥99%, Sigma Aldrich, St. Louis, Mo., USA), magnesium sulfate (≥99.5%, Alfa Aesar, Ward Hill, Mass., USA), aluminum sulfate hydrate (≥98.0%, Fluka, St. Louis, Mo., USA), ammonium sulfate (≥99.0%, Sigma Aldrich, St. Louis, Mo., USA), and lithium sulfate (≥98.5%, Sigma Aldrich, St. Louis, Mo., USA).

Activated carbon film electrodes were prepared following the same procedure as for the $Ti_3C_2T_s$ electrodes, but without any conductive additive. Resulting AC electrodes composition was 95 wt. % of YP-50 activated carbon (Kuraray, Japan) and 5 wt. % of the PTFE. They had thickness of 100-150 μm and mass density per unit area of 10-25 mg/cm$^2$.

All electrochemical measurements were performed in 3-electrode Swagelok cells, where MXene served as working electrode, over-capacitive activated carbon films were used as counter electrode and Ag/AgCl in 1 M KCl as a reference in order to precisely control electrochemical potentials.

Cyclic voltammetry, electrochemical impedance spectroscopy and galvanostatic cycling were performed using a VMP3 potentiostat (Biologic, France).

Cyclic voltammetry was performed using scan rates from 1 mV/s to 1000 mV/s. Diapasons of cycling were chosen using the following principles:

1) As starting potential, open circuit potential right after assembly of the cell was chosen.

2) Minimum potential was chosen by subsequent CV series with increasing lower limit, with the end at the lower limit minimum potential, at which no electrolyte decomposition was observed.

Figure 37:
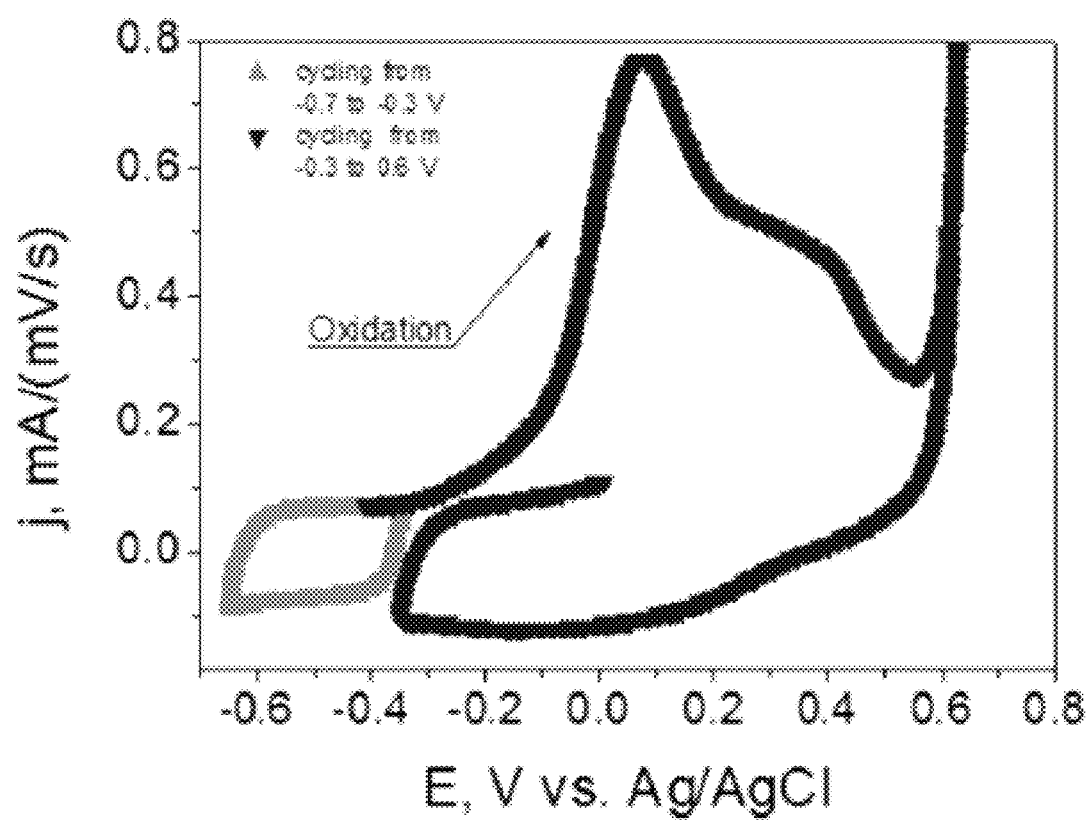
FIG. 37 shows cyclic voltammetry sweeps of the $Ti_3C_2T_s$ in different potential windows (can rate 10 mV/s) in 1 M KOH.

The reason for choosing OCP as upper limit is to avoid oxidation of the material in aqueous electrolytes which would lead to higher resistance and lower resulting capacitance (see FIG. 37).

Electrochemical impedance spectroscopy (EIS) was performed at open circuit potential with a 10 mV amplitude between 10 mHz and 200 kHz.

Galvanostatic cycling was performed at 0.1 and 1 A/g with potential limits selected specifically for each electrolyte: from −0.5 to 1 V vs. Ag/AgCl for 1 M KCl, from 0 to −0.7 V vs. Ag/AgCl for 1 M $MgSO_4$ and 1 M NaOAc.

X-Ray diffraction patterns were recorded with a powder diffractometer (Rigaku SmartLab) using Cu Kα radiation (λ=1.54 Å) with 0.01° 2θ steps and 6 s dwelling time. Scanning electron microscopy (SEM) and energy dispersive X-ray spectroscopy (EDX) analysis were performed on Zeiss Supra 50 VP (Carl Zeiss SMT AG, Oberkochen, Germany).

XRD patterns of the $Ti_3C_2T_s$ electrodes were collected on a Brucker D8 diffractometer using a Cu Kα radiation (λ=1.5406 Å) in the range 2θ=5–20° with a step of 0.02°. The sample was placed in a 2-electrode Swagelok-type cell and covered with a Mylar window to avoid electrolyte evaporation, allowing in-situ XRD recording (cell from LRCS, Amiens University). A MXene film, a mixture of 90% $Ti_3C_2T_s$, 5% PTFE and 5% carbon black served as the working electrode, and was pressed on a nickel foam current collector and dried at 120° C. Over-capacitive activated carbon films were used as counter electrode. Cyclic voltammetry advanced technique was used in order to control the cell potential. The scans were recorded each 0.2 V after linear sweep at 1 mV/s.

Theoretical specific surface area calculations for $Ti_3C_2(OH)_2$ and estimation of the number of layers in multilayer exfoliated $Ti_3C_2T_s$ and few-layer $Ti_3C_2T_s$:

Area of one lattice=Lattice parameters a×b×sin) (60°=3.0581 Å×3.0588 Å×$(3)^{0.5}/2 \times 10^{-20}$=8.1E-20 m².

Each layer in the cell has 3 Ti, 2 C, 2 O, and 2 H. Then the weight of the layer in the cell=[201.64 g/mole]/[6.023E$^{23}$ atoms/mole]=3.3478E-22 g. The SSA=8.1×10$^{-20}$/3.3478×10$^{-22}$=241.97 m²/g (one side). Then the SSA of a Single layer (2 sides) of $Ti_3C_2(OH)_2$ will be 483.94 m²/g.

These Calculations Ignore the Presence of Edges and Defects.

Experimental SSA for MXene paper and its corresponding number of layers:

98 m²/g using $N_2$ yielded ca. 5 layers 128 m²/g using $CO_2$ yielded ca. 4 layers 167 m²/g using Ar yielded ca. 3 layer For stacked $Ti_3C_2T_s$, experimental SSA calculated from nitrogen sorption, is 23 m²/g, which translated to ca. 21 layers in an average MXene lamella.

Calculations of volumetric power and energy densities of electrode and cell:

$C=(\int jdV)/s/V[F/cm^3]$ $E=0.5\ C*V^2/3600[Wh/cm^3]$ $P=E*s/V*3600[W/cm^3]$ where C-normalized capacitance [F/cm³], j-current density [A/cm³], s-scan rate [V/s], voltage window [V], similarly calculations of the gravimetric properties was performed, but gravimetric capacitance and current density were used instead.

Example 13.2

Figure 32:
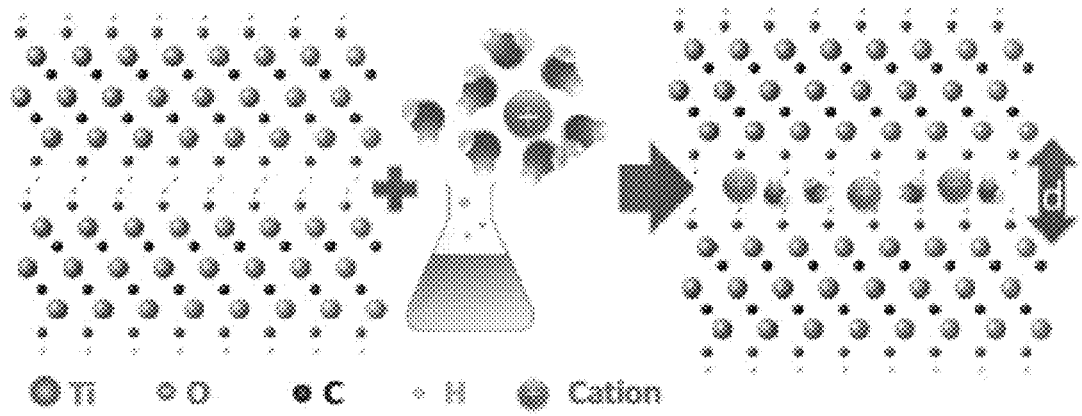
FIG. 32 shows a schematic illustration of the intercalation of cations between $Ti_3C_2T_s$ layers. The interlayer spacing d increases after ion intercalation.

A large number of salts, bases, and acids were explored under conditions described in the Schematic of FIG. 32. See also Table 2.

TABLE 2

Changes in c-lattice parameters acter intercalation of $Ti_3C_2T_s$ with ions. Value of Δ (third column) indicates the increase in c-lattice parameter of $Ti_3C_2T_s$ after intercalation (second column) compared to initial c value of 20.3 Å

| Intercalatant | c, Å | Δ, |
|---|---|---|
| Intercalatants which possess a basic character when dissolved in water | | |
| Potassium hydroxide | 25.4 | 5.1 |
| Ammonium hydroxide | 25.3 | 5.0 |
| Sodium carbonate | 25.3 | 4.8 |
| Sodium hydroxide | 25.1 | 4.6 |
| Sodium formate | 24.9 | 4.6 |
| Sodium citrate | 24.9 | 4.5 |
| Sodium acetate | 24.8 | 4.3 |
| Potassium acetate | 24.6 | 4.2 |
| Lithium acetate | 24.5 | |
| Interalatants which possess a nearly neutral character when dissolved in water | | |
| Zinc sulfate | 21.7 | 1.4 |
| Potassium sulfate | 21.4 | 1.1 |
| Magnesium sulfate | 21.3 | 1.0 |
| Sodium sulfate | 21.0 | 0.7 |

Figure 33A:
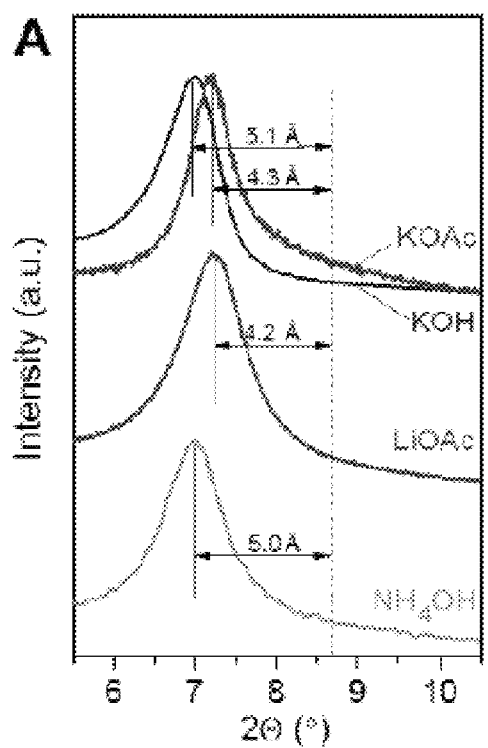
FIG. 33A-C shows X-ray diffractions patterns of various salts.

X-ray diffraction (XRD) patterns showed that, after placing the $Ti_3C_2T_s$ in various salt solutions (FIG. 33, A to C), there was a downshift in the (0002) peak position. This downshift shows that in all cases, there was an increase in the c-lattice parameter. For example, the c value of $Ti_3C_2T_s$ increased from 20.3 Å to as much as 25.4 Å when placed in potassium hydroxide (KOH) and ammonium hydroxide ($NH_4OH$) solutions (FIG. 33A). In addition to the compounds listed in FIG. 33, A to C, other salts intercalated spontaneously when the MXene powders were immersed in sodium carbonate ($Na_2CO_3$), sodium hydroxide (NaOH), or lithium hydroxide (LiOH) solutions.

Figure 33B:
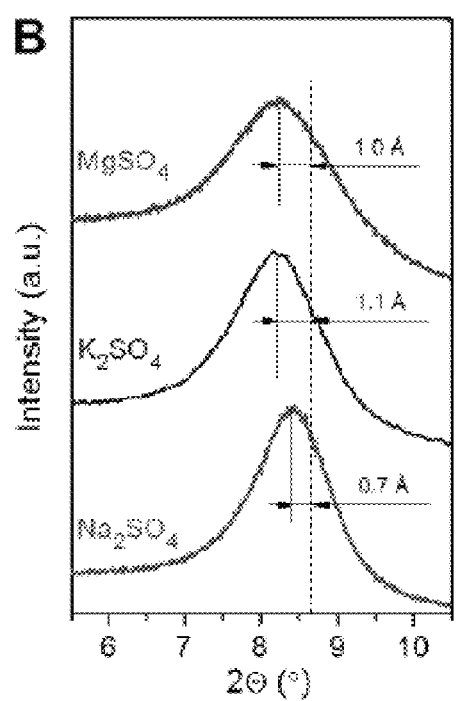
Figure 33C:
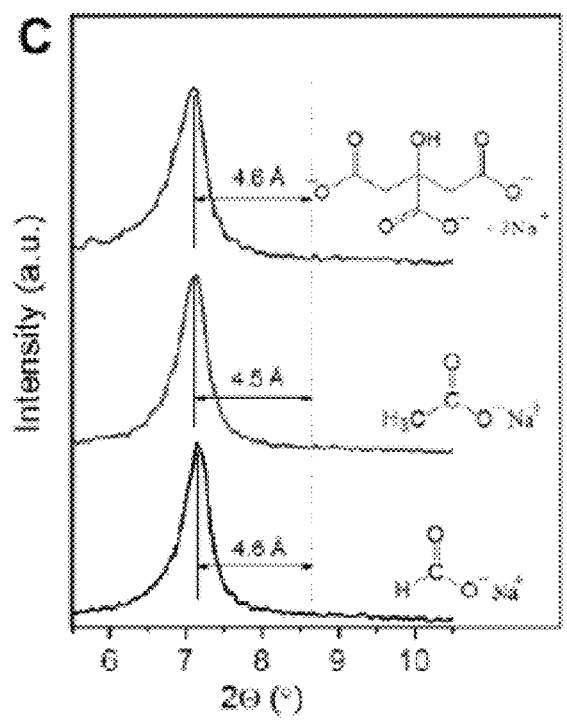

Not all salts behaved similarly. In the case of high-pH solutions such as KOH, $NH_4OH$, NaOH, LiOH, and several others (Table 2), the changes in the interplanar spacing were large (FIG. 33A). Conversely, close-to-neutral solutions such as sodium, potasium, and magnesium sulfates resulted in smaller changes in c (FIG. 33B; see also Table 2). No shift in the (0002) peak positions was observed when $Ti_3C_2T_s$ was immersed in acetic or sulfuric acid.

To shed light on whether the cations or anions intercalated the $Ti_3C_2T_s$ layers, three sodium salts with differing anion radii were tested. The results (FIG. 33C) showed that the c-axis expansions were comparable and independent of anion radii. Furthermore, energy-dispersive x-ray spectroscopy analysis of $Ti_3C_2T_s$ after treatment in the different sulfate salts (FIG. 33B) confirmed the presence of the cations; sulfur was not detected (Table 3), confirming that it is the cations that intercalate between the $Ti_3C_2T_s$ layers.

TABLE 3

Energy-dispersive X-ray spectroscopy analysis of $Ti_3C_2T_x$ powder before and after intercalculation.

| | Atomic % | | | | | |
|---|---|---|---|---|---|---|
| Material | Ti | C | O | F | Cation of electrolyte | S |
| $Ti_3C_2T_x$ | 30.0 | 14.8 | 16.0 | 18.9 | — | — |
| $Ti_3C_2T_x$ + KOH | 30.0 | 21.2 | 30.9 | 11.4 | 3.2 | — |
| $Ti_3C_2T_x$ + NaOAc | 30.0 | 16.2 | 18.2 | 27.4 | 5.5 | — |
| $Ti_3C_2T_x$ + $K_2SO_4$ | 30.0 | 17.8 | 8.4 | 15.4 | 1.4 | 0.0 |
| $Ti_3C_2T_x$ + $Na_2SO_4$ | 30.0 | 17.5 | 12.9 | 15.8 | 1.0 | 0.0 |

TABLE 3-continued

Energy-dispersive X-ray spectroscopy analysis of $Ti_3C_2T_x$ powder before and after intercalculation.

| Material | Atomic % | | | | | |
|---|---|---|---|---|---|---|
| | Ti | C | O | F | Cation of electrolyte | S |
| $Ti_3C_2T_x$ + $MgSO_4$ | 30.0 | 29.7 | 17.0 | 18.5 | 0.5 | 0.1 |
| $Ti_3C_2T_x$ + $MgSO_4$ (electrode) | 30.0 | 59.2* | 33.5* | 40.0* | 2.0 | 0.0 |

*Values of the carbon, oxygen and fluorine content are approximate, since spectra were collected from the rolled $Ti_3C_2T_x$ electrode, which contained carbon additive (contributes to C and O content) and PTFE binder (contributes to C, O and F content)

Figure 34:
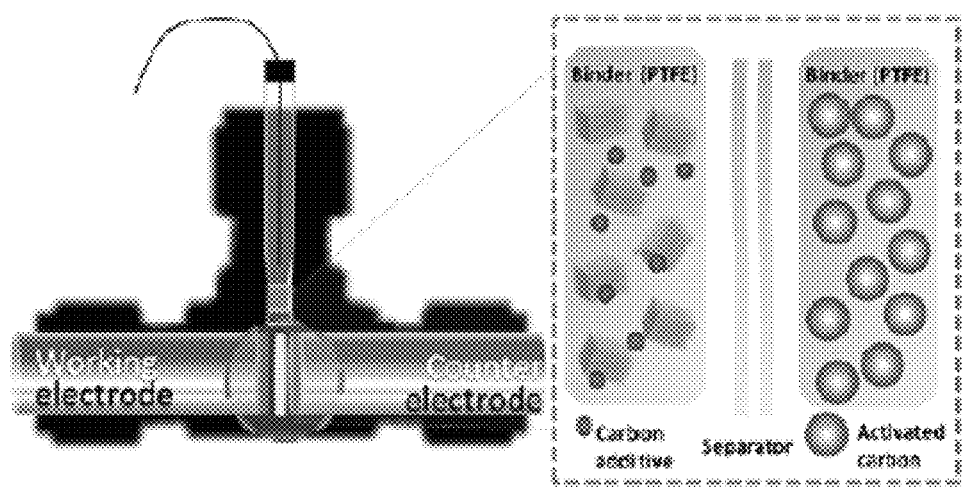
FIG. 34 shows a schematic of the electrochemical testing set-up described in Example 13.2: 3-electrode Swagelok cell, with multilayer $Ti_3C_2T_s$ as working electrode (cubic elements).
Figure 35A:
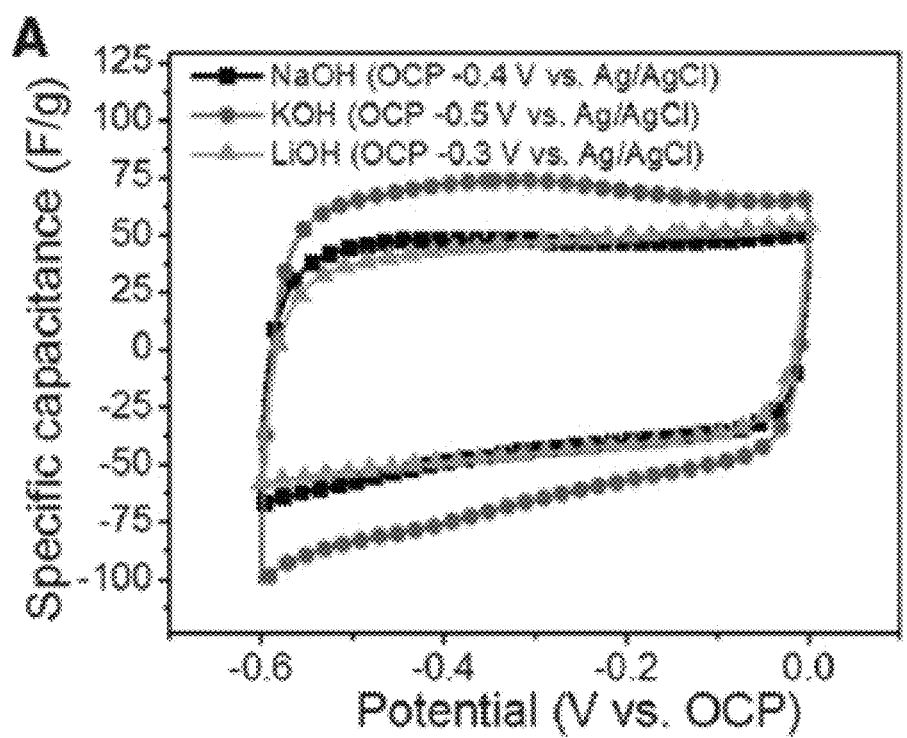
FIGS. 35A-C show electrochemical performance of $Ti_3C_2T_s$-based supercapacitors in various aqueous electrolytes.

Materials with large specific surface area are typically needed to obtain large capacitances in carbon materials for EDLCs. However, at 23 m²/g, the surface area of multilayer exfoliated $Ti_3C_2T_s$ was low. It follows that if double-layer capacitance were the only operative mechanism, one would have expected the capacitance for this material to be less than that of (for example) activated graphene by a factor of 100. However, as noted above, intercalation capacitance can by far exceed double-layer capacitances calculated solely on the basis of a material's surface area. To test this idea, fabricated multilayer $Ti_3C_2T_s$ electrodes were made and tested in NaOH-, KOH- and LiOH-containing electrolytes using a standard three-electrode asymmetrical setup with an Ag/AgCl reference electrode (FIG. 34). The resulting cyclic voltammograms (CVs) are shown in FIG. 35 [see FIG. 36 for the corresponding electrochemical impedance spectroscopy (EIS) results]. The rectangular-shaped CVs indicate capacitive behavior in these basic solutions. Note that in all experiments, the open circuit potential (OCP) was taken as the starting potential for the CV scans because 0.1 V above this potential, $Ti_3C_2T_s$ oxidation is observed in aqueous electrolytes (see FIG. 37).

Figure 35B:
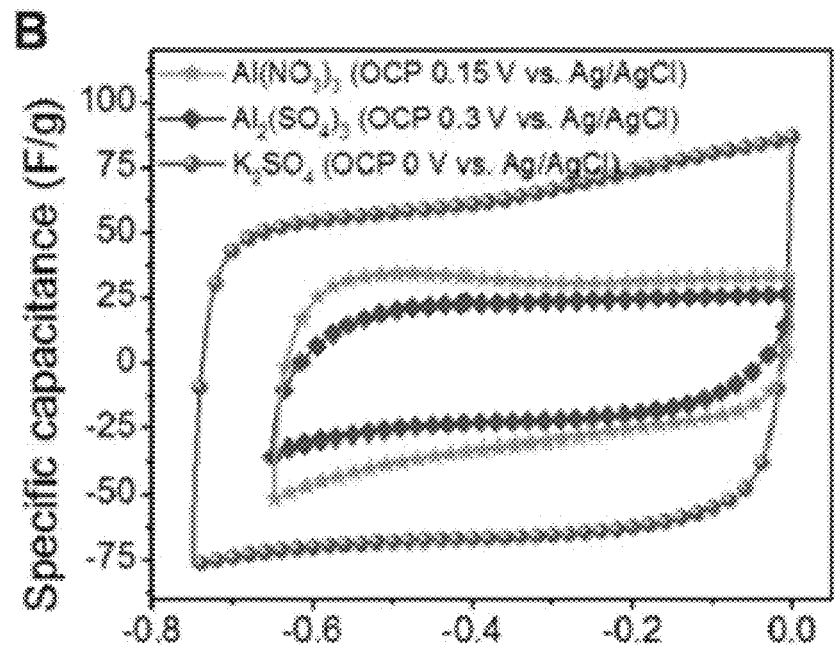
Figure 36A:
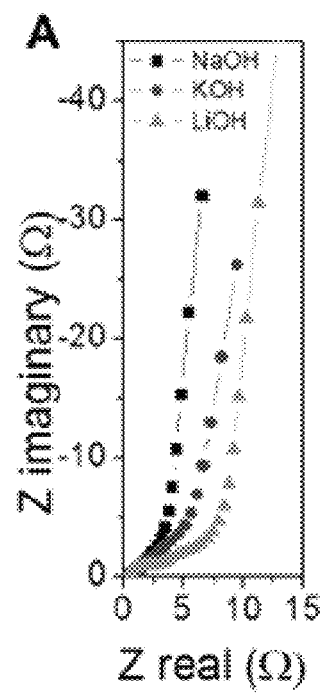
FIGS. 36A-B show Nyquist plot of the $Ti_3C_2T_s$ electrodes in NaOH, KOH, LiOH (FIG. 36A) and $K_2SO_4$, $Al_2(SO_4)_3$, and $Al(NO_3)_3$ solutions (FIG. 36B).
Figure 36B:
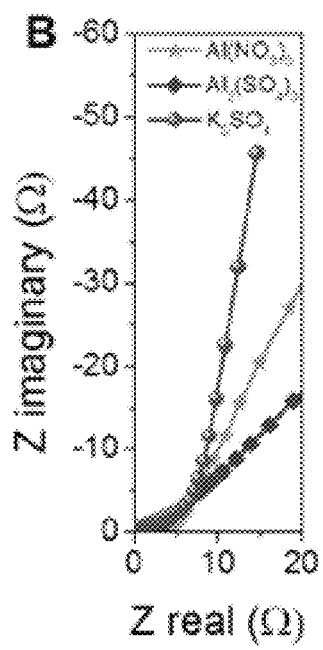

To study the effect of a cation's valence on the electrochemical performance of multilayer exfoliated $Ti_3C_2T_s$ electrodes, CV scans were taken in 1M solutions of potassium and aluminum sulfates and nitrates (FIG. 35B and FIG. 36B). Clearly, the responses in the $K^+$- and $Al^{3+}$-containing solutions were distinctively different, confirming once again that the cations (and not the anions) are intercalating. The CV plots for $K_2SO_4$ were almost perfectly rectangular. Conversely, the CV data for the more acidic (see Table 4) and less conductive $Al_2(SO_4)_3$ electrolyte yielded capacitance values that were significantly lower, and the shape of the CV at 10 mV/s and the EIS results showed a higher resistance (FIG. 35B and FIG. 36B). To ensure that lower electrolyte conductivity did not limit the capacitive performance, $Ti_3C_2T_s$ was tested in 1 M $Al(NO_3)_3$, which had a conductivity similar to that of 1 M $K_2SO_4$ (Table 4). Although the normalized capacitance did not increase appreciably, the CV loops were definitely more rectangular (FIG. 35B), demonstrating the role of electrolyte conductivity.

TABLE 4

Electric conductivity of the aqueous electrolytes used in electrochemical experiments

| Electrolyte | Conductivity, mS/cm |
|---|---|
| 1M NaOH | 141 |
| 1M KOH | 191 |
| 0.5M LiOH | 90 |
| 0.5M $K_2SO_4$ | 100 |
| 1M $(NH_4)_2SO_4$ | 114 |
| 1M $Mg(NO_3)_2$ | 115 |
| 1M $MgSO_4$ | 51 |
| 1M $Al_2(SO_4)_3$ | 30 |
| 1M $Al(NO_3)_3$ | 110 |
| 3M NaOAc | 79 |

Figure 38:
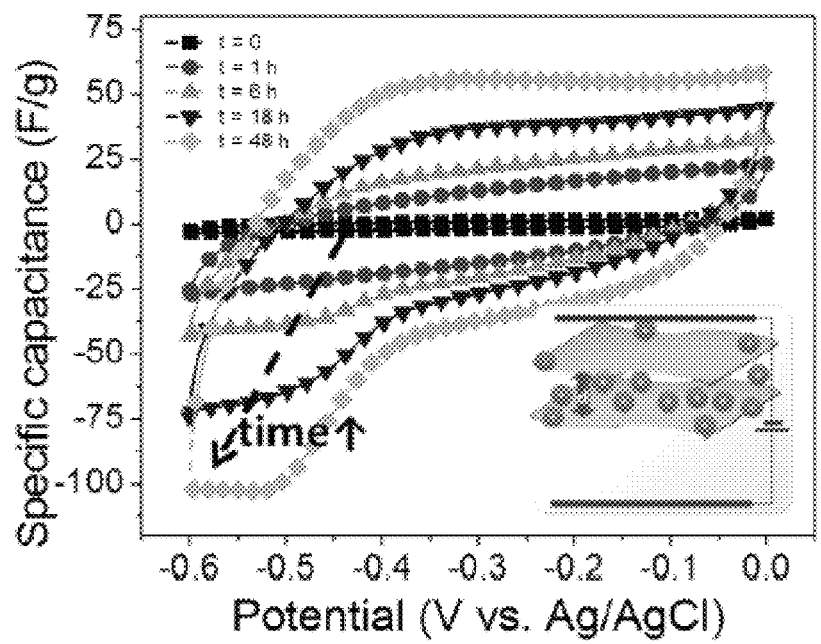
FIG. 38 shows cyclic voltammograms of $Ti_3C_2T_s$ in 1 M MgSO4 electrolyte collected after 0 h, 1 h, 6 h, 18 h, and 48 h of testing. Inset is a schematic illustration of the electrochemically induced cationintercalation between the layers of MXene
Figure 39A:
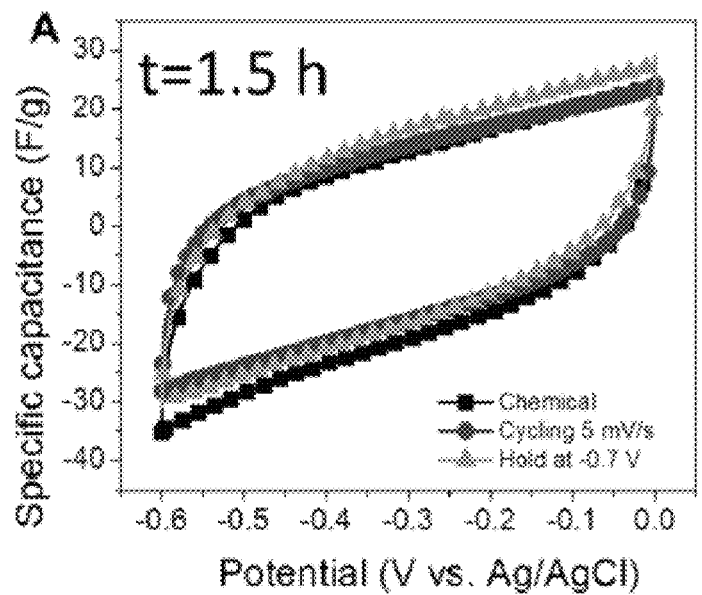
FIGS. 39A-B show cyclic voltammograms of $Ti_3C_2T_s$ in 1 M $MgSO_4$ electrolyte collected duting different cycling regimes: (1) chemical intercalation, screening cycling in-between; (2) continuous cycling at 5 mVs; holding at −0.7 V, screening cycling in-between; collected after 1.5 hours (FIG. 39A) and 7.5 hours (FIG. 39B) from the beginning of the experiment.
Figure 39B:
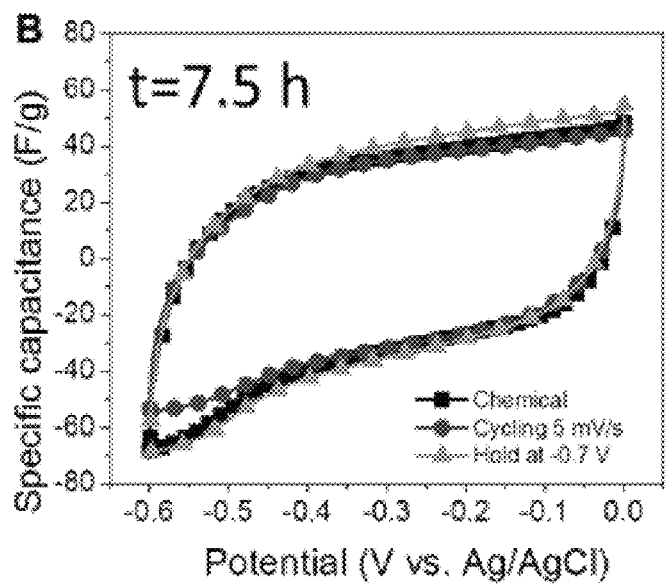

Further evidence for cation intercalation and its beneficial effect on capacitance comes from the observation that for some electrolytes, time was needed to reach a steady state or maximum capacitance. For strongly basic electrolytes (Table 3), such as KOH solutions, the rectangular CV plots were observed almost immediately and the capacitances did not change with time or cycle number. For other electrolytes, however, there was a slow and gradual increase in capacitance with time. For example, for salts such as $MgSO_4$, the CV area increased steadily with time and the maximum capacity was reached only after 48 hours (see FIG. 38 and FIG. 39). Unlike what is observed for graphite, there was no irreversible capacitance loss during the first cycle for any of the electrolytes studied.

Figure 35C:
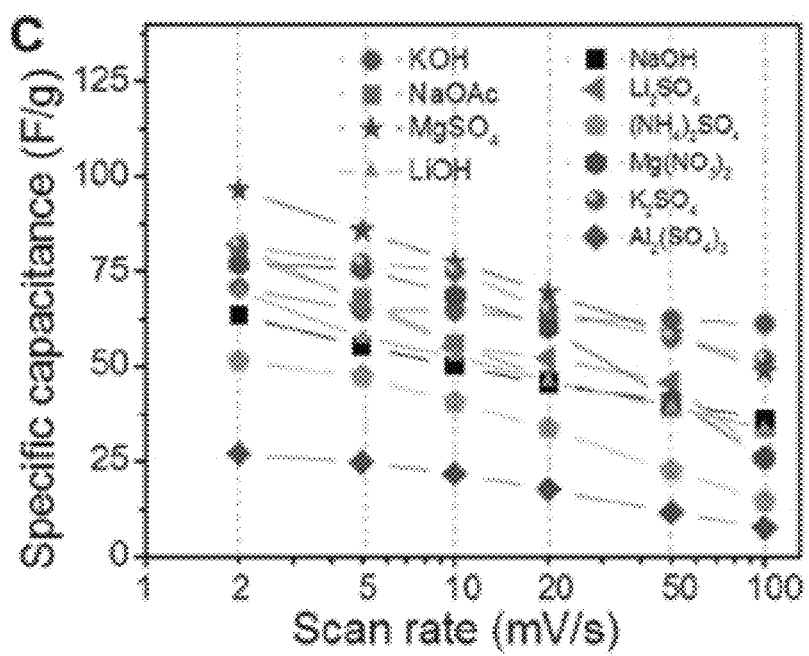

The performance of the multilayer $Ti_3C_2T_s$ in all tested electrolytes is summarized in FIG. 35C. The specific capacitances were calculated by integrating the discharge portions of the CV plots. The results clearly showed responses that depended on the electrolytes used. Moreover, the calculated capacitances were quite high for a material with such low surface area.

Figure 40A:
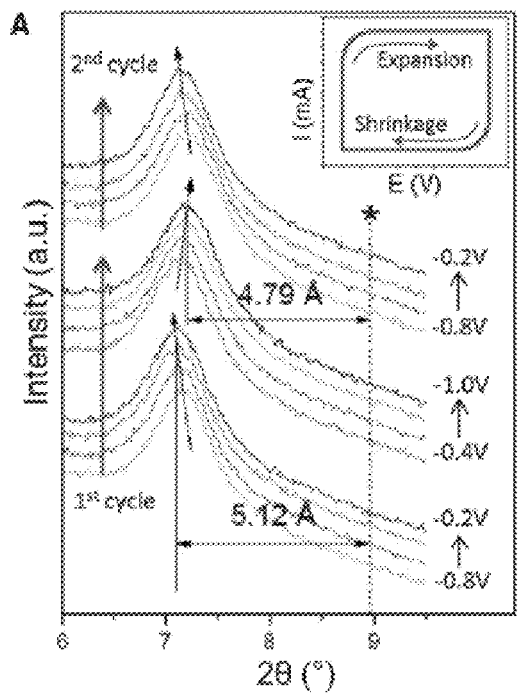
FIG. 40A-B shows results of electrochemical in situ x-ray diffraction study of multilayer exfoliated $Ti_3C_2T_s$.
Figure 40B:
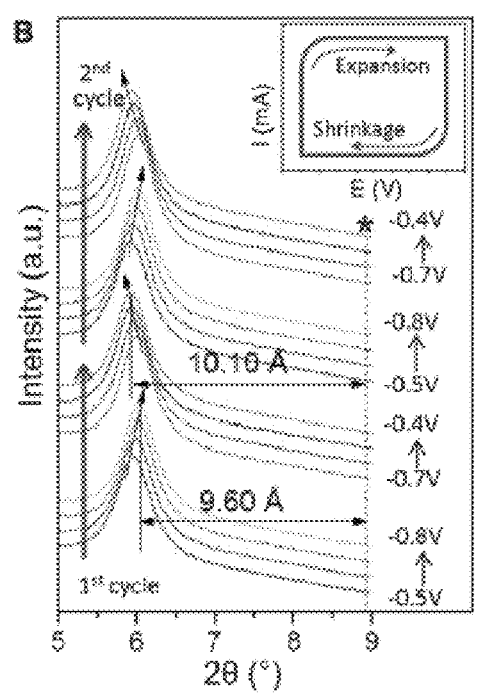
Figure 41:
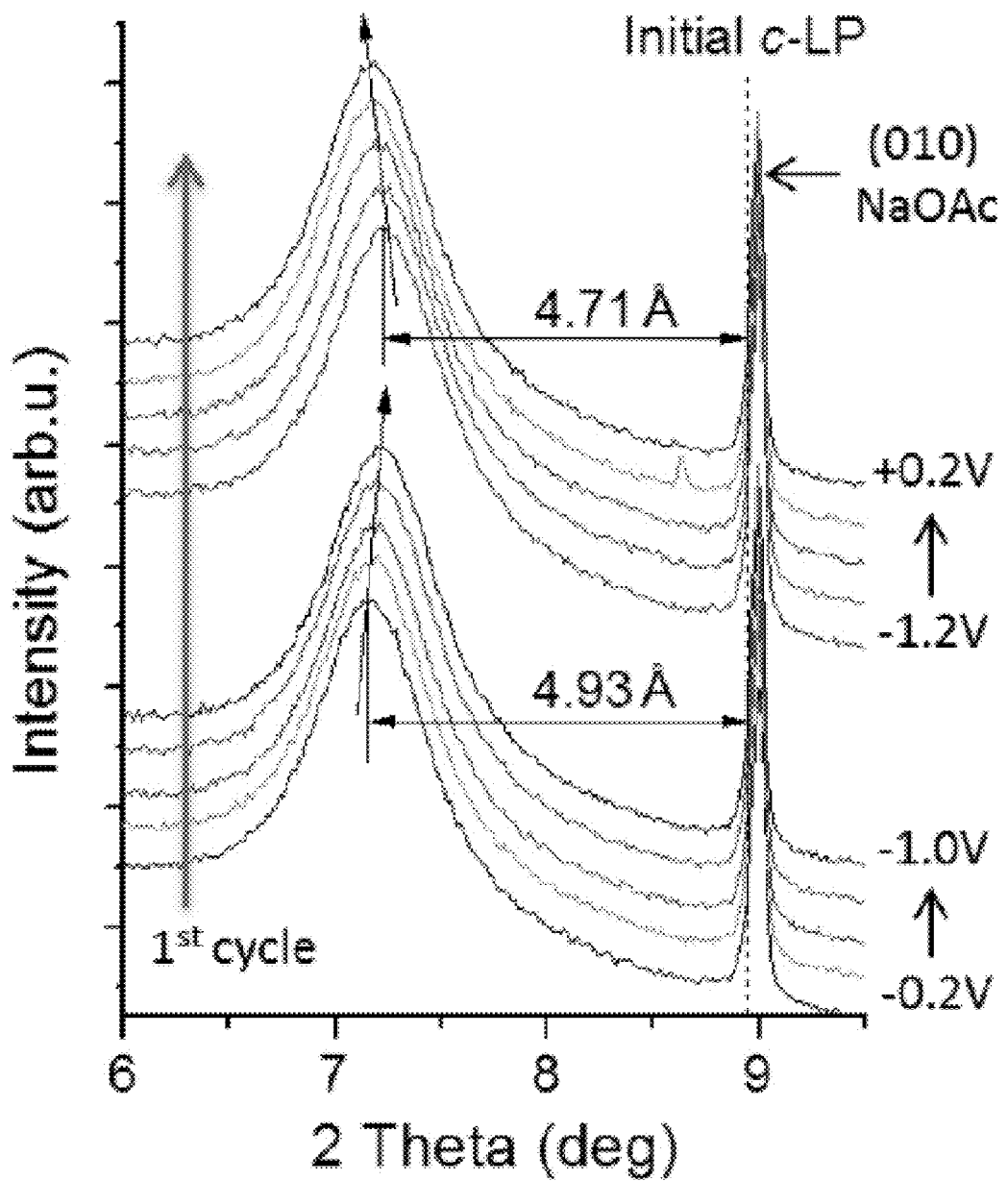
FIG. 41 shows results of electrochemical in-situ X-ray diffraction study of $Ti_3C_2T_s$ in 3 M sodium acetate. Arrows indicate the direction of the (0002) peak shift. See Example 13.2.

In situ XRD studies of the intercalation process during cycling showed that electrochemical cycling led to insignificant changes in the c values. For example, when a $Ti_3C_2T_s$ electrode was cycled in a KOH-containing electrolyte, the c values fluctuated within 0.33 Å as the potential was scanned from −1 to −0.2 V (FIG. 40A). Interestingly, a slight shrinkage in c values was observed with increasing voltage. Similar behavior was observed when $Ti_3C_2T_s$ was cycled in NaOAc-containing electrolyte (FIG. 41). Without being bound by the correctness of any particular theory, one explanation for this observation was that the positively charged ions incorporated in $Ti_3C_2T_s$ increased the electrostatic attraction between layers, in a manner analogous to what was observed for $MnO_2$ in other systems. When $Ti_3C_2T_s$ was electrochemically cycled in a $MgSO_4$-containing solution, the shift of the (0002) peak almost doubled relative to the KOH and NaOAc electrolytes (compare FIG. 40A and FIG. 40B). Here again, a slight shrinkage in c values was observed with increasing voltage.

To gain further insight into the capacitances and what influences them, MXene "paper" produced by filtering delaminated $Ti_3C_2T_s$ was tested. This paper, with a specific surface area of 98 m²/g, was flexible, hydrophilic, additive-free, and conductive. When tested in KOH, the CVs were rectangular, similar to those obtained when multilayer $Ti_3C_2T_s$ powder was used (compare FIG. 42A to FIG. 35A). Furthermore, the EIS results indicated that the $Ti_3C_2T_s$ paper-based capacitors were less resistive (FIG. 42B) than those made with multilayer $Ti_3C_2T_s$ (FIG. 36A). This improved electrochemical response can be related to a number of factors, such as the absence of a binder in the system, good contact between the restacked flakes in the paper, increased accessibility of the structure, and thinner electrodes.

Figure 42D:
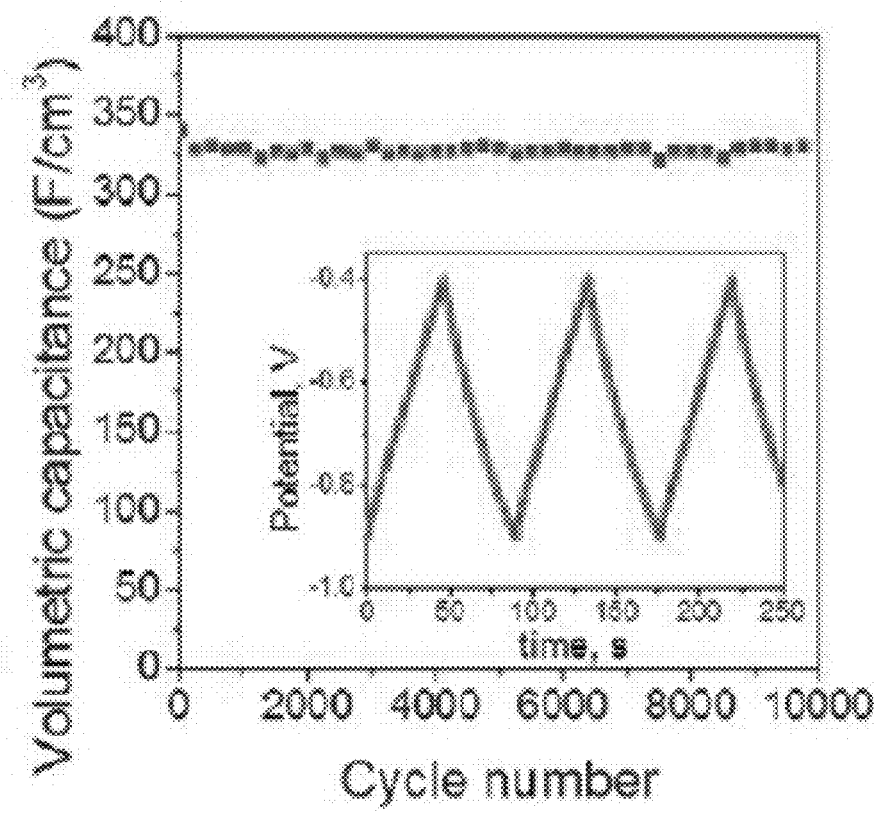
FIG. 42D shows capacitance retention test of $Ti_3C_2T_s$ paper in KOH. Inset: Galvanostatic cycling data collected at 1 A/g.
Figure 43A:
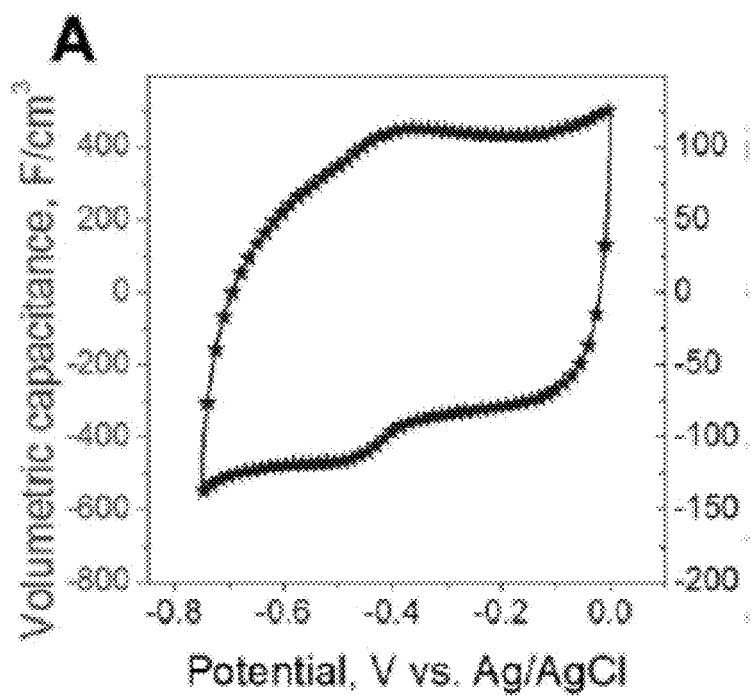
FIGS. 43A-C show data for electrochemistry of $Ti_3C_2T_s$ paper.
Figure 43B:
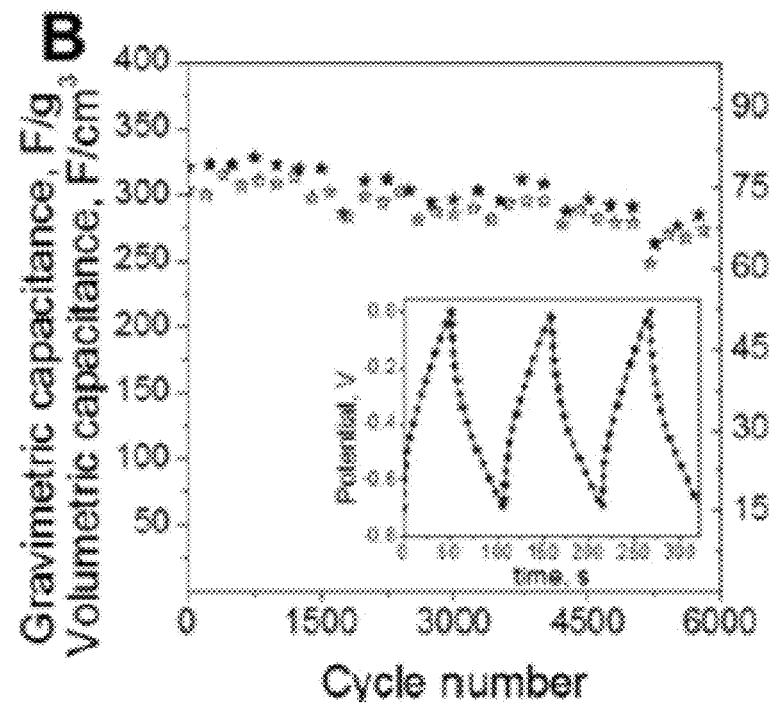
Figure 43C:
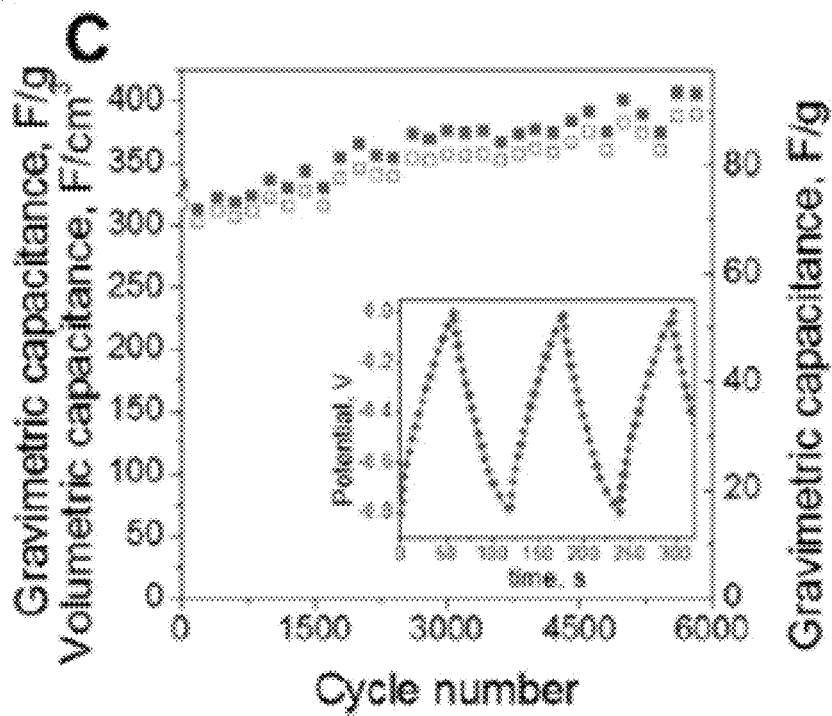
Figure 44A:
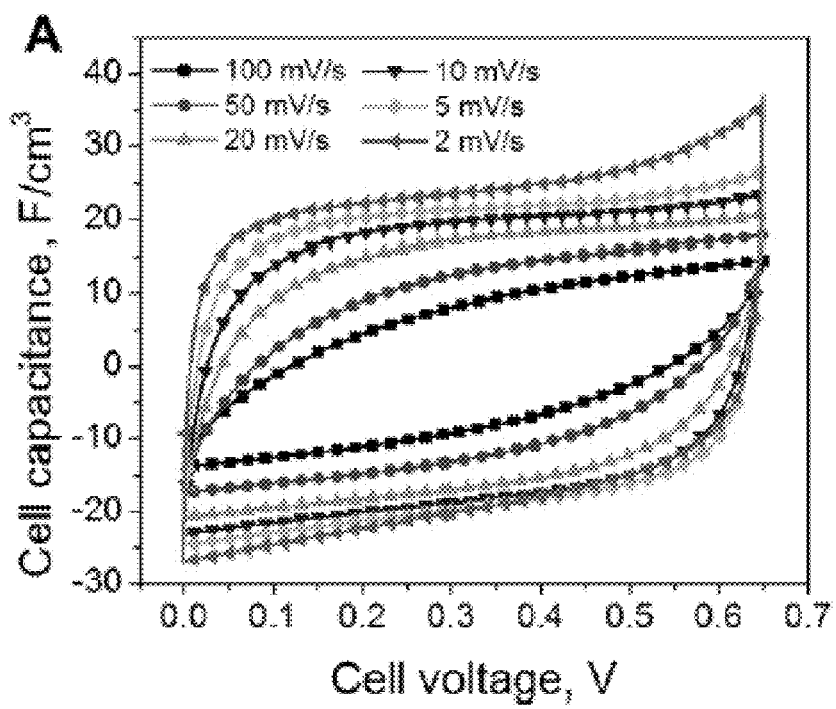
FIG. 44A-B shows $Ti_3C_2T_s$ paper cell performance in $K_2SO_4$.
Figure 44B:
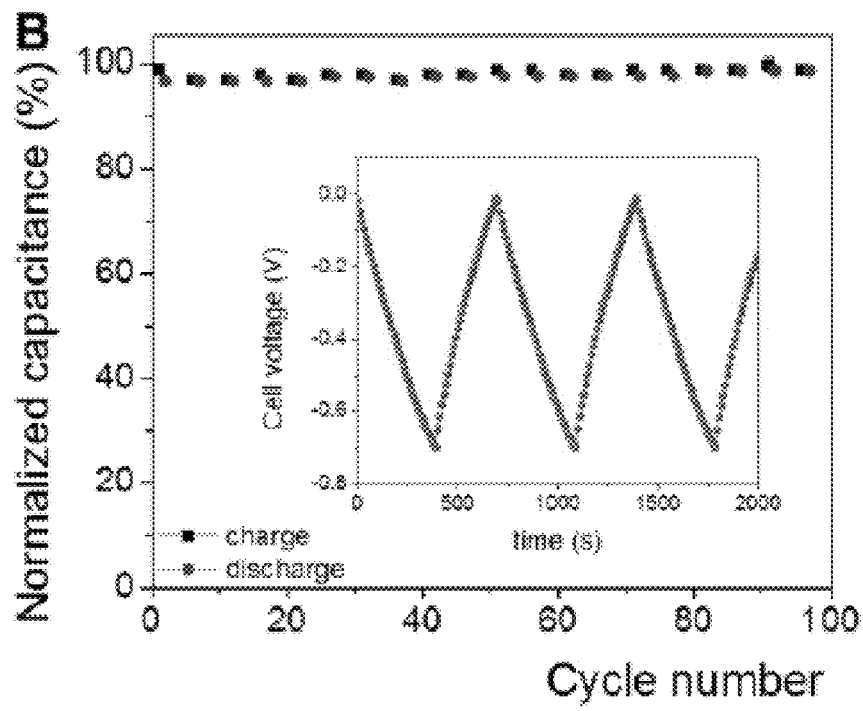

As shown in FIG. 40C, the use of $Ti_3C_2T_s$ paper electrodes instead of multilayer exfoliated $Ti_3C_2T_s$ in some electrolytes (e.g., KOH and NaOAc) roughly doubled the gravimetric capacitance (see FIG. 43 for more information about the performance of $Ti_3C_2T_s$ paper in NaOAc and $MgSO_4$). Further, the volumetric capacitance values recorded for few-layer $Ti_3C_2T_s$ were on the order of 340 F/cm$^3$ for KOH (FIG. 42A and FIG. 44). Those values are much higher than those found for activated graphene[60 to 100 F/cm$^3$] or micrometer-thin carbide-derived carbon electrodes [180 F/cm$^3$]. A capacitance retention test performed by galvanostatic cycling at 1 A/g showed almost no degradation in performance after 10,000 cycles (FIG. 42D).

Example 14

Intercalation of MXene Materials with Kaolinitic Intercalators

The examples provided herein for the intercalation of various ions use $Ti_3C_2T_s$ as a convenient template for investigation. It should be appreciated that the results described herein are expected to be reproducible with other MXene materials, and separate embodiments include those wherein the intercalation is also described with respect to these other MXene materials. That is, other specific embodiments include the other MXene materials described herein intercalated with the materials described herein, and the articles derived from such intercalated materials.

Example 14.1

Methods and Materials

The following chemicals were used in this Example: titanium aluminum carbide 211 ($Ti_2AlC$, >92 wt. % purity, 3-ONE-2, Voorhees, USA), titanium carbide (TiC, 99 wt. % purity, Johnson Matthey Electronic, New York, USA), hydrofluoric acid (HF, 48-51 wt. %, Acros Organics, Morris Plains, USA), hydrazine monohydrate (HM, $N_2H_4 \cdot H_2O$, >98.0 wt. % purity, TCI America, Portland, USA), N,N-dimethylformamide (DMF, ≥99 wt. %, Acros Organics, Morris Plains, USA), dimethylsulfoxide (DMSO, m.w. 78.13, MP Biomedical Inc., Solon, USA), urea (Fisher Scientific, Fair Lawn, USA), acetone (≥99+wt. %, Acros Organics, Morris Plains, USA), ethyl alcohol (Fisher Scientific, Fair Lawn, USA) tetrahydrofuran, THF (≥99+wt. %, Acros Organics, Morris Plains, USA), chloroform (99.8 wt. %, stabilized in 0.5-1% ethanol, Sigma Aldrich, St. Louis, USA), toluene (f.w. 92.14, Fisher Chemical, Fair Lawn, USA), hexane (≥99 wt. %, Reagent Plus, Sigma Aldrich, St. Louis, USA), thiophene (≥99+wt. %, Sigma Aldrich, St. Louis, USA), formaldehyde (37% w/w, Fisher Chemical, Fair Lawn, USA). All chemicals were used as received without further purification.

Characterization.

X-ray diffraction (XRD) patterns were recorded with a powder diffractometer (Siemens D500, Germany) using Cu $K_\alpha$ radiation with a wavelength ~1.54 Å, with 0.02° 2θ steps and 1 sec dwelling time. A scanning electron microscope, (SEM, Zeiss Supra 50VP, Germany) was used to obtain images of the particles. The 2-D sheets were also imaged with a transmission electron microscope, TEM, (JEOL JEM-2100, Japan) using an accelerating voltage of 200 kV. The TEM samples were prepared by suspending the powders in isopropanol, sonicating for 1 min and drying a drop of the mixture on a 200 mesh lacey-carbon-coated copper grid. An XPS (PHI 5000, ULVAC-PHI, Inc., Japan) was used to analyze the surface elemental composition powders before and after intercalation. The resistances of freestanding cold-pressed discs of non-intercalated and intercalated MXenes were measured using a four-probe technique (Cascade Probe Station CPS-1303-24 with 4-point probe head Alessi C4S-57, Cascade Microtech, Inc., Beaverton, USA). A detailed experimental section (materials used and techniques of material preparation) can be found in the Supplementary Information.

Synthesis of $Ti_3AlC_2$.

The $Ti_3AlC_2$ powder was synthesized from a mixture of $Ti_2AlC$ with TiC in a 1:1 molar ratio. The mixture was ball milled for 24 h, heated at 10° C./min to 1350° C. in a tube furnace under Ar flow, and held in these conditions for 2 h. After cooling, the lightly sintered brick was crushed using a mortar and pestle.

Synthesis of MXene. Non-sieved $Ti_3AlC_2$ powder was treated with HF solutions at room temperature (RT), for 22 h. The resulting suspensions were washed five times using deionized water and centrifuged to separate the powder until pH reached ~4. The resulting black powder was divided into two portions. A small part of still wet material was used immediately for intercalation. The rest was dried under vacuum at 100° C. for 22 h, placed into capped glass vials and stored at ambient conditions for further experiments.

Intercalation of MXene.

To intercalate MXene, hydrazine monohydrate (HM) was used. Two types of powders were used: i) as-received, washed, wet MXene and, ii) type (i) powder dried at 100° C. for 22 h. The MXene powders were suspended either in HM or a 1:3 mixture of HM and DMF, and stirred for 24 h with a magnetic stirrer, either at RT or at 80° C.

In all cases, the weight ratio of HM:MXene was 10:1. When the treatment involved only hydrazine monohydrate, the suspensions were filtered and washed with ethanol. In the case of the mixture of HM and DMF, DMF was used for washing instead of ethanol. The powders were then dried in a desiccator under vacuum, created by a water jet pump (the pressure in the desiccator was <10 Torr), at RT for 24 h or in the vacuum (~$10^{-2}$ Torr) oven at 120° C. for 24 h.

Other organic compounds were also tried for intercalation into MXene. Those included DMSO, urea, DMF, acetone, ethyl alcohol, THF, chloroform, toluene, thiophene, and formaldehyde. The procedure to synthesize the MXene intercalation compounds was the same in all cases: i) 9 weighted samples of $Ti_3C_2$, 0.3 g each, were mixed with 5 ml of each organic solvent (excluding urea), then stirred for 24 h at RT; ii) in case of urea, 5 ml of 50 wt. % aqueous solution of urea was added to 0.3 g of $Ti_3C_2$ and stirred for 24 h at 60° C. Afterwards, the resulting colloidal solutions were filtered and dried in a desiccator under vacuum at RT.

De-intercalation of MXene.

To de-intercalate hydrazine/DMF, the reacted powder was carefully weighed, placed in a graphite crucible and outgassed at RT in vacuum (~$10^{-6}$ Torr) for 24 h. While under vacuum, the powder was then heated to 200° C. at 10° C./min, held at this temperature for 72 h and cooled to RT. The powder remained under vacuum for another 48 h before it was retrieved. Between its removal from the furnace and re-weighing, the sample was exposed to ambient air for ~3 min.

Preparation of Pressed MXene Discs.

The non-intercalated and intercalated MXene powders were cold pressed to a load corresponding to a stress of 0.8 GPa using manual hydraulic pellet press (Carver, Model 4350.L, Carver, Inc., Wabash, USA). The resulting discs were 12.5 mm in diameter and in the range of 228-432 μm thick.

Example 14.2

Observations on the Results of Experiments Intercalating Kaolinitic Intercalators Consistent with the apparent layered structure of MXene materials, their intercalation behaviors appear to resemble that of clays. Numerous compounds were studied for clay intercalation, such as formamide and its derivatives, dimethyl sulfoxide (DMSO), urea, alkali metal salts, long-chain alkylamines, and others. Hydrazine monohydrate (HM) or $N_2H_4$—$H_2O$, is probably the most common intercalation agent for clays. It intercalates into the interlayer space between the octahedral aluminum hydroxide and tetrahedral silica sheets, resulting in an expansion of the clay c-lattice parameter, c-LP, along [0001] from 7.2 to 10.3-10.4 Å. As shown below, the intercalation of hydrazine and co-intercalation with DMF between the $Ti_3C_2$ layers also resulted in an increase of the c lattice parameter, in this case from 19.5 Å to 25.48 Å and 26.80 Å, respectively. Partial de-intercalation of hydrazine occurred by heating the intercalated $Ti_3C_2$ at 120° C. in vacuum and de-intercalation of both hydrazine and DMF at 200° C. Comparison of molecular dynamics simulation and experimental results suggested that a nearly complete monolayer of hydrazine is inserted between the $Ti_3C_2$ layers of the host. Intercalation of $Ti_3C_2$ with urea and dimethyl sulfoxide (DMSO), as well as intercalation of $Ti_3CN$ and TiNbC with hydrazine and DMSO demonstrated in this study, suggest a possibility of synthesis of dozens of new intercalation compounds based on carbides and carbonitrides of transition metals.

Figure 45A:
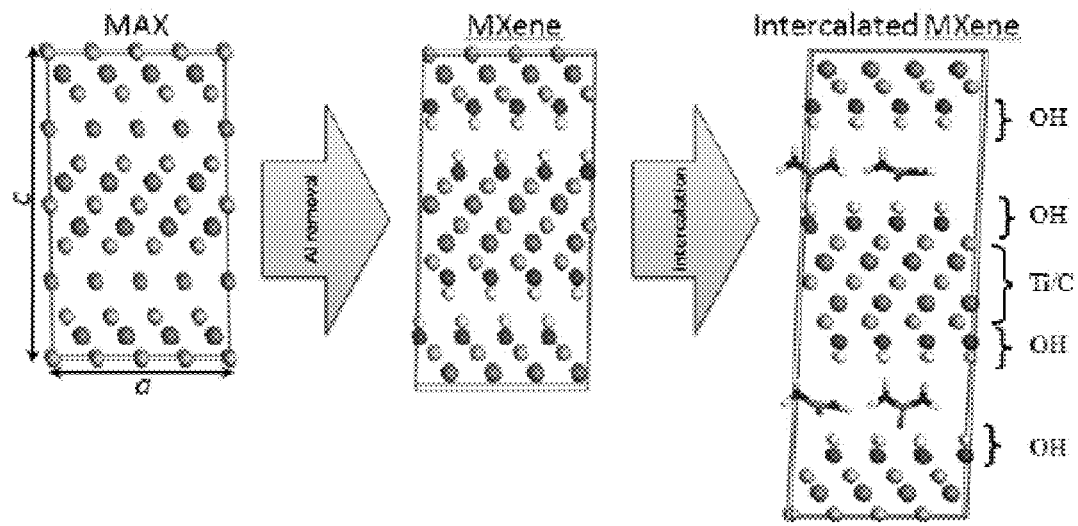
FIG. 45A-C shows evidence of MXene intercalation.
Figure 45B:
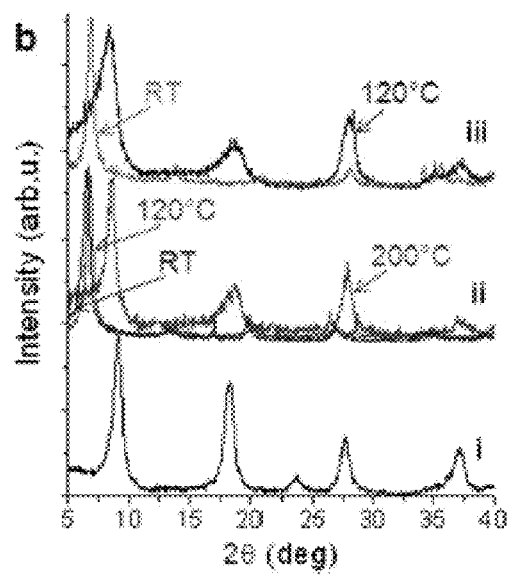
Figure 45C:
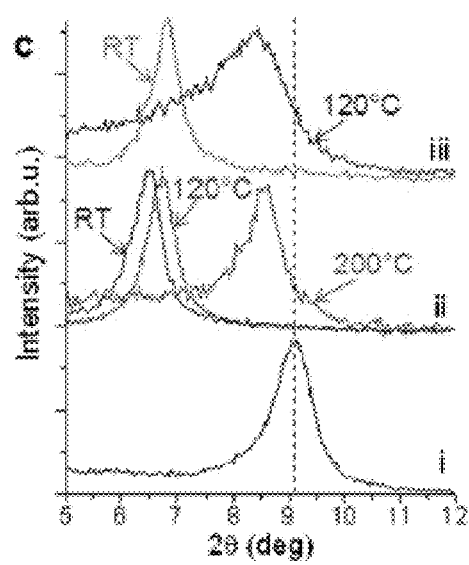
Figure 46:
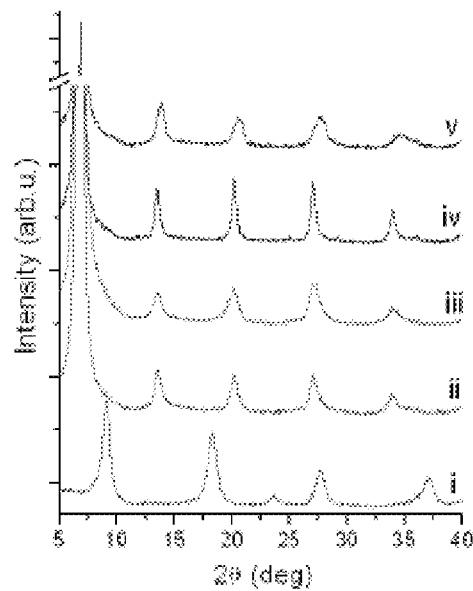
FIG. 46 shows XRD patterns of MXene: (i) before any treatment, (ii) after HM treatment in DMF at 80° C., (iii) after HM treatment at 80° C.; and after HM treatment in DMF at 80° C. (iv) and at relevant temperature (v). Patterns i-iii: initial MXene was dried at 100° C. for 22 h before intercalation. Patterns iv-v: as-received wet MXene was used as an initial material. The resulting powders were washed with DMF after intercalation. See Example 14.

The schematic of intercalation of HM into the MXene is shown in FIG. 45A. The (001) X-ray diffraction (XRD) peaks of MXene most pronounced before intercalation with HM and/or DMF, were still present after intercalation, but shifted to lower 2θ angles (FIG. 45B-C, FIG. 46). Table 5 summarizes the c-LPs values for the HM and HM in DMF treated materials. The c-LP of the initial material was 19.5±0.1 Å, a value that does not change much with post intercalation treatment. After the initial powder was exposed to HM and HM in DMF at 80° C. for 24 h, the c-LPs increased to 25.48±0.02 Å and 26.8±0.1 Å, respectively. The larger c-LP increase in the latter case points to a synergistic effect when the HM was dissolved in DMF prior to its intercalation. Note that when DMF alone was used, the increase in c was very small (22.9±0.2 Å), suggesting limited intercalation.

When the HM intercalated powders were heated to 120° C., their c-LPs decreased from 25.48 to 20.6±0.3 Å (FIG. 45B-iii and FIG. 45C-iii), signifying that the intercalation process was reversible. In contrast, heating the powders intercalated with HM and DMF to 120° C. resulted in a small reduction in c-LP (FIG. 45B-ii, FIG. 45C-ii). However, when the same powder was vacuum dried at 200° C., the c-LP decreased to 20.1±0.5 Å (FIG. 45B-ii, FIG. 45B-ii). It follows that the HM/DMF combination was more resistant to de-intercalation than HM alone. Without being bound by the correctness of any particular theory, this could be due to a higher boiling point of DMF (153° C.) compared to that of HM (114° C.).

TABLE 5 c-lattice parameters, in Å, for non-intercalated MXene and MXene treated with HM, HM and DMF, and dried in different conditions

| Intercalant | Non-intercalated | MD - non-intercalated | HM (XRD)‡ | MD (N/C ratio 0.375) | HM in DMF (XRD)‡ |
|---|---|---|---|---|---|
| Initial material* | 19.5 ± 0.1 | 19.85 ± 0.01 | 25.48 ± 0.02 | 25.31 ± 0.04 | 26.8 ± 0.1 |
| After drying @ 120° C. | 19.5 ± 0.1 | N/A | 20.6 ± 0.3 | N/A | 26.0 ± 0.2 |
| Vacuum drying @ 200° C. | 19.3 ± 0.2 | N/A | N/A | N/A | 20.1 ± 0.5 |

*Prior to intercalation, the $Ti_3C_2$-based powder was dried at 100° C. for 22 h.
‡Both HM and HM in DMF treatments were carried out at 80° C. for 24 h.

The XRD consistently showed that MXene were intercalated with HM. The absence of XRD peaks corresponding to a c-LP of 19.5 Å (FIG. 45B-i, FIG. 45C-i) implied that nearly entire space between MXene layers was intercalated.

Figure 47A:
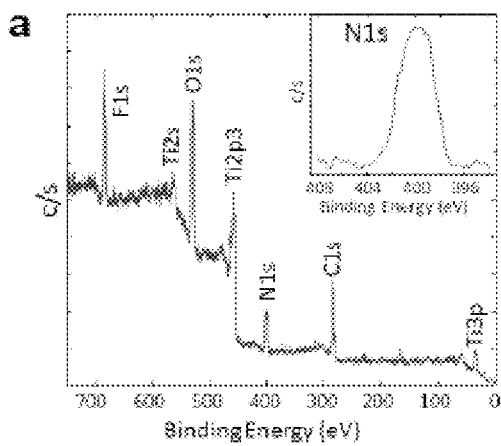
FIG. 47A-B shows XPS spectra of MXene intercalated with HM at 80° C. for 24 h (FIG. 47A) and with HM and DMF at 80° C. for 24 h (FIG. 47B). Both insets showed Nls peaks for corresponding samples.
Figure 47B:
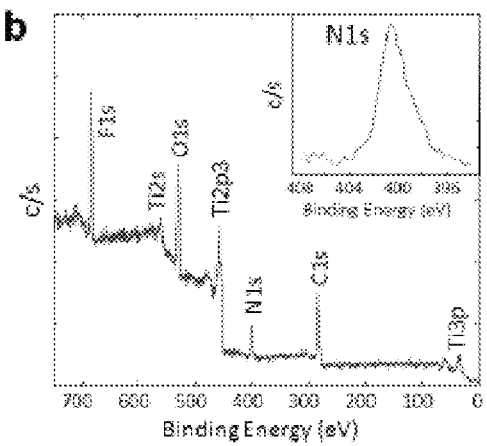

XPS spectra (FIG. 47) provided further evidence of intercalation. As it was previously described, pure exfoliated $Ti_3C_2$ sample showed presence of Ti—C and Ti—O bonds as well as OH groups suggested by the observed O1s peak around 530 eV. In case of intercalated samples, the N1s signal was observed around 400 eV in XPS spectra of both $Ti_3C_2$ treated with HM and HM/DMF (insets in FIGS. 47A and B, respectively). As expected, no peaks of nitrogen were detected in pure $Ti_3C_2$.

Figure 48A:
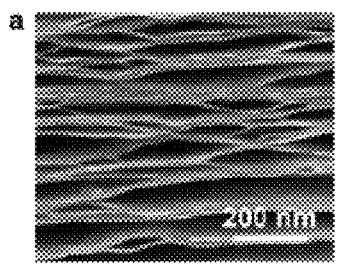
FIGS. 48A-F show images from electron microscopy analyses, including SEM images before (FIG. 48A) and after (FIG. 48B) intercalation of MXene with HM and DMF (24 h at 80° C.), respectively; TEM (FIG. 48C) and HRTEM (FIG. 48D) images with corresponding SAED pattern as inset of MXene before intercalation; TEM image (FIG. 48E) and SAED pattern (FIG. 48F) of intercalated MXene.
Figure 48B:
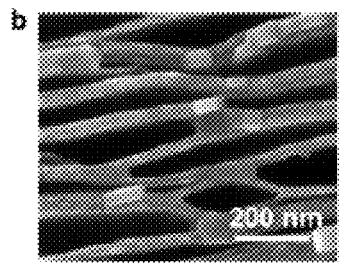

SEM images of the exfoliated $Ti_3C_2$ powders, before and after HM treatment in DMF at 80° C. for 24 h, shown in FIG. 48A-B, respectively, confirmed that: (i) the MXene remains exfoliated after intercalation, and, (ii) the layers apparently thicken (FIG. 48B) by gluing monolayers together forming 20-50 nm thick lamellas. These structures were formed when organics act as adhesive ligaments, gluing MXene monolayers together.

The smaller fragments attached to the edges of a larger MXene particles in FIG. 48B were debris that most probably were formed during the long (24 h) stirring with magnetic stirrer bar. Such debris has never been observed for non-intercalated $Ti_3C_2$. Their formation suggests a different mode of fracture of MXene layers after intercalation.

Figure 48C:
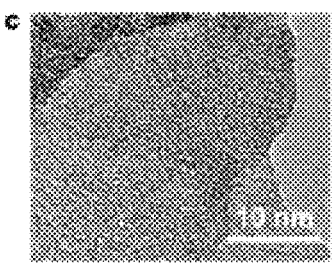
Figure 48D:
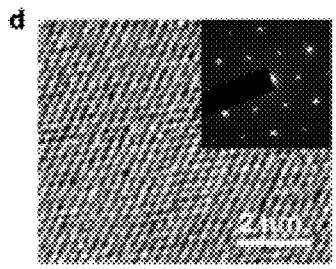
Figure 48E:
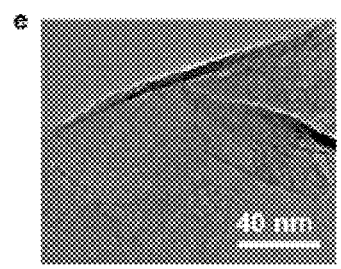
Figure 48F:
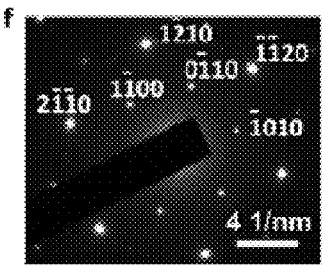

TEM images and corresponding SAED patterns of $Ti_3C_2$ intercalated with HM in DMF at 80° C. for 24 h (FIG. 48A-F) showed no significant changes in the structure of the basal planes of the $Ti_3C_2$ after intercalation (FIG. 48C and inset in FIG. 48D). When separate MXene sheets were observed, their SAED patterns (FIG. 48F) confirmed the same hexagonal crystal structure of the basal planes of the intercalated sample typical for both exfoliated $Ti_3C_2$ MXene (inset in FIG. 48D) and non-exfoliated $Ti_3AlC_2$ MAX phase. Measurements of the d-spacings for the intercalated materials gave the values 2.648 Å and 1.540 Å for the (U110) and (1210) lattice planes, respectively. These values result in an a-LP of 3.057 Å, a value that is in excellent agreement with the a-LP of exfoliated $Ti_3C_2$ before intercalation, as well as non-exfoliated $Ti_3AlC_2$, viz. 3.058 Å.

Figure 49:
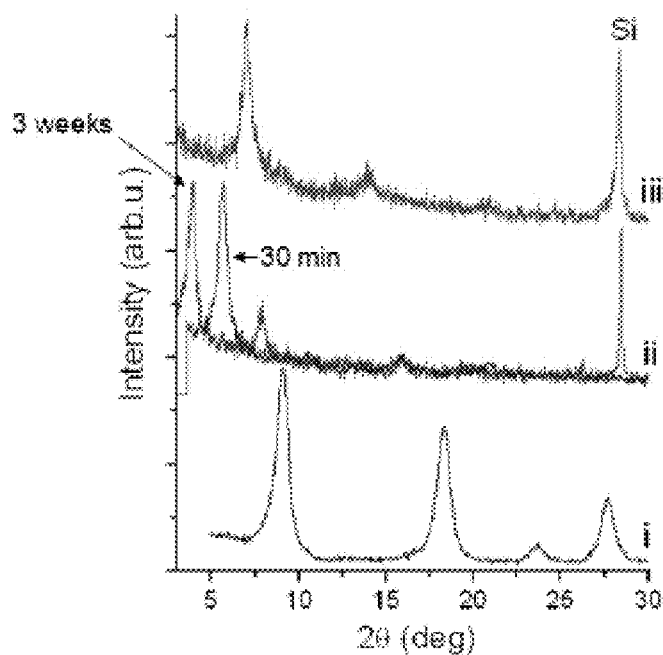
FIG. 49 shows XRD patterns of MXene: (i) before any treatment, (ii) after DMSO treatment taken 30 min and 3 weeks after drying in a desiccator at RT, (iii) after urea treatment.

Other potential intercalants were also tested. The following organic compounds were tested: thiophene, ethanol, tetrahydrofuran, formaldehyde, chloroform, toluene, hexane, DMSO, and urea. Of these, only DMSO and urea resulted in an increase in the c-LPs from 19.5±0.1 Å to 35.04±0.02 Å and 25.00±0.02 Å, respectively (FIG. 49). The intercalation of these compounds was in good agreement with data reported for kaolinite.

Interestingly, XRD patterns taken 3 weeks after the initial DMSO intercalation (FIG. 49-ii) showed an even larger downshift of the (002) peaks corresponding to a c-LP of 44.8±0.1 Å. Based upon this observation, together with the fact that MXene powders are highly hygroscopic and over the same period of time they become increasingly wet, this further increase of c-LPs over time may be due the intercalation of $H_2O$ from the ambient air into the pre-open interlayer space of the intercalated MXene, followed by capillary condensation of water. This effect was only observed for the DMSO intercalated MXene powders.

Figure 50:
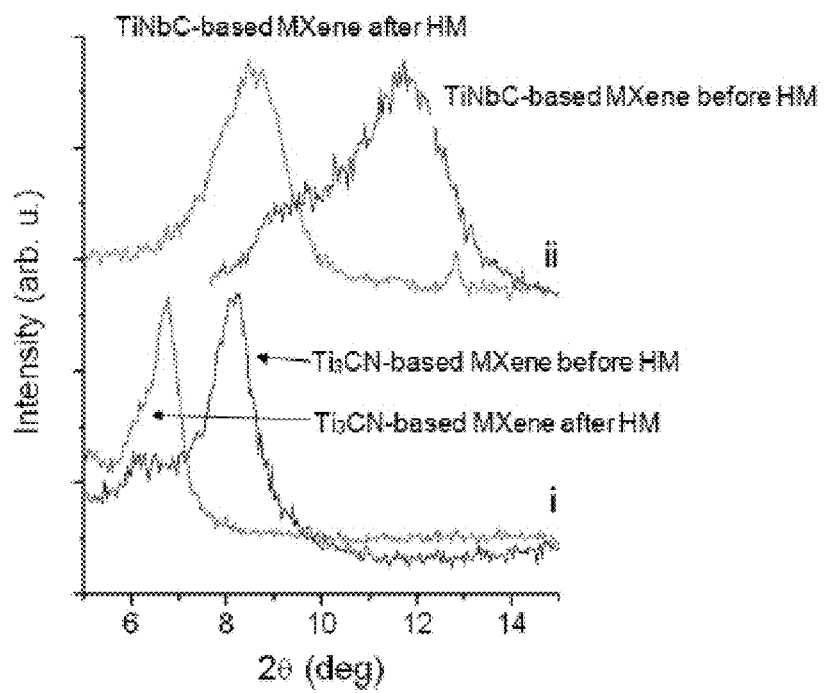
FIG. 50 shows XRD patterns of $Ti_3CN$-based MXene (i) before and after HM treatment and TiNbC-based MXene (i) before and after HM treatment.

Although the results above were obtained on $Ti_3C_2$, other MXenes can be intercalated in a similar way. To demonstrate that intercalation was a general phenomenon rather than the exclusive property of the $Ti_3C_2$-based MXene, the treatment of two other members of the MXene family, $Ti_3CN$ and TiNbC, was carried out with HM. As in the case of $Ti_3C_2$, the shift of the major XRD peak to lower 2θ angles (FIG. 50) confirmed their intercalation. It is important to note that one of those phases was a carbonitride with the same general formula as $Ti_3C_2$ ($M_3X_2$), whereas the other one represented a different kind of MXene with the formula $M_2X$ (TiNbC), consistent with the thinking that other MXenes can form intercalation compounds as well.

To further support the fact of intercalation, the resistivity of non-intercalated MXenes and MXenes treated with HM was measured (Table 6). Expansion of the van der Waals gap between sheets requires energy that comes from charge transfer between the guest and MXene, and alters the number of charge carriers, affecting the conductivity. As expected, the resistivity values of all intercalated samples were higher than that of non-intercalated due to the increase of their c-LPs after intercalation. The difference in magnitude of the resistivity increase for different intercalated MXenes at relatively the same expansion might be partially explained by different number of MXene atomic layers. In case of $M_3X_2$, the resistivity increased by an order of magnitude whereas the increase by two orders is observed for $M_2C$ compounds. It is important to note that the resistivity values might be affected by sample density and the pressure used to compress the discs. For instance, the sheet resistivity of non-intercalated $Ti_3C_2$ pressed at 0.8 GPa reported in Table 6 was lower than that pressed at 1 GPa.

The properties of intercalation compounds, including electrical conductivity discussed above, to a large extent were determined by the amount, arrangement and reactions of the guest molecules with the host material. In addition, the structure of the intercalant often provided a key to deciphering the intercalation mechanisms. However, as alluded to above, this problem's complexity was illustrated by the large body of literature on the structure of HM intercalation in clays.

Concerning the co-intercalation of HM and DMF, only simple geometrical considerations were provided. The increase of c-LP by 7.3 Å over the non-intercalated MXene, measured for this material after intercalation at room temperature (Table 5) could be explained by the insertion of both HM and DMF molecules. Based on the experimentally measured increase in MXene c-LPs, upon co-intercalation of HM and DMF, the insertion of 1 $N_2H_4$ and 1 DMF molecule in a stack configuration into the interlayer spacing of MXene can be suggested. The resulting increase in c-LP (7.3 Å) is, in this case, close to the sum of 2.4 Å and 5.0 Å—the changes in c-LPs reported for $N_2H_4$ and DMF intercalated kaolinites, respectively. As noted above, the reduction of this value to 6.5 Å after drying at 120° C. (Table 5) could be attributed to the partial de-intercalation of HM molecules, leaving behind DMF molecules.

Example 15

Sheet Resistivities and Contact Angles of MX-ene Discs

To measure the sheet resistances and the contact angle of various MXene compositions, MXene discs (25 mm in diameter, 300 µm thick) were cold-pressed from the reacted powders. The latter were placed in a die and cold-pressed to a load corresponding to a stress of 1 GPa. The surface or sheet resistances of cold-pressed, free-standing MXene discs were measured using a four-probe technique (Cascade Probe Station CPS-1303-24 with 4-point probe head Alessi C4S-57, Cascade Microtech, Inc., Beaverton, USA).

Contact angle measurements of deionized water were also performed at room temperature using the sessile drop technique. Ten microliter water drops were placed on the surfaces of cold-pressed MXene discs. The contact angles were measured from photographs taken with a CCD camera yielding an accuracy of approximately ±3°.

The densities of the cold-pressed discs of the various MXene compositions (Table 7) varied between 2.91 g/cm³ for $Ti_2C$ to 6.82 g/cm³ for $Ta_4C_3$. If one assumes the c lattice

TABLE 6

Sheet resistivity, resistivity and density of cold-pressed discs for different non-intercalated MXenes and MXenes treated with Hydrazine Monohydrate (HM).

| Sample | Sheet Resistivity, Ω/□ | | Resistivity, Ωm | | Density, g/cm³ | |
|---|---|---|---|---|---|---|
| | Non-intercalated | HM treated | Non-intercalated | HM treated | Non-intercalated | HM treated |
| $Ti_3C_2$ | 61 | 243 | 0.016 | 0.056 | 2.58 | 2.71 |
| $Ti_3CN$ | 43 | 711 | 0.011 | 0.249 | 3.22 | 2.90 |
| $Nb_2C$ | 321 | 12806 | 0.139 | 4.977 | 3.75 | 3.47 |
| TiNbC | 230 | 44661 | 0.092 | 17.471 | 3.67 | 3.01 | parameters listed in Table 1 and OH terminated surfaces of MXene sheets, then it is possible to calculate the theoretical densities. The last row in Table 7 lists the measured densities of the pressed discs. The numbers in parentheses list the % of theoretical densities that range from 50 to ca. 65%.

The sheet resistivity and resistivities of the various MXene discs are also shown in Table 7. The resistivity values are higher than the MAX phases before treatment (<10Ω/□) presumably because of the replacement of the A layers with OH and/or F. When it is assumed that surface groups are similar in all of the exfoliated MAX phases, the difference in the resistivity between the different phases can be partially explained by the different number of atomic layers (3, 5, and 7 for $M_2X$, $M_3X_2$, and $M_4X_3$ phases, respectively). It is important to note that the resistivity values reported in Table 7 should be significantly higher than single MXene sheets because of the method by which the resistivity was measured. For example, the resistivity of bulk sintered $Ti_3AlC_2$ is 0.39 μΩm. When $Ti_3AlC_2$ powders were cold-pressed at 1 GP, their resistivity increased to 1200 μΩ-m, a, roughly, 3000 time increase.

Contact angle measurement results for water droplets on the cold-pressed discs of exfoliated phases are also listed in Table 7. These values are lower than those of the corresponding MAX phases—that were also measured in this work on cold-pressed samples, which were around 60°. The reduction in contact angle can be explained by the presence of OH surface groups after the HF treatment. In contradistinction, graphene can be transformed from superhydrophobic to superhydrophilic by altering the surface groups. The hydrophilicity of the MXenes would be an advantage when using aqueous electrolytes in energy storage devices or dispersing in water and alcohols for further processing.

TABLE 7

Resistivity and Contact Angle of Water on Cold-Pressed Free-Standing Discs for Different Exfoliated Phases and Their Densitiies

| Property | $Ti_2C$ | TiNbC | $Ti_3CNx$ | $Ta_4C_3$ | $Ti_3C_2$ |
|---|---|---|---|---|---|
| Resistivity, Ω/□ | 339 | 171 | 125 | 104 | 22 |
| Resistivity, Ω m | 0.068 | 0.052 | 0.037 | 0.021 | 0.005 |
| Contact angle, deg | 32 | 31 | 27 | 41 | 34 |
| Density of cold pressed discs$^a$, g/cm$^3$ (% of theoretical) | 2.91 (62%) | 3.23 (52%) | 2.95 (64%) | 6.82 (53%) | 3.12 (60%) |

$^a$The densities were estimated from the dimensions and weights of the cold-pressed discs. Number in parentheses is relative theoretical density assuming OH termination of the MX-ene surfaces and the c parameters listed in Table 1.

Example 16

Transparent Conductive Films

The fabrication of ~1×1 cm$^2$ $Ti_3C_2T_s$ films by selective etching of Al, from sputtered epitaxial $Ti_3AlC_2$ films, in aqueous HF or $NH_4HF_2$ is described herein. Films that were about 19 nm thick, etched with $NH_4HF_2$, transmit ~90% of the light in the visible-to-infrared range and exhibit metallic conductivity down to ~100 K. Below 100 K, the films' resistivities increase with decreasing temperature and exhibit negative magnetoresistances; both observations consistent with a weak localization phenomenon characteristic of 2D defective solid. This advance opens the door for the use of MXenes in electronic, photonic and sensing applications.

The examples provided herein describe results derived from $Ti_3C_2T_s$. It should be appreciated that the results described herein are expected to be reproducible with other MXene materials, and separate embodiments include those wherein properties are described with respect to these other MXene materials. That is, other specific embodiments include the other MXene materials described herein resulting in properties analogous to those described herein, and the articles derived from such intercalated materials.

The materials described here represent a departure from existing literature in several ways: (1) they are produced as continuous epitaxial thin films; (2) In all previous studies, the etchant was HF. Here it is shown that ammonium bi-fluoride, $NH_4HF_2$ can be used instead; (3) the one-step synthesis of a MXene, intercalated with ammonia, is demonstrated; (4) Availability of epitaxial films on transparent and insulating sapphire substrates enabled the measurement of some of the fundamental physical properties, such as optical absorption, in a broad wavelength range, and the temperature dependence of conductivity and magnetoresistance down to 2 K. These films show high transparency for wavelengths in the visible to infrared range.

Example 16.1

Methods and Materials

Synthesis of $Ti_3C_2$.

Two chemicals were used to etch, at room temperature, the Ti3AlC2 films. The first was 50% concentrated HF (Sigma Aldrich, Stockholm, Sweden). Samples of nominal thickness of 15, 28, 43, and 60 nm were etched for 10, 15, 60 and 160 min, respectively. The second was 1 M $NH_4HF_2$ (Sigma Aldrich, Stockholm, Sweden). Samples of the same thickness as those mentioned above were etched for 150, 160, 420, and 660 min, respectively. After etching, the samples were rinsed in deionized water, then in ethanol.

Optical and Electrical Characterization.

Transmittance values of the films were obtained using a spectrophotometer (Perkin Elmer Lambda 950 UV-Vis) with a 2-nm slit width and resolution. Spectra were corrected with both 100% and 0% transmittance background spectra. A bare sapphire substrate was used as a reference. The number of MXene layers obtained for FIG. 54B were calculated by dividing the total film thicknesses by the c/2 where c is the lattice parameters obtained from XRD.

Room-temperature resistivities were measured using a four-point probe method. Three sheet-resistance measurements were taken for each sample. The errors reported in Table 8 were calculated. The resistivity was obtained by multiplying the sheet resistance with the corresponding average film thickness.

The temperature-dependent in-plane resistivity measurements were performed in a Physical Property Measurement System (Quantum Design, San Diego, USA) using an external current source (Keithley 6220, Ohio, USA) and nanovoltmeter (Keithley 2182A). A linear four-point probe geometry was used. Gold wires were attached to the films using silver paint. Positive and negative currents were applied at each temperature to eliminate any thermal offsets. The MR measurements were performed with the magnetic field—up to 10 T—applied out of the plane of the film.

Example 16.2

Results

Figure 51A:
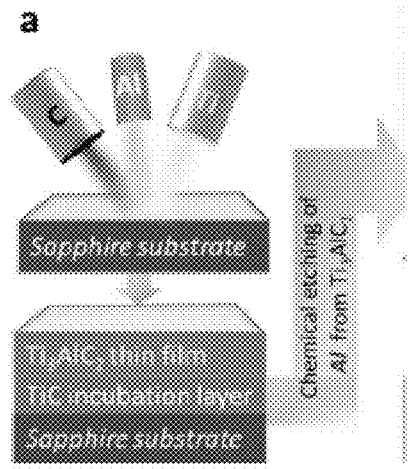
FIG. 51A shows schematic diagram of steps used to produce epitaxial MXene films.
Figure 51B:
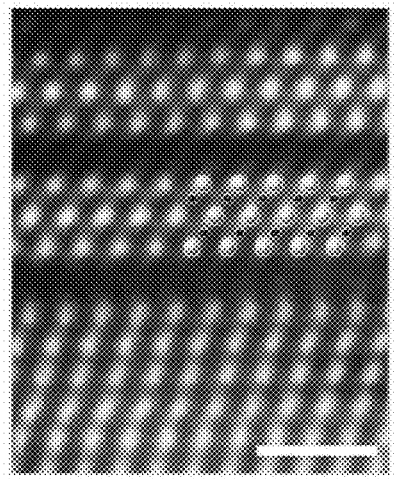
FIG. 51B shows a STEM image of the first two $Ti_3C_2T_s$ layers after applying Wiener filter; scale bar is equal to 1 nm.

The starting films used were 15 to 60 nm thick $Ti_3AlC_2$ films deposited onto sapphire (0001) substrates by magnetron sputtering. FIG. 51A shows a schematic of the process starting from the sputter-deposition of $Ti_3AlC_2$. Prior to the deposition of the $Ti_3AlC_2$ layers, a TiC incubation layer was formed on the sapphire. The latter is key to growing epitaxial $Ti_3AlC_2$ films. This is followed by etching of the Al layers resulting in 2D $Ti_3C_2T_s$, layers where $T_s$ stands for the surface —O, —OH, or —F terminations resulting from the aqueous HF etchant (see Example 16.1). The $Ti_3C_2$ surfaces are presumed to be OH-terminated. A scanning transmission electron microscopy (STEM) image of the interface between the TiC incubation layer and $Ti_3C_2T_s$ is shown FIG. 51B. The fact that the very first MXene layer has an ordered structure bodes well for the production of single layer MXene films.

In these experiments, ammonium bi-fluoride, $NH_4HF_2$ was used as an etchant reported to produce the MXene. As described above, other bifluorides and in-situ HF precursors many also be used for this purpose. The main advantages of the latter are reduced hazard, relacitve to HF and milder etchant. A third advantage is the concomitant intercalation of cations during the etching process. For brevity's sake, hereafter these films will be referred to as $Ti_3C_2T_s$-IC, where the IC represents the intercalated species, viz. $NH_3$ and $NH_4^+$ (see below).

Figure 52A:
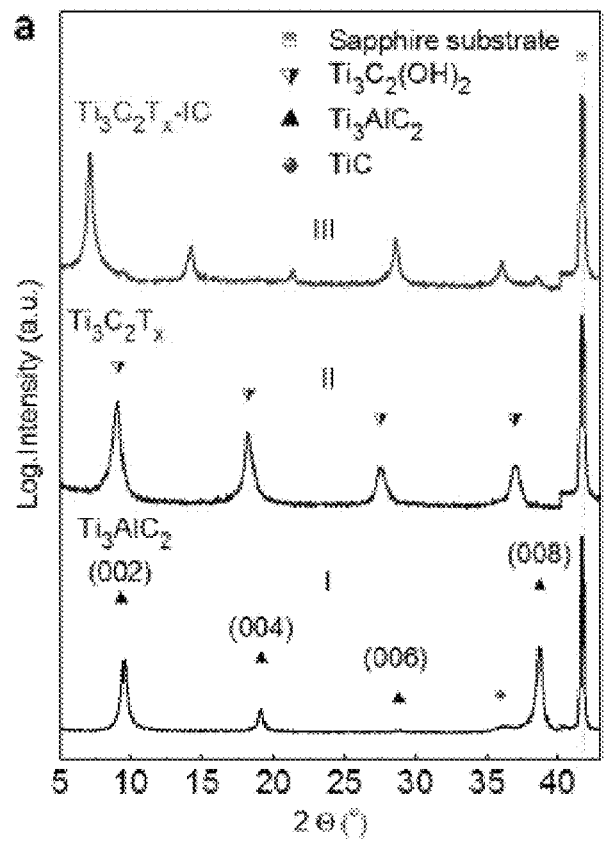
FIG. 52A-E provide spectra for phase and chemical analysis.
Figure 53A:
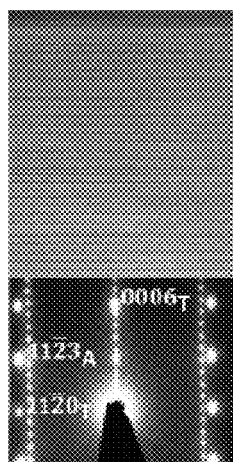

A typical XRD pattern of an as-deposited $Ti_3AlC_2$ film (FIG. 52A, I) shows the (000l) peaks from $Ti_3AlC_2$, a TiC incubation layer and the sapphire substrate. The presence of only peaks corresponding to basal-plane oriented $Ti_3AlC_2$ indicates epitaxial growth, a fact also confirmed by transmission electron microscopy (TEM) and selected area electron diffraction (SAED) (FIG. 53A). The $Ti_3C_2T_s$ XRD pattern (FIG. 52A, II) on the other hand, shows a downshift in angle of the 000l peaks corresponding to an increase in the c lattice parameter from 18.6 Å for $Ti_3AlC_2$ to 19.8 Å for $Ti_3C_2T_s$. The latter value agrees with previous work on $Ti_3C_2T_s$ synthesized from $Ti_3AlC_2$ powders. The XRD pattern of $Ti_3C_2T_s$-IC (FIG. 52A, III), is similar to the other two, except that now c is further increased to 24.7 Å. Similar behavior was observed when $Ti_3AlC_2$ powders were intercalated with $NH_4OH$ or $NH_4F$ after HF etching. In both cases, the c lattice expansion was of the order of 25%. The independence of the increase in the c lattice parameter on the nature of the anion of the etching solution strongly suggests that the cations ($NH_4^+$) and/or ammonia ($NH_3$), and not the anions, are the intercalated species. Herein, the etching and intercalation occur in a single step. This is an important result because it considerably simplifies the intercalation process.

X-ray photoelectron spectroscopy (XPS) measurements were performed on the various films in order to characterize their chemical states and atomic compositions. The XPS results, shown in FIG. 52B-D for films, with a nominal thickness of 60 nm, demonstrate a shift in the Ti 2p and C 1s (FIGS. 52B and C) toward higher binding energies for the titanium carbide species in $Ti_3AlC_2$, $Ti_3C_2T_s$ and $Ti_3C_2T_s$-IC, compared to those of binary TiC (shown in FIGS. 53B and C as vertical lines), indicating the change in the nature of bonding between the Ti and C atoms in $Ti_3AlC_2$ and the corresponding MXenes. The latter most likely occurs because valence electrons are withdrawn from the Ti atoms, and subsequently from the C atoms, in the MXene layers by the surface functional groups, as well as, from the interaction of the surface with the intercalated compounds. The removal of Al is verified by the high-resolution spectra in the Al 2p region for $Ti_3C_2T_s$ and $Ti_3C_2T_s$-IC (FIG. 52D), in which a very weak Al signal most probably originating from aluminum fluoride. The $Ti_3AlC_2$, Al 2p signal corresponds to Al bonded to Ti, as well as, surface aluminum oxide.

The reactions of HF with $Ti_3AlC_2$ are postulated to include:

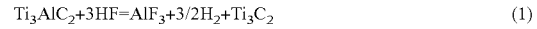

Reaction (1) is followed by reactions (2) and (3), which result in OH and F terminated $Ti_3C_2$ surfaces or $Ti_3C_2T_s$. The elemental ratio obtained from the analysis of high-resolution (XPS) spectra is $Ti_3C_{22}O_2F_{0.6}$. As indicated by XPS, terminal hydroxyl and fluoride groups exist on the surface of the material, thereby indirectly confirming the aforementioned reactions. EDX mapping in the TEM also confirms the presence of F and O atoms between the $Ti_3C_2$ layers.

As discussed above for $NH_4HF_2$ etched $Ti_3AlC_2$, intercalation of ammonium species between the resulting $Ti_3C_2T_s$ layers occurs concomitantly to the etching of the Al layers. It is thus reasonable to conclude that in this case the following reactions are operative:

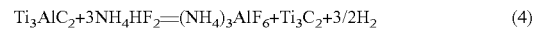

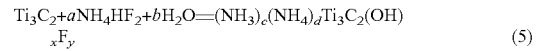

Figure 52B:
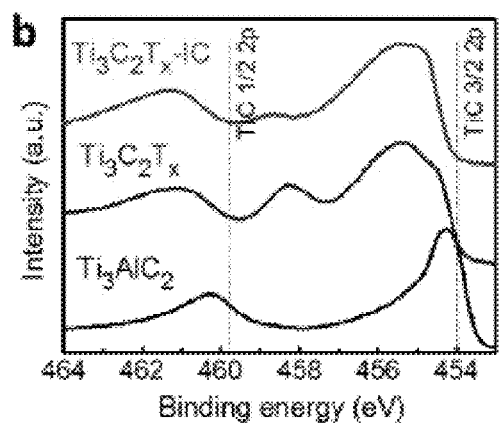
Figure 52C:
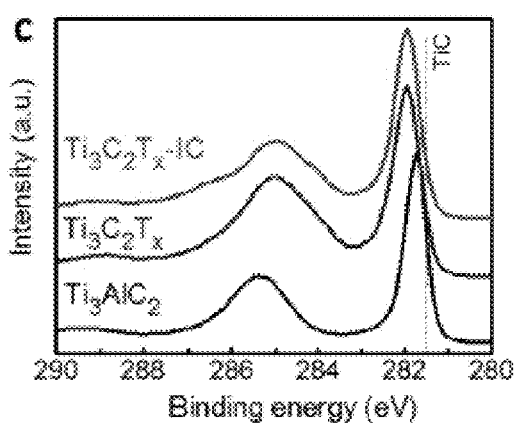
Figure 52D:
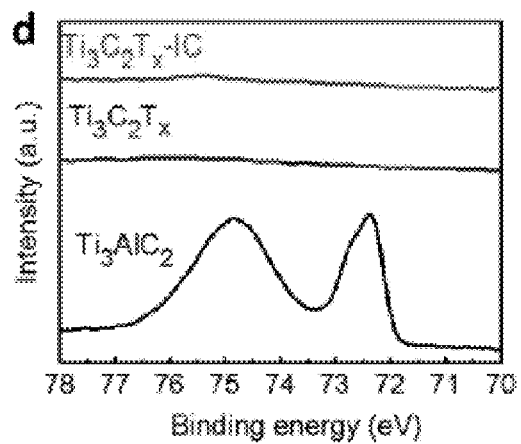
Figure 52E:
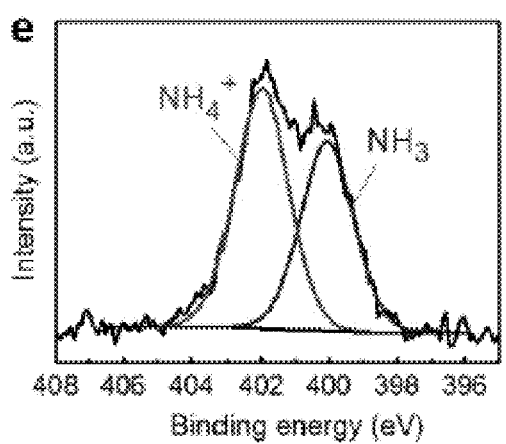

Unlike HF etching, etching with $NH_4HF_2$ results in formation of $(NH_4)_3AlF_6$ according to reaction (4). Reaction (5) depicts the intercalation of $NH_3$ and $NH_4^{+1}$ between the $Ti_3C_2T_s$ layers 30. In order to confirm the nature of the intercalating species in $Ti_3C_2T_s$-IC, a high-resolution XPS spectrum of the N is region was recorded (FIG. 52E). The latter was best fitted by two components: one for $NH_4^{+1}$ (55.8% of N 1s; peak position: 402 eV, FWHM: 1.8 eV)30; the other for $NH_3$ (44.2% of N 1s; peak position: 400.1 eV, FWHM: 1.8 eV)28,29. It is, thus, reasonable to conclude that both species intercalated this MXene.

The elemental ratio obtained from the analysis of high-resolution XPS spectra of $Ti_3C_2$ produced by $NH_4HF_2$ etching of $Ti_3AlC_2$ was $Ti_3C_{2.3}O_{1.2}F_{0.7}N_{0.2}$. Here again, the XPS analysis indicated the presence of terminal hydroxyl and fluoride groups.

Cross-sectional scanning TEM micrographs of as-deposited $Ti_3AlC_2$ films, before (FIGS. 53A and D) and after etching with HF (FIGS. 53B and E) or $NH_4HF_2$ (FIGS. 53C and F) clearly showed the presence of the TiC incubation layers and the effects of etching on the films' microstructures. The SAED patterns confirmed the out-of-plane epitaxial relationship $Ti_3AlC_2(0001)//TiC(111)//Al_2O_3(0001)$. At 18.6 Å, the c lattice parameter for $Ti_3AlC_2$, obtained from the SAED pattern and TEM micrographs, was in excellent agreement with that calculated from XRD (18.6 Å). At 19.5-20 Å, the c lattice parameter of $Ti_3C_2T_s$ obtained from SAED pattern also matches the one from XRD (19.8 Å). At 21 Å, the c for $Ti_3C_2T_s$-IC measured from the SAED pattern is considerably lower than that obtained from XRD (25 Å). The most probable reason for this state of affairs is the de-intercalation of the ammonium species during TEM sample preparation and/or observation.

Figure 53B:

The light elements of the surface termination groups (O, H and F) cannot be seen between the layers, but the larger and non-uniform spacings seen in FIGS. 53B, C, E and F indirectly confirmed the weak interactions between the MXene layers after etching and the formation of a 2D structure. The non-uniform interlayer spacing observed in the STEM images of the HF-etched sample (FIG. 53B) could also account for the peak broadening observed in XRD (FIG. 52A).

Prior to etching, the initial thicknesses of the films examined in the TEM were 60 nm (FIG. 53A). However, as a result of the increase in c and the separation between the MXene layers, due to exfoliation, the etched films were thicker than the initial films (Table 8). Comparing the atomic layers in $Ti_3C_2T_s$-IC (FIGS. 53C and F) to those of the $Ti_3C_2T_s$ layers (FIGS. 53B and E), it was obvious that the former were more uniformly spaced. This result most probably reflected the milder nature of $NH_4HF_2$ as compared to HF. For the latter the reaction is faster (Table 8) and more vigorous than the former. Another possible explanation was that the intercalation of ammonia species led to stronger interactions between MXene layers, essentially "gluing" them together as observed for other MXene intercalation compounds.

In terms of light transmittance, both $Ti_3C_2T_s$ and $Ti_3C_2T_s$-IC films were significantly more transparent than $Ti_3AlC_2$ of the same intial thickness, 15 nm, (Table 8 and FIG. 54A). The increased transparency of $Ti_3C_2T_s$ and $Ti_3C_2T_s$-IC, compared to that of $Ti_3AlC_2$ was also evident visually.

With 90% transmittance, the $Ti_3C_2T_s$-IC films were the most transparent, followed by the $Ti_3C_2T_s$ films at 70%. With a transmittance of 30%, the $Ti_3AlC_2$ films were the least transparent. It is worth noting here that the transmittance of all films would have been higher had the TiC incubation layer been absent.

Figure 54B:
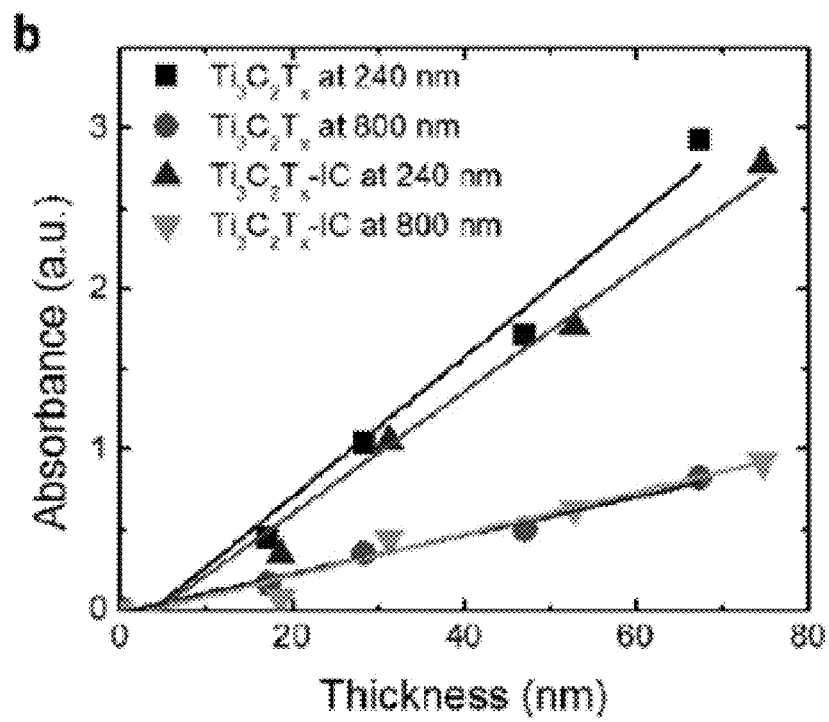

A linear dependence of the absorbance—that is independent of the wavelength of the light—on the thickness of the $Ti_3C_2T_s$ and $Ti_3C_2T_s$ IC films was observed (FIG. 54B). The similarities in the transmittance curves and the linear dependencies of absorbance values for both samples, suggest similar structures for $Ti_3C_2T_s$ and $Ti_3C_2T_s$-IC. A crude estimation of the transmittance of a single MXene layer, d, (since each length c is comprised of two MXene layers, d is approximately equal to the film thickness divided by 2c) could be obtained from the linear fits of absorbance vs. d. The transmittances, calculated thusly, at a wavelength of 240 nm, for single layers of $Ti_3C_2T_s$ and $Ti_3C_2T_s$-IC are about 90.5% and 91.5%, respectively; the corresponding transmittances, at a wavelength of 800 nm, are 97.3% and 97.1% respectively. The latter values are quite close to those reported for graphene single layers. Note that to obtain the aforementioned values, both the thickness and absorbance of the TiC seed layer were neglected.

TABLE 8

Thickness, etching duration, resistivity, and light transmittance-at a wavelength of 700 nm-of unetched and etched $Ti_3AlC_2$ thin films. Each set had the same nominal thickness before etching

|  |  | Deposition Time (minutes) | Thickness, nm | Etching duration, min | Resistivity, $\mu\Omega \cdot m$ | Transmittance, % |
|---|---|---|---|---|---|---|
| Set 1 | $Ti_3AlC_2$ | 5 | $15.2 \pm 0.5^a$ |  | $0.45 \pm 0.1$ | 31 |
|  | $Ti_3C_2T_s$ |  | $17.2 \pm 0.8^a$ | 9.5 | $39.23 \pm 1.21$ | 68 |
|  | $Ti_3C_2T_s$—IC |  | $18.7 \pm 0.6^a$ | 150 | $4472.75 \pm 323$ | 85 |
| Set 2 | $Ti_3AlC_2$ | 10 | $27.7 \pm 0.8^a$ |  | $0.34 \pm 0.01$ | 14 |
|  | $Ti_3C_2T_s$ |  | $28.4 \pm 1.8^a$ | 15 | $2.28 \pm 0.04$ | 49 |
|  | $Ti_3C_2T_s$—IC |  | $31.3 \pm 1.2^a$ | 160 | $5.01 \pm 0.03$ | 37 |
| Set 3 | $Ti_3AlC_2$ | 20 | $43.4 \pm 3.6^b$ |  | $0.31 \pm 0.01$ | 5.2 |
|  | $Ti_3C_2T_s$ |  | $47.1 \pm 3.5^b$ | 60 | $22.27 \pm 0.43$ | 30 |
|  | $Ti_3C_2T_s$—IC |  | $52.8 \pm 2.5^b$ | 420 | $30.90 \pm 2.79$ | 28 |
| Set 4 | $Ti_3AlC_2$ | 30 | $60.0 \pm 5.4^c$ |  | $0.35 \pm 0.01$ | 3.4 |
|  | $Ti_3C_2T_s$ |  | $67.4 \pm 0.5^c$ | 160 | $1.76 \pm 0.02$ | 15 |
|  | $Ti_3C_2T_s$—IC |  | $74.7 \pm 0.5^c$ | 660 | $54.01 \pm 4.51$ | 14 |

Figure 53C:
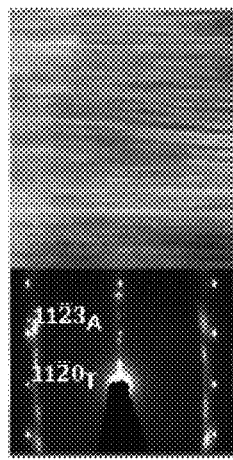
Figure 53D:
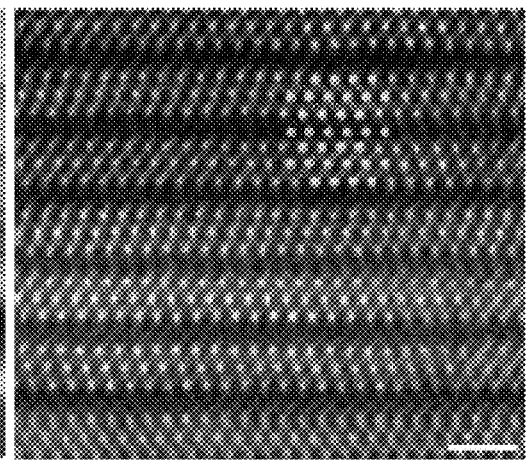

[a] Determined by XRR.
[b] Interpolated.
[c] Obtained from direct measurement in TEM (FIG. 53A-B).
[d] Obtained from direct measurement in TEM after accounting for the decrease in thickness due to partial de-intercalation (FIG. 53C).

Figure 55A:
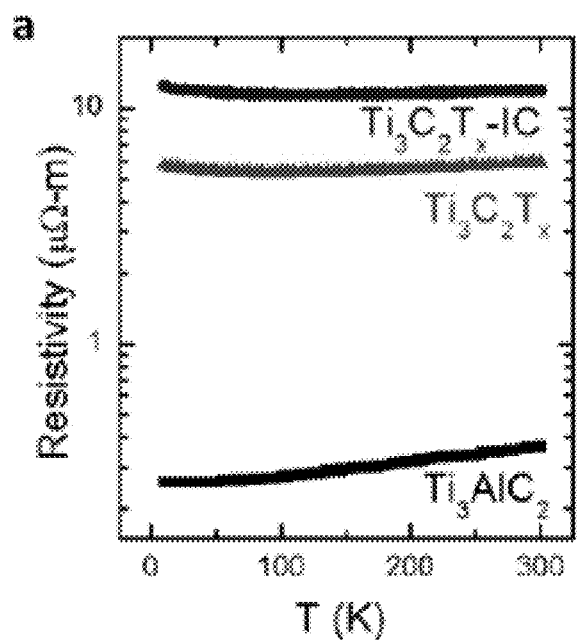
FIG. 55A-C shows the dependence of the electrical behavior of $Ti_3AlC_2$, $Ti_3C_2T_s$ and $Ti_3C_2T_s$-IC films on temperature and magnetic field.

The electrical properties also confirm the metallic-like nature of the conductivities of all films despite their optical transparency. The $Ti_3AlC_2$ films were metallic with resistivity, p, values in the range of 0.37 to 0.45 $\mu\Omega m$. The latter increased linearly with increasing temperature (FIG. 55A). Furthermore p increases with decreasing film thickness (Table 8). The resistivity values of the $Ti_3C_2T_s$-IC films are systematically higher than those produced by HF etching. For instance, 28 nm nominally thick $Ti_3C_2T_s$ and $Ti_3C_2T_s$-IC films have $\rho$ values of 2.3 and 5.0 $\mu\Omega m$, respectively. This result is also consistent with the resistivities of MXenes intercalated with organic compounds. The $\rho$'s of the etched films also depend significantly on etching time; longer etching times lead to higher $\rho$ values. Note that the results listed in Table 8 were those obtained upon the full MAX to MXene conversion. The latter was determined by intermittent etching of each film, followed by XRD. When the $Ti_3AlC_2$ peaks disappeared, the etching process was arrested.

At 1.8 $\mu\Omega m$, a 60 nm nominally thick $Ti_3C_2T_s$ sample was the most conductive of the HF etched films $Ti_3C_2T_s$ films (Table 8). However, at 15%, its transmittance was poor. The 15 nm nominally thick $Ti_3C_2T_s$ sample exhibited the highest transmittance (68%) with a $\rho$ of 39.2 $\mu\Omega m$. For the $Ti_3C_2T_s$-IC films, the lowest resistivity was 5.0 $\mu\Omega m$, with a transmittance of about 37%. The most transparent (>85%) $Ti_3C_2T_s$ film had a resistivity of ≈4.5 m$\Omega m$. And while this transmittance value was comparable to ITO, the sheet resistance was roughly an order of magnitude higher than ITO films having the same transmittance. The higher resistivities observed here may be due to the morphology of the as-deposited films. While $Ti_3AlC_2$ films were predominantly c-axis oriented (FIG. 51A), there is also a secondary grain population wherein the basal planes are not parallel to the substrate. If the conductivity along [0001] was significantly lower than that along the basal planes, such grains, when etched, will act as insulating islands. Reducing the fraction of such grains should result in films that are more conductive when etched.

It is predicted theoretically that altering the terminal bonds would alter the electronic properties of MXenes. Pure $Ti_3C_2$ was predicted to have a metallic behavior, whereas $Ti_3C_2F_2$ and $Ti_3C_2(OH)_2$ were predicted to have band gaps of 0.05 and 0.1, respectively. Thus, there is room for enhancement of the conductivity of $Ti_3C_2$ by eliminating the surface groups and/or enhancing the quality of the films.

To elucidate the conduction mechanisms of the MXene layers, their resistivities and magnetoresistances (MRs) from room temperature down to about 2.5 K were measured. FIG. 55A shows the temperature dependent resistivity for $Ti_3AlC_2$, $Ti_3C_2T_s$ and $Ti_3C_2T_s$-IC films of 28 nm nominal thickness.

Figure 55B:
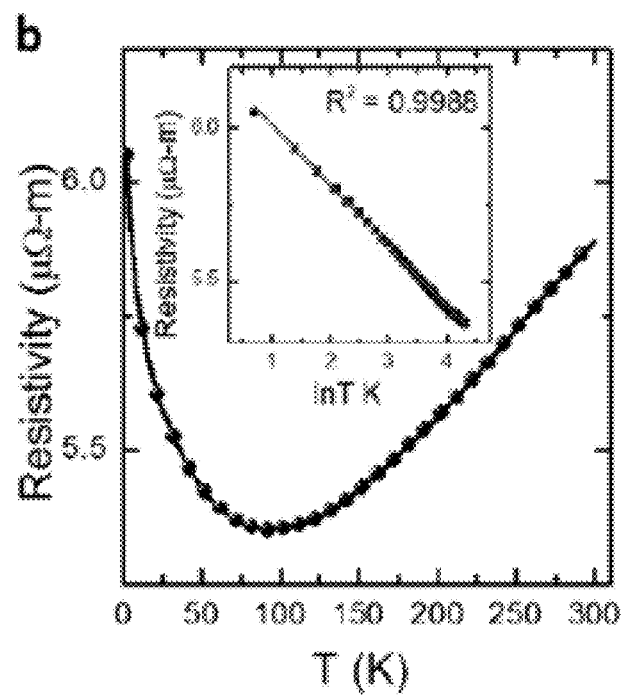
Figure 55C:
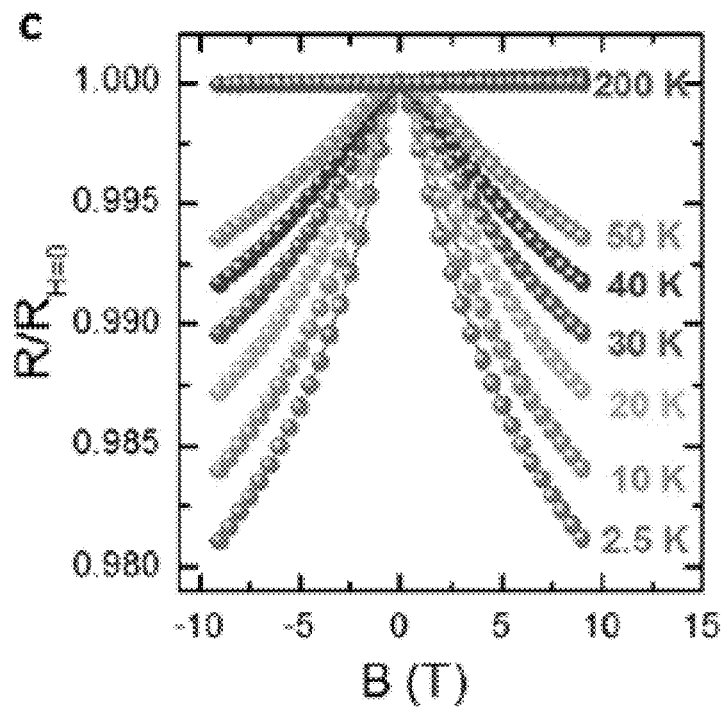

The $Ti_3AlC_2$ film exhibited metallic behavior from 300 K down to about 10 K. For the $Ti_3C_2T_s$ and $Ti_3C_2T_s$-IC films, on the other hand, metallic behavior was observed from 300 to about 100 K; below 100 K the resistivity increases with decreasing temperature (FIG. 55B). Similar low-temperature behavior was observed in other $Ti_3C_2T_s$ and $Ti_3C_2T_s$-IC films. The low temperature transport data can best be fit assuming $\rho \cdot \ln T$ (inset in FIG. 55B).

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, in their entirety.

What is claimed:

1. A polymer composite comprising:
   (a) an organic polymer; and
   (b) a planar MXene composition comprising at least one layer having first and second surfaces, each layer comprising:
   a substantially two-dimensional array of crystal cells,
   each crystal cell having an empirical formula of $M_{n+1}X_n$, such that each X is positioned within an octahedral array of M,
   wherein M is at least one Group IIIB, IVB, VB, or VIB metal,
   wherein each X is C, N, or a combination thereof and n=1, 2, or 3;
   wherein at least one of said surfaces of each layer has surface terminations comprising alkoxide, carboxylate, halide, hydroxide, hydride, oxide, sub-oxide, nitride, sub-nitride, sulfide, thiol, or a combination thereof;
   wherein the planar MXene composition is distributed within the polymer.

2. The polymer composite of claim 1, wherein the organic polymer comprises a thermoset or thermoplastic polymer or polymer resin, elastomer, or mixtures thereof.

3. The polymer composite of claim 1, wherein the organic polymer comprises an aromatic or heteroaromatic moiety within the polymer.

4. The polymer composite of claim 3, wherein the aromatic or heteroaromatic moiety within the polymer is phenyl, biphenyl, pyridinyl, bipyridinyl, naphthyl, or pyrimidinyl.

5. The polymer composite of claim 1, wherein the organic polymer comprises an anisotropic polymer that is directionally oriented to be parallel in a polymer composite composition.

6. The polymer composite of claim 5, wherein the anisotropic polymer is a liquid crystal polymer.

7. The polymer composite of claim 1, wherein the organic polymer comprises an amide or ester derivative of terephthalic acid or naphthalic acid.

8. The polymer composite of claim 1, wherein the organic polymer comprises polyethylene, polypropylene, polyethylenenaphthalate (PEN), polyethylene terephthalate (PET), polybutylene terephthalate (PBT), polyether etherketone (PEEK), polyamide, polyaryletherketone (PAEK), polyethersulfone (PES), polyethyleneimine (PEI), poly (p-phenylene sulfide) (PPS), polyvinyl chloride (PVC), polytetrafluoroethylene (PTFE), polyvinylidene difluoride (PVDF), or a polyvinyl fluoride (PVF).

9. The polymer composite of claim 1 wherein the planar MXene composition is present in the organic polymer in an amount ranging from about 0.1 wt % to about 50 wt %, relative to the combined weight of the organic polymer and planar MXene composition.

10. The polymer composite of claim 1, wherein the polymer composite is in a form having a planar configuration, and the organic polymer is oriented in a plane coincident with the plane of that planar configuration.

11. The polymer composite of claim 10, wherein the substantially two-dimensional array of crystal cells of the MXene composition defines a plane, and this plane is substantially aligned with plane of the oriented polymer coincident with the plane of the polymer composite.

12. The polymer composite claim 11, the polymer composite having a flexural strength that is greater than the flexural strength of a corresponding polymer without the presence of the planar MXene composition.

13. The polymer composite claim 11, the polymer composite having a stiffness that is greater than the stiffness of a corresponding polymer without the presence of the planar MXene composition.

14. The polymer composite of claim 1, wherein the $M_{n+1}X_n$ comprises $Sc_2C$, $Sc_2N$, $Ti_2C$, $Ti_2N$, $Mo_2C$, $V_2C$, $V_2N$, $Cr_2C$, $Cr_2N$, $Zr_2C$, $Zr_2N$, $Nb_2C$, $Nb_2N$, $Hf_2C$, $Hf_2N$, $Ti_3C_2$, $Ti_3N_2$, $V_3C_2$, $V_3C_2$, $Ta_3C_2$, $Ta_3N_2$, or $Ti_4C_3$, $Ti_4N_3$, $V_4C_3$, $V_4N_3$, $Ta_4C_3$, $Ta_4N_3$, or a combination thereof.

15. The polymer composite of claim 1, wherein the $M_{n+1}X_n$ comprises $Ti_3C_2$, $Ti_3CN$, $Ti_2C$, $Ta_4C_3$, or $(V_{1/2}Cr_{1/2})_3C_2$.

16. A conductive composition comprising
   a planar MXene composition comprising at least one layer having first and second surfaces, each layer comprising:
   a substantially two-dimensional array of crystal cells,
   each crystal cell having an empirical formula of $M_{n+1}X_n$, such that each X is positioned within an octahedral array of M,
   wherein M is at least one Group IIIB, IVB, VB, or VIB metal,
   wherein each X is C, N, or a combination thereof and n=1, 2, or 3;
   wherein at least one of said surfaces of each layer has surface terminations comprising alkoxide, carboxylate, halide, hydroxide, hydride, oxide, sub-oxide, nitride, sub-nitride, sulfide, thiol, or a combination thereof;
   said assembly having thickness of from 15 nm to 75 nm and a surface resistivity of less than about 50 micro-ohm-meter.

17. The conductive composition of claim 16, wherein the stacked assembly is at least 65% tranparent to at least one wavelength of light in a range of from about 250 nm to about 850 nm.

18. The conductive composition of claim 17, wherein the stacked assembly is at least 95% tranparent to at least one wavelength of light in a range of from about 250 nm to about 850 nm.

19. The conductive composition of claim 17, wherein the $M_{n+1}X_n$ comprises $Sc_2C$, $Sc_2N$, $Ti_2C$, $Ti_2N$, $Mo_2C$, $V_2C$, $V_2N$, $Cr_2C$, $Cr_2N$, $Zr_2C$, $Zr_2N$, $Nb_2C$, $Nb_2N$, $Hf_2C$, $Hf_2N$, $Ti_3C_2$, $Ti_3N_2$, $V_3C_2$, $V_3C_2$, $Ta_3C_2$, $Ta_3N_2$, or $Ti_4C_3$, $Ti_4N_3$, $V_4C_3$, $V_4N_3$, $Ta_4C_3$, $Ta_4N_3$, or a combination thereof.

20. The conductive composition of claim 16, wherein $M_{n+1}X_n$ comprises $Ti_3C_2$, $Ti_3CN$, or $Ti_2C$.

21. An electronic device comprising a stacked assembly of at least two layers having first and second surfaces, each layer comprising:
a substantially two-dimensional array of crystal cells,
each crystal cell having the empirical formula of $M_{n+1}X_n$, such that each X is positioned within an octahedral array of M;
wherein M is a Group IIIB, IVB, VB, or VIB metal;
each X is C, N, or a combination thereof; and
n=1, 2, or 3;
wherein at least one of said surfaces of each layer has bound thereto surface terminations comprising alkoxide, carboxylate, halide, hydroxide, hydride, oxide, sub-oxide, nitride, subnitride, sulfide, thiol, or a combination thereof;
said stacked assembly having a surface resistivity of less than about 50 micro-ohm-meter.

22. The electronic device of claim 21, wherein the stacked assembly exhibits at least 65% tranparency to at least one wavelength of light in a range of from about 250 nm to about 850 nm.

23. The electronic device of claim 21, wherein the stacked assembly further comprises intercalated lithium, sodium, potassium, cesium, ammonium, magnesium, or aluminum ions.

24. The electronic device of claim 23, wherein the stacked assembly further comprises intercalated hydrazine, hydrazine monohydrate, DMSO, urea, or N, N-dimethylformamide.

25. The electronic device of claim 21, wherein $M_{n+1}X_n$ comprises $Sc_2C$, $Sc_2N$, $Ti_2C$, $Ti_2N$, $Mo_2C$, $V_2C$, $V_2N$, $Cr_2C$, $Cr_2N$, $Zr_2C$, $Zr_2N$, $Nb_2C$, $Nb_2N$, $Hf_2C$, $Hf_2N$, $Ti_3C_2$, $Ti_3N_2$, $V_3C_2$, $V_3C_2$, $Ta_3C_2$, $Ta_3N_2$, or $Ti_4C_3$, $Ti_4N_3$, $V_4C_3$, $V_4N_3$, $Ta_4C_3$, $Ta_4N_3$, or a combination thereof.

26. The electronic device of claim 21, wherein $M_{n+1}X_n$ comprises $Ti_3C_2$, TiNbC, $Ti_3CN$, or $Ti_2C$.

27. An electronic device of claim 23 that is an ion battery.

28. An electronic device of claim 23 that is a lithium ion battery.

29. An electronic device of claim 23 that is a metal-ion capacitor.

30. A suspension of delaminated flakes, the flakes comprising MXene compositions comprising:
at least one layer having first and second surfaces, each layer comprising:
a substantially two-dimensional array of crystal cells,
each crystal cell having an empirical formula of $M_{n+1}X_n$, such that each X is positioned within an octahedral array of M,
wherein M is at least one Group IIIB, IVB, VB, or VIB metal,
wherein each X is C, N, or a combination thereof and n=1, 2, or 3;
wherein at least one of said surfaces of each layer has surface terminations comprising alkoxide, carboxylate, halide, hydroxide, hydride, oxide, sub-oxide, nitride, sub-nitride, sulfide, thiol, or a combination thereof.

31. The suspension of claim 30, wherein $M_{n+1}X_n$ comprises $Sc_2C$, $Sc_2N$, $Ti_2C$, $Ti_2N$, $Mo_2C$, $V_2C$, $V_2N$, $Cr_2C$, $Cr_2N$, $Zr_2C$, $Zr_2N$, $Nb_2C$, $Nb_2N$, $Hf_2C$, $Hf_2N$, $Ti_3C_2$, $Ti_3N_2$, $V_3C_2$, $V_3C_2$, $Ta_3C_2$, $Ta_3N_2$, or $Ti_4C_3$, $Ti_4N_3$, $V_4C_3$, $V_4N_3$, $Ta_4C_3$, $Ta_4N_3$, or a combination thereof.

32. The suspension of claim 26, wherein $M_{n+1}X_n$ comprises $Ti_3C_2$, $Ti_3CN$, $Ti_2C$, $Ta_4C_3$, or $(V_{1/2}Cr_{1/2})_3C_2$.

33. The suspension of claim 30, wherein the delaminated flakes are suspended in an aqueous medium.

34. The suspension of claim 30, wherein the delaminated flakes are suspended in isopropanol.

* * * * *